(12) United States Patent
Bielewicz et al.

(10) Patent No.: US 8,852,112 B2
(45) Date of Patent: Oct. 7, 2014

(54) CATHETER WITH DEFLECTABLE IMAGING DEVICE AND BENDABLE ELECTRICAL CONDUCTOR

(75) Inventors: Paul A. Bielewicz, Newark, DE (US); Richard W. Denny, Castle Rock, CO (US); Dennis R. Dietz, Littleton, CO (US); Michael J. Fife, Littleton, CO (US); Joseph A. Huppenthal, Flagstaff, AZ (US); David J. Messick, Flagstaff, AZ (US); Craig T. Nordhausen, Parker, CO (US); Clyde G. Oakley, Centennial, CO (US); Ryan C. Patterson, North Salt Lake City, UT (US); Jim H. Polenske, Bellemont, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 1001 days.

(21) Appl. No.: 12/347,637

(22) Filed: Dec. 31, 2008

(65) Prior Publication Data

US 2009/0292199 A1  Nov. 26, 2009

Related U.S. Application Data

(63) Continuation-in-part of application No. 12/163,325, filed on Jun. 27, 2008, now Pat. No. 8,285,362.

(60) Provisional application No. 60/946,807, filed on Jun. 28, 2007.

(51) Int. Cl.
| | | |
|---|---|---|
| *A61B 8/14* | (2006.01) | |
| *A61B 8/12* | (2006.01) | |
| *A61B 8/00* | (2006.01) | |
| *A61B 17/22* | (2006.01) | |
| *A61B 17/29* | (2006.01) | |
| *A61M 25/01* | (2006.01) | |
| *A61B 17/34* | (2006.01) | |
| *A61B 17/00* | (2006.01) | |
| *A61B 19/00* | (2006.01) | |

(52) U.S. Cl.
CPC .......... *A61B 8/12* (2013.01); *A61B 2017/22039* (2013.01); *A61B 2017/2906* (2013.01); *A61B 2017/22014* (2013.01); *A61M 25/0147* (2013.01); *A61B 17/3478* (2013.01); *A61B 2017/00867* (2013.01); *A61B 8/4466* (2013.01); *A61B 2019/528* (2013.01); *A61B 2017/003* (2013.01); *A61M 25/0138* (2013.01); *A61B 19/5225* (2013.01); *A61B 8/445* (2013.01)
USPC ........... 600/466; 600/437; 600/459; 600/462; 600/463; 600/467

(58) Field of Classification Search
None
See application file for complete search history.

(56) References Cited

U.S. PATENT DOCUMENTS

| | | | |
|---|---|---|---|
| 3,955,561 A | 5/1976 | Eggleton | |
| 4,059,098 A | 11/1977 | Murdock | |
| 4,060,889 A * | 12/1977 | Zielinski | ......................... 29/854 |
| 4,092,867 A | 6/1978 | Matzuk | |
| 4,149,419 A | 4/1979 | Connell, Jr. et al. | |
| 4,245,624 A | 1/1981 | Komiya | |
| 4,316,271 A | 2/1982 | Evert | |
| 4,327,738 A | 5/1982 | Green et al. | |
| 4,398,425 A | 8/1983 | Matzuk | |
| 4,399,703 A | 8/1983 | Matzuk | |
| 4,421,118 A | 12/1983 | Dow et al. | |
| 4,452,236 A | 6/1984 | Utsugi | |
| 4,455,872 A | 6/1984 | Kossoff et al. | |
| 4,474,184 A | 10/1984 | Harui | |
| 4,516,972 A * | 5/1985 | Samson | ....................... 604/526 |
| 4,559,951 A | 12/1985 | Dahl et al. | |
| 4,664,121 A | 5/1987 | Sanghvi et al. | |
| 4,747,411 A | 5/1988 | Ledley | |
| 4,756,313 A | 7/1988 | Terwilliger | |
| 4,784,148 A | 11/1988 | Dow et al. | |
| 4,794,930 A | 1/1989 | Machida et al. | |
| 4,841,979 A | 6/1989 | Dow et al. | |
| 4,895,158 A | 1/1990 | Kawabuchi et al. | |
| 4,977,898 A | 12/1990 | Schwarzschild et al. | |
| 4,995,868 A | 2/1991 | Brazier | |
| 5,030,204 A | 7/1991 | Badger et al. | |
| 5,070,879 A | 12/1991 | Herres | |

| | | | | | | |
|---|---|---|---|---|---|---|
| 5,090,956 | A | 2/1992 | McCoy | 6,679,849 B2 | 1/2004 | Miller et al. |
| 5,108,368 | A | 4/1992 | Hammerslag et al. | 6,689,066 B1 | 2/2004 | Omura et al. |
| 5,152,294 | A | 10/1992 | Mochizuki et al. | 6,709,396 B2 | 3/2004 | Flesch et al. |
| 5,159,931 | A | 11/1992 | Pini | 6,716,176 B1 | 4/2004 | Weston et al. |
| 5,168,864 | A | 12/1992 | Shockey | 6,780,197 B2 | 8/2004 | Roe et al. |
| 5,181,514 | A | 1/1993 | Solomon et al. | 6,832,477 B2 | 12/2004 | Gummin et al. |
| 5,191,890 | A | 3/1993 | Hileman | 6,908,434 B1 | 6/2005 | Jenkins et al. |
| 5,226,422 | A | 7/1993 | McKeighen et al. | 6,939,338 B2 | 9/2005 | Waldhauser et al. |
| 5,255,668 | A | 10/1993 | Umeda | 7,022,102 B2 | 4/2006 | Paskar |
| 5,268,531 | A | 12/1993 | Nguyen et al. | 7,037,269 B2 | 5/2006 | Nix et al. |
| 5,291,896 | A | 3/1994 | Fonger et al. | 7,226,417 B1 | 6/2007 | Eberle et al. |
| 5,306,245 | A | 4/1994 | Heaven | 7,232,433 B1 | 6/2007 | Schlesinger et al. |
| 5,318,008 | A | 6/1994 | Bullard | 7,311,659 B2 * | 12/2007 | Bob et al. .................. 600/153 |
| 5,345,940 | A | 9/1994 | Seward et al. | 7,451,595 B2 | 11/2008 | Komori et al. |
| 5,351,692 | A | 10/1994 | Dow et al. | 7,473,224 B2 | 1/2009 | Makin |
| 5,352,214 | A | 10/1994 | Oscarsson | 7,494,469 B2 | 2/2009 | Bruestle |
| 5,377,685 | A | 1/1995 | Kazi et al. | 7,507,205 B2 | 3/2009 | Borovsky et al. |
| 5,379,772 | A | 1/1995 | Imran | 7,524,289 B2 | 4/2009 | Lenker |
| 5,397,321 | A | 3/1995 | Houser et al. | 7,682,319 B2 | 3/2010 | Martin et al. |
| 5,398,689 | A | 3/1995 | Connor et al. | 7,798,971 B2 | 9/2010 | Flesch et al. |
| 5,402,789 | A | 4/1995 | Dow et al. | 2001/0047165 A1 | 11/2001 | Makower et al. |
| 5,413,107 | A | 5/1995 | Oakley et al. | 2002/0049383 A1 | 4/2002 | Swanson et al. |
| 5,427,107 | A | 6/1995 | Milo et al. | 2002/0062083 A1 * | 5/2002 | Ohara et al. .................. 600/462 |
| 5,454,795 | A | 10/1995 | Samson | 2002/0128554 A1 | 9/2002 | Seward |
| 5,456,258 | A | 10/1995 | Kondo et al. | 2004/0006277 A1 | 1/2004 | Langenhove et al. |
| 5,460,168 | A | 10/1995 | Masubuchi et al. | 2004/0045735 A1 * | 3/2004 | Varkey et al. ............. 174/120 R |
| 5,460,179 | A | 10/1995 | Okunuki et al. | 2004/0054388 A1 | 3/2004 | Osypka |
| 5,469,853 | A | 11/1995 | Law et al. | 2004/0158153 A1 | 8/2004 | Hirt et al. |
| 5,485,845 | A | 1/1996 | Verdonk et al. | 2004/0204650 A1 | 10/2004 | Taylor |
| 5,486,162 | A | 1/1996 | Brumbach | 2005/0015011 A1 | 1/2005 | Liard et al. |
| 5,507,725 | A | 4/1996 | Savage et al. | 2005/0016753 A1 * | 1/2005 | Seigerschmidt .......... 174/106 R |
| 5,531,119 | A | 7/1996 | Meyers | 2005/0027198 A1 | 2/2005 | Couvillon, Jr. |
| 5,545,200 | A | 8/1996 | West et al. | 2005/0059957 A1 | 3/2005 | Campbell et al. |
| 5,591,142 | A | 1/1997 | Van Erp | 2005/0228290 A1 | 10/2005 | Borovsky et al. |
| 5,630,806 | A | 5/1997 | Inagaki et al. | 2006/0085054 A1 * | 4/2006 | Zikorus et al. .................. 607/96 |
| 5,636,634 | A * | 6/1997 | Kordis et al. .................. 600/534 | 2006/0131061 A1 | 6/2006 | Seigerschmidt |
| 5,651,364 | A | 7/1997 | Yock | 2006/0173350 A1 | 8/2006 | Yuan et al. |
| 5,662,116 | A | 9/1997 | Kondo et al. | 2006/0184035 A1 | 8/2006 | Kimura et al. |
| 5,662,621 | A | 9/1997 | Lafontaine | 2006/0224142 A1 | 10/2006 | Wilson et al. |
| 5,681,280 | A | 10/1997 | Rusk et al. | 2006/0235304 A1 | 10/2006 | Harhen et al. |
| 5,699,805 | A | 12/1997 | Seward et al. | 2007/0016063 A1 | 1/2007 | Park et al. |
| 5,702,365 | A | 12/1997 | King | 2007/0073135 A1 | 3/2007 | Lee et al. |
| 5,779,643 | A | 7/1998 | Lum et al. | 2007/0073151 A1 | 3/2007 | Lee |
| 5,842,473 | A | 12/1998 | Fenster et al. | 2007/0088323 A1 | 4/2007 | Campbell et al. |
| 5,853,368 | A | 12/1998 | Solomon et al. | 2007/0106144 A1 | 5/2007 | Squeri |
| 5,873,828 | A | 2/1999 | Fujio et al. | 2007/0106203 A1 | 5/2007 | Wilson et al. |
| 5,876,386 | A | 3/1999 | Samson | 2007/0118035 A1 | 5/2007 | Secora |
| 5,993,424 | A | 11/1999 | Lorenzo et al. | 2007/0167813 A1 | 7/2007 | Lee et al. |
| 6,004,269 | A | 12/1999 | Crowley et al. | 2007/0167821 A1 | 7/2007 | Lee et al. |
| 6,068,629 | A | 5/2000 | Haissaguerre et al. | 2007/0167826 A1 | 7/2007 | Lee et al. |
| 6,071,274 | A | 6/2000 | Thompson et al. | 2007/0179380 A1 | 8/2007 | Grossman |
| 6,090,104 | A | 7/2000 | Webster, Jr. | 2007/0204613 A1 | 9/2007 | Alacqua et al. |
| 6,099,464 | A | 8/2000 | Shimizu et al. | 2007/0239010 A1 | 10/2007 | Johnson |
| 6,126,606 | A | 10/2000 | Bergstoel | 2007/0239023 A1 | 10/2007 | Hastings et al. |
| 6,149,599 | A | 11/2000 | Schlesinger et al. | 2008/0004528 A1 | 1/2008 | Fitzsimons et al. |
| 6,171,249 | B1 | 1/2001 | Chin et al. | 2008/0021408 A1 | 1/2008 | Jacobsen et al. |
| 6,190,353 | B1 | 2/2001 | Makower et al. | 2008/0033292 A1 | 2/2008 | Shafran |
| 6,210,362 | B1 | 4/2001 | Ponzi | 2008/0097391 A1 | 4/2008 | Feinberg et al. |
| 6,213,948 | B1 | 4/2001 | Barthe et al. | 2008/0097403 A1 | 4/2008 | Donaldson et al. |
| 6,213,958 | B1 | 4/2001 | Winder | 2008/0287797 A1 | 11/2008 | Lee et al. |
| 6,231,514 | B1 | 5/2001 | Lowe et al. | 2008/0287862 A1 | 11/2008 | Weitzner et al. |
| 6,233,490 | B1 | 5/2001 | Kasevich | 2009/0000383 A1 | 1/2009 | Knowles et al. |
| 6,233,491 | B1 * | 5/2001 | Kordis et al. .................. 607/122 | 2009/0088631 A1 | 4/2009 | Dietz et al. |
| 6,254,568 | B1 | 7/2001 | Ponzi | 2009/0093726 A1 | 4/2009 | Takayama et al. |
| 6,306,097 | B1 | 10/2001 | Park et al. | 2009/0118620 A1 | 5/2009 | Tgavalekos et al. |
| 6,315,732 | B1 | 11/2001 | Suorsa et al. | 2009/0124857 A1 | 5/2009 | Viola |
| 6,321,749 | B1 | 11/2001 | Toti et al. | 2009/0125019 A1 | 5/2009 | Douglass et al. |
| 6,375,615 | B1 | 4/2002 | Flaherty et al. | 2009/0198219 A1 | 8/2009 | Campbell et al. |
| 6,409,673 | B2 | 6/2002 | Yock | 2009/0264759 A1 | 10/2009 | Byrd |
| 6,443,944 | B1 | 9/2002 | Doshi et al. | 2009/0264767 A1 | 10/2009 | Griffin et al. |
| 6,461,298 | B1 | 10/2002 | Fenster et al. | | | |
| 6,514,210 | B2 * | 2/2003 | Ohara et al. .................. 600/462 | | | |
| 6,544,215 | B1 | 4/2003 | Bencini et al. | | | |
| 6,572,547 | B2 | 6/2003 | Miller et al. | | | |
| 6,585,718 | B2 | 7/2003 | Hayzelden et al. | | | |
| 6,589,182 | B1 | 7/2003 | Loftman et al. | | | |
| 6,592,520 | B1 | 7/2003 | Peszynski et al. | | | |
| 6,592,526 | B1 | 7/2003 | Lenker | | | |
| 6,645,152 | B1 | 11/2003 | Jung et al. | | | |

FOREIGN PATENT DOCUMENTS

| | | | |
|---|---|---|---|
| EP | 0530201 | A1 | 9/1991 |
| EP | 0521595 | A1 | 1/1993 |
| EP | 0774232 | A1 | 5/1997 |
| EP | 0829242 | A1 | 3/1998 |
| EP | 0982711 | A2 | 3/2000 |
| JP | 58-157114 | | 4/1982 |

| | | |
|---|---|---|
| JP | 1280446 A | 11/1989 |
| JP | 1284233 A | 11/1989 |
| JP | 1284234 A | 11/1989 |
| JP | 2021852 A | 1/1991 |
| JP | 5-508099 | 10/1992 |
| JP | 7-309 | 7/1995 |
| JP | 7-184900 | 7/1995 |
| JP | 8-280694 | 10/1996 |
| JP | 10-192279 | 7/1998 |
| JP | 10216146 | 8/1998 |
| JP | 2001-104311 | 4/2001 |
| JP | 2003-33354 | 2/2003 |
| JP | 2003-190289 | 7/2003 |
| JP | 2004-16725 | 1/2004 |
| JP | 2004-135693 | 5/2004 |
| JP | 2005-195998 A | 7/2005 |
| JP | 2006-158598 | 6/2006 |
| WO | 91/13648 | 9/1991 |
| WO | 2005/099584 A2 | 10/2005 |
| WO | 2006-117923 | 11/2006 |
| WO | 2009/006335 A1 | 1/2009 |
| WO | 2009/146458 A2 | 12/2009 |
| WO | 2009/158012 A2 | 12/2009 |

OTHER PUBLICATIONS http://www.eecs.umich.edu/~odonnel/images/acunav.jpg, printed Aug. 13, 2008, 1 page.

Baker et al., Usefulness of Live Three-Dimensional Transesophageal Echocardiography in a Congenital Heart Disease Center, The American Journal of Cardiology, Apr. 1, 2009, pp. 1025-1028, vol. 103, Issue 7, Elsevier Inc., USA.

Biocardia, Inc., BioCardia—Morph Acces Innovations, http://www.biocardia.com/morph/products.shtml, 2007, 2 pages.

Light et al., Two Dimensional Arrays for Real Time 3D Intracranial Imaging of the Brain, Ultrasonics Symposium, 2006, IEEE, Oct. 2, 2006, pp. 70-73, Canada.

Green et al., Initial Clinical Experience With Intracardiac Echocardiography in Guiding Balloon Mitral Valvuloplasty: Technique, Safety, Utility, and Limitations, Catheterization and Cardiovascular Interventions, 2004, pp. 385-394, vol. 63, No. 3, Wiley-Liss, USA.

Huang, Weimin, Shape Memory Alloys and their Application to Actuators for Deployable Structures, University of Cambridge Department of Engineering, Mar. 1998, 192 pages Peterhouse, USA.

Seward et al., Ultrasound Cardioscopy: Embarking on a New Journey, Mayo Clinic Proceedings, Jul. 1996, pp. 629-635, vol. 71, No. 7.

Strole et al., A Novel Flex Circuit Area-Array Interconnect System for a Catheter-Based Ultrasound Transducer, Presented at IMAPS 2002, Denver, CO, Sep. 5, 2002, 6 pages, USA.

Knackstedt et al., Semi-automated 3-dimensional intracardiac echocardiography: Development and initial clinical experience of a new system to guide ablation procedures, Heart Rhythm, Dec. 2006, pp. 1453-1459, vol. 3, No. 12, Elsevier Inc.

Kottenstette, Nicholas E., Designing Mechanisms with Shape Memory Alloys and Permanent Magnets, 162 pages, Massachusetts Institute of Technology, 162 pages, Feb. 1997, USA.

Matzuk, T. and Skolnick, M.L., Novel ultrasonic real-time scanner featuring servo controlled transducers displaying a sector image, Ultrasonics, Jul. 1978, pp. 171-178.

Bom et al., Early and recent intraluminal ultrasound devices, International Journal of Cardiac Imaging, Jun. 1989, pp. 79-88, vol. 4, Nos. 2-4, Springer, Netherlands.

Martin, Roy W. and Johnson, Christopher C., Design characteristics for intravascular ultrasonic catheters, International Journal of Cardiac Imaging, Jun. 1989, pp. 201-216, vol. 4, Nos. 2-4, Springer, Netherlands.

Siemens, Acuson AcuNav Diagnostic Ultrasound Catheter, 2008, 2 pages, Siemens AG.

Song, G., Design and control of a Nitinol wire actuated rotary servo, Smart Materials and Structures, Sep. 5, 2007, pp. 1796-1801, vol. 16, IPO Publishing, UK.

Lee et al., A Miniaturized Catheter 2-D Array for Real-Time, 3-D Intracardiac Echocardiography, IEEE Transactions on Ultrasonics, Ferroelectrics, and Frequency Control, Oct. 2004, pp. 1334-1346, vol. 51, No. 10, IEEE Institute of Electrical and Electronics, USA.

Lee et al., Dual Lumen Transducer Probes for Real-Time 3-D Interventional Cardiac Ultrasound, Ultrasound in Med. & Biol., Sep. 2003, pp. 1297-1304, vol. 29, No. 9, Elsevier Inc.

Zara et al., Intracardiac Ultrasound Scanner Using a Micromachine (MEMS) Actuator, IEEE Transactions on Ultrasonics, Ferroelectrics, and Frequency Control, Jul. 2000, pp. 984-993, vol. 47, No. 4, IEEE Ultrasonics, Ferroelectrics, and Frequency Control Society.

\* cited by examiner

*Primary Examiner* — Long V. Le
*Assistant Examiner* — Bradley Impink
(74) *Attorney, Agent, or Firm* — Amy L. Miller

(57) ABSTRACT

An improved catheter is provided. The catheter may include a deflectable member located at a distal end of the catheter. The deflectable member may comprise an ultrasound transducer array. The catheter may include a lumen extending from a proximal end of the catheter to the distal end. The lumen may be used to deliver an interventional device to a point distal to the distal end of the catheter. The deflectable member may be selectively deflectable in a pivot-like manner through an arc of at least 90 degrees. In embodiments where the deflectable member includes an ultrasound transducer array, the ultrasound transducer array may be operable to image both when aligned with the catheter and when pivoted relative to the catheter. When pivoted relative to the catheter, the ultrasound transducer array may have a field of view distal to the distal end of the catheter.

35 Claims, 63 Drawing Sheets

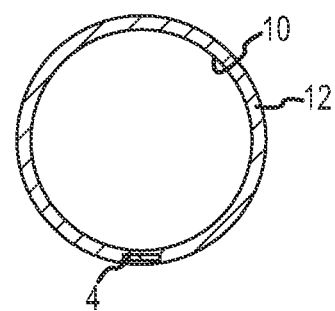
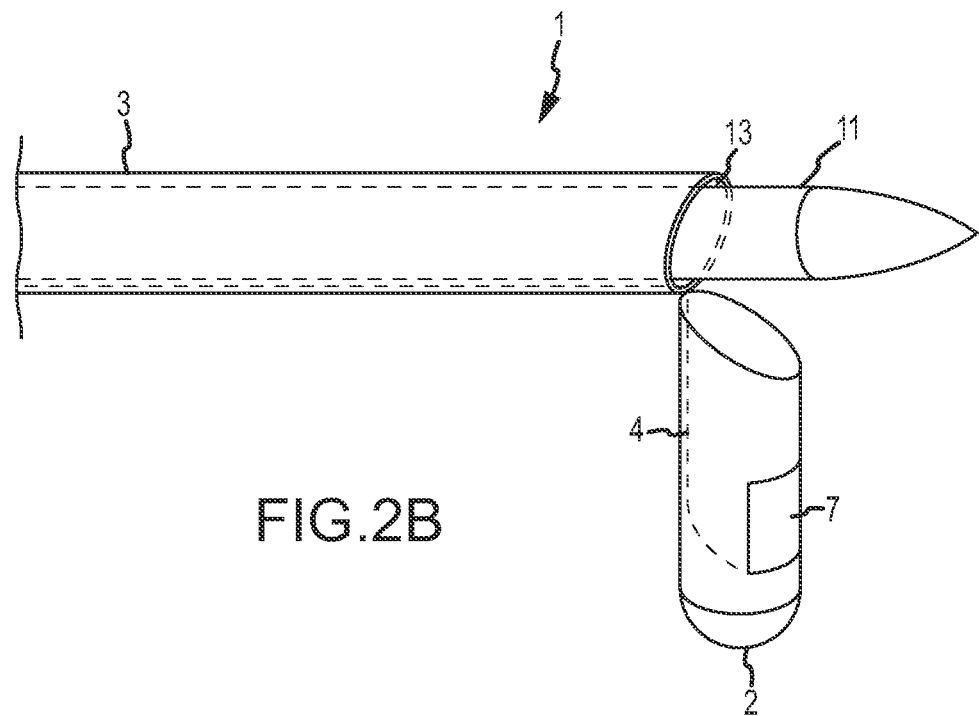

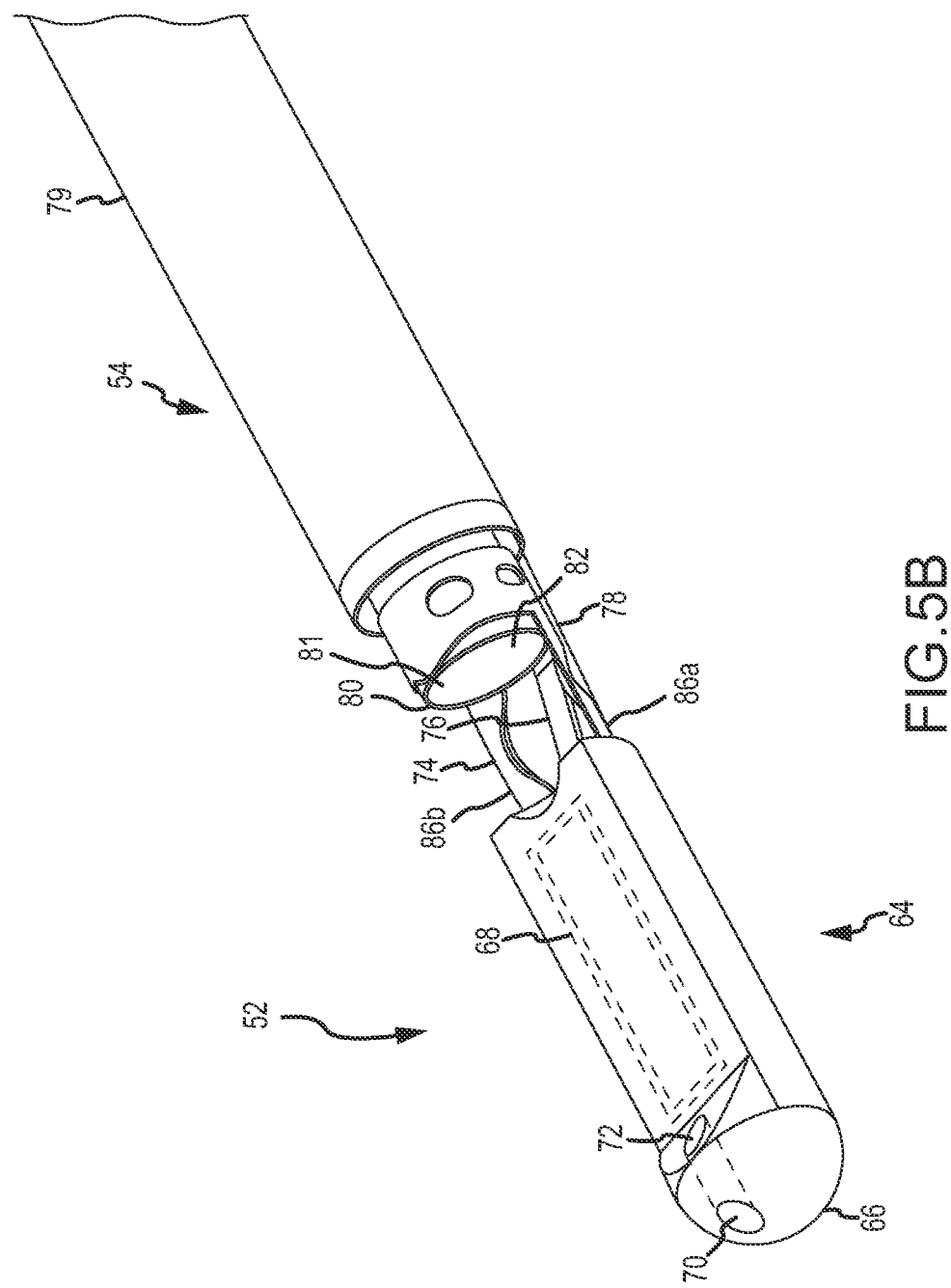

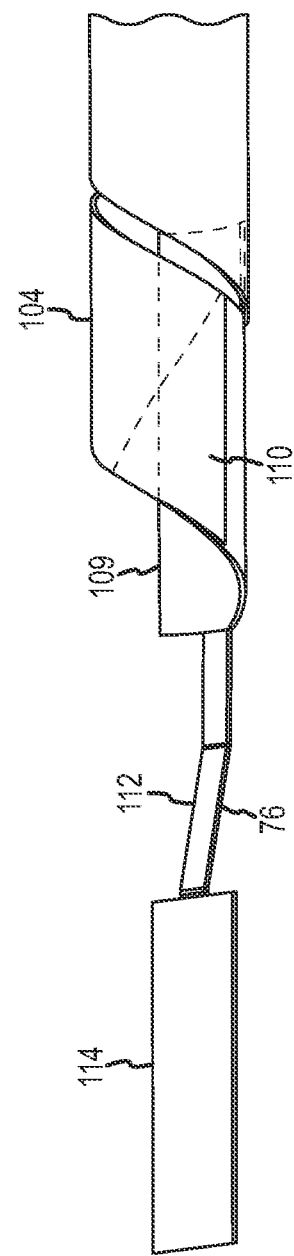

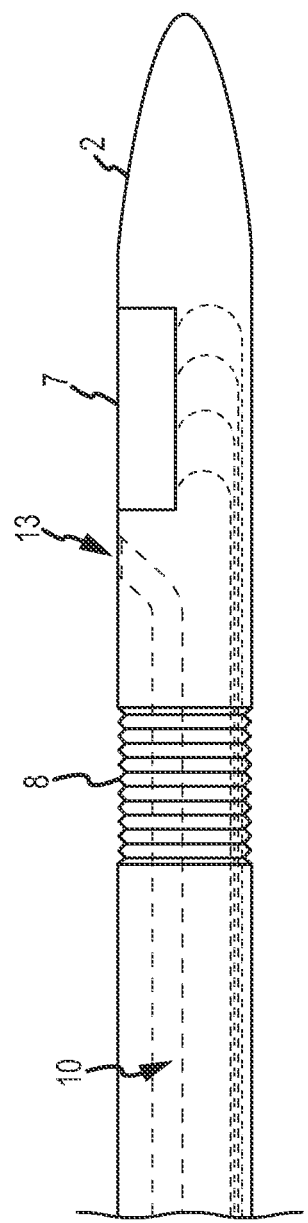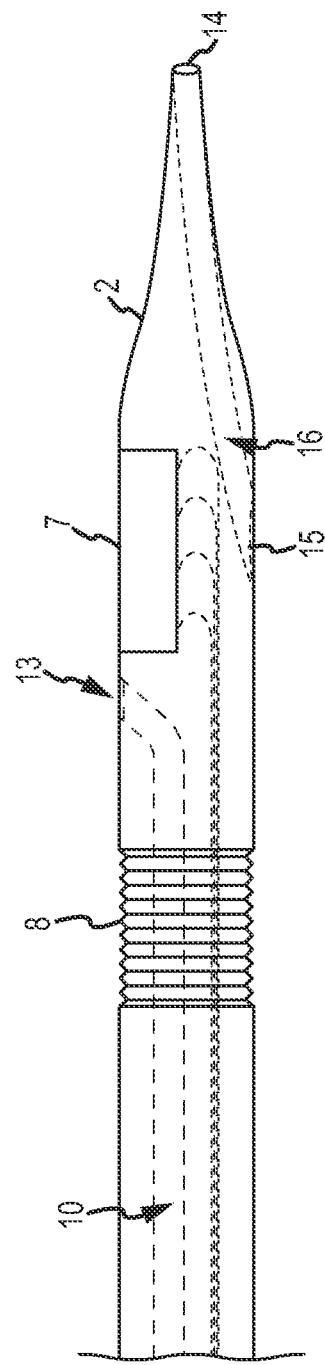

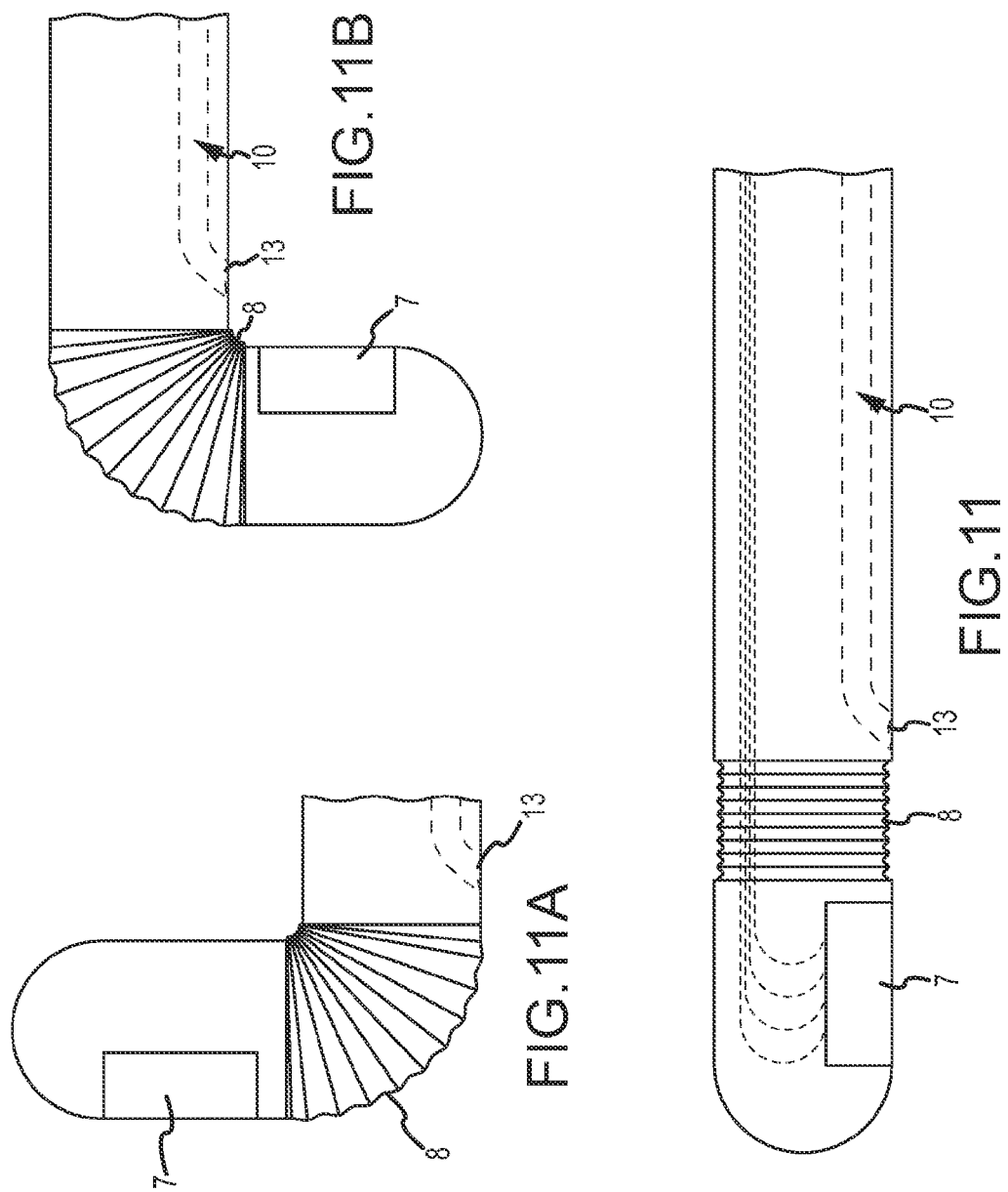

CATHETER WITH DEFLECTABLE IMAGING DEVICE AND BENDABLE ELECTRICAL CONDUCTOR

RELATED APPLICATIONS

This application claims priority as a continuation-in-part application of U.S. patent application Ser. No. 12/163,325, filed on Jun. 27, 2008, which claims the priority benefit of U.S. Provisional Application No. 60/946,807, filed Jun. 28, 2007. Each of the foregoing is incorporated herein by reference in its entirety.

FIELD OF THE INVENTION

The invention relates to improved catheters, and is particularly apt to catheters for imaging and interventional device delivery (e.g., ultrasound catheters with diagnostic or therapeutic device, agent or energy delivery capabilities) that can be used to obtain targeted images of interventional devices positioned at desired locations in the body of a patient and/or delivery target locations.

BACKGROUND OF THE INVENTION

Catheters are tubular medical devices that may be inserted into a body vessel, cavity or duct, and manipulated utilizing a portion that extends out of the body. Typically, catheters are relatively thin and flexible to facilitate advancement/retraction along non-linear paths. Catheters may be employed for a wide variety of purposes, including the internal bodily positioning of diagnostic and/or therapeutic devices. For example, catheters may be employed to position internal imaging devices, deploy implantable devices (e.g., stents, stent grafts, vena cava filters), and/or deliver energy (e.g., ablation catheters).

In this regard, use of ultrasonic imaging techniques to obtain visible images of structures is increasingly common, particularly in medical applications. Broadly stated, an ultrasonic transducer, typically comprising a number of individually actuated piezoelectric elements, is provided with suitable drive signals such that a pulse of ultrasonic energy travels into the body of the patient. The ultrasonic energy is reflected at interfaces between structures of varying acoustic impedance. The same or a different transducer detects the receipt of the return energy and provides a corresponding output signal. This signal can be processed in a known manner to yield an image, visible on a display screen, of the interfaces between the structures and hence of the structures themselves.

Numerous prior art patents discuss the use of ultrasonic imaging in combination with specialized surgical equipment in order to perform very precise surgical procedures. For example, a number of patents show use of ultrasonic techniques for guiding a "biopsy gun", i.e., an instrument for taking a tissue sample from a particular area for pathological examination, for example, to determine whether a particular structure is a malignant tumor or the like. Similarly, other prior art patents discuss use of ultrasonic imaging techniques to assist in other delicate operations, e.g., removal of viable eggs for in vitro fertilization, and for related purposes.

As internal diagnostic and therapeutic procedures continue to evolve, the desirability of enhanced procedure imaging via compact and maneuverable catheters has been recognized. More particularly, the present inventors have recognized the desirability of providing catheter features that facilitate selective positioning and control of componentry located at a distal end of a catheter, while maintaining a relatively small profile, thereby yielding enhanced functionality for various clinical applications.

SUMMARY OF THE INVENTION

The present invention relates to improved catheter designs. For purposes hereof, a catheter is defined as a device which is capable of being inserted into a body vessel, cavity or duct, wherein at least a portion of the catheter extends out of the body and the catheter is capable of being manipulated and/or removed from the body by manipulating/pulling on the portion of the catheter extending out of the body. In the various designs the catheter comprises an outer tubular body having a wall, a proximal end and a distal end. The catheter may further include a deflectable member located at the distal end of the outer tubular body. The deflectable member may include one or more therapeutic and/or diagnostic devices. For example, the deflectable member may include an imaging device such as an ultrasound transducer array. Further, the ultrasound transducer array may be a one dimensional array, one and a half dimensional array, or a two dimensional array. The deflectable member may be selectively deflectable relative to the outer tubular body to facilitate operation of componentry comprising the deflectable member.

In an additional aspect, at least a portion of the deflectable member may be permanently located outside of the outer tubular body. In this regard, the deflectable member may be selectively deflectable away from a center axis of the outer tubular body. In certain embodiments, such deflectability may be at least partially or entirely distal to the distal end of the outer tubular body.

In one aspect, the catheter may also include a lumen for delivering an interventional device extending through the outer tubular body from the proximal end of the outer tubular body to a point distal thereto. For purposes hereof, "interventional device" includes without limitation diagnostic devices (e.g., pressure transducers, conductivity measurement devices, temperature measurement devices, flow measurement devices, electro- and neuro-physiology mapping devices, material detection devices, imaging devices, central venous pressure (CVP) monitoring devices, intracardiac echocardiography (ICE) catheters, balloon sizing catheters, needles, biopsy tools), therapeutic devices (e.g., ablation catheters (e.g., radio-frequency, ultrasonic, optical), patent foramen ovale (PFO) closure devices, cryotherapy catheters, vena cava filters, stents, stent-grafts, septostomy tools), and agent delivery devices (e.g., needles, cannulae, catheters, elongated members). For purposes hereof, "agent" includes without limitation therapeutic agents, pharmaceuticals, chemical compounds, biologic compounds, genetic materials, dyes, saline, and contrast agents. The agent may be liquid, gel, solid, or any other appropriate form. Furthermore, the lumen may be used to deliver agents therethrough without the use of an interventional device. The combinative inclusion of a deflectable member and lumen for interventional device delivery therethrough facilitates multi-functionality of the catheter. This is advantageous because it reduces the number of catheters and access sites required during the procedure, provides the potential to limit the interventional procedure time, and enhances ease of use.

In this regard, in certain embodiments the lumen may be defined by an inside surface of the wall of the outer tubular body. In other embodiments, the lumen may be defined by an inside surface of an inner tubular body located within the outer tubular body and extending from the proximal end to the distal end thereof.

In another aspect, a deflectable member may be selectively deflectable through an arc of at least 45 degrees, and in various implementations at least 90 degrees. For example, the deflectable member may be deflectable in a pivot-like manner about a pivot, or hinge, axis through an arc of at least 90 degrees. Further, the deflectable member may be selectively deflectable and maintainable at a plurality of positions across a range of different angled positions. Such embodiments are particularly apt for implementing a deflectable member comprising an imaging device.

In certain embodiments, a deflectable imaging device may be selectively deflectable from an exposed (e.g., where at least a portion of the aperture of the deflectable imaging device is free from interference from the outer tubular body) side-looking first position to an exposed forward-looking, second position. "Side-looking" as used herein is defined as the position of the deflectable imaging device where the field of view of the deflectable imaging device is oriented substantially perpendicular to the distal end of the outer tubular body. "Forward-looking" includes where the imaging field of view of the deflectable imaging device is at least partially deflected to enable imaging of a volume that includes regions distal to the distal end of the catheter. For example, a deflectable imaging device (e.g., an ultrasound transducer array) may be aligned with (e.g., disposed parallel to or coaxially with) a center axis of the outer tubular body in a first position. Such an approach accommodates introduction into a vessel or body cavity and imaging of anatomical landmarks during catheter positioning (e.g., during insertion and advancement of the catheter into a vascular passageway or bodily cavity), wherein anatomical landmark images may be employed to precisely position an exit port of a lumen comprising the catheter. In turn, the ultrasound transducer array may be deflected from the side-looking, first position to a forward-looking, second position (e.g., angled at least 45 degrees, or in some applications at least 90 degrees) relative to a center axis of the catheter. An interventional device may then be selectively advanced through a lumen of the catheter and into a work area located adjacent to a lumen exit port and within an imaging field of view of the ultrasound transducer array, wherein imaged internal procedures may be completed utilizing the interventional device with imaging from the ultrasound transducer array alone or in combination with other imaging modalities (e.g., fluoroscopy). The deflectable imaging device may be deflected such that no part of the deflectable imaging device occupies a volume with the same cross section as the exit port and extending distally from the exit port. As such, the imaging field of view of the deflectable imaging device may be maintained in a fixed registration relative to the outer tubular body while the interventional device is being advanced through the outer tubular body, through the exit port, and into the imaging field of view of the deflectable imaging device.

In certain embodiments, a deflectable imaging device may be selectively deflectable from a side-looking first position to a rearward-looking, second position. "Rearward-looking" includes where the imaging field of view of the deflectable imaging device is at least partially deflected to enable imaging of a volume that includes regions proximal to the distal end of the catheter.

In a related aspect, a deflectable member may comprise an ultrasound transducer array having an aperture length at least as large as a maximum cross-dimension of the outer tubular body. Correspondingly, the deflectable ultrasound transducer array may be provided for selective deflection from a first position that accommodates advancement of the catheter through a vascular passageway to a second position that is angled relative to the first position. Again, in certain embodiments the second position may be selectively established by a user.

In a related aspect, deflectable member may be deflectable from a first position aligned with the center axis of the catheter (e.g., parallel thereto) to a second position angled relative to the center axis, wherein when in the second position the deflectable member is disposed outside of a working area located adjacent to a lumen exit port. As such, an interventional device may be advanceable through the exit port free from interference with the deflectable member.

In certain embodiments, the deflectable member may be provided so that the cross-sectional configuration thereof generally coincides with the cross-sectional configuration of the outer tubular body at the distal end thereof. For example, when a cylindrically-shaped outer tubular body is employed, a deflectable member may be located beyond the distal end of the outer tubular body and configured to coincide with (e.g., slightly exceed, occupy, or fit within) an imaginary cylindrical volume defined by and adjacent to such distal end, wherein the deflectable member is selectively deflectable out of such volume. Such an approach facilitates initial advancement and positioning of the catheter through vascular passageways.

In certain embodiments, a deflectable member may be provided to deflect along an arc path that extends away from a center axis of the outer tubular body. By way of example, in various implementations the deflectable member may be disposed to deflect from a first position that is located distal to a lumen exit port, to a second position that is lateral to the outer tubular body (e.g., to one side of the outer tubular body).

In another aspect, a deflectable member may be provided to deflect from a longitudinal axis of the catheter, wherein upon deflection a displacement arc is defined. In a catheter with a tip fixed relative to the outer tubular body, the displacement arc is the minimum curvature of the catheter. In a catheter with a deflectable member movable relative to the outer tubular body, the displacement arc is the minimum arc that is tangent to a face of the deflectable member and tangent to the center axis of the catheter. In the present aspect, a deflectable member may be provided wherein a ratio of a maximum cross-dimension of the distal end of the outer tubular body to the displacement arc radius is at least about 1. By way of example, for a cylindrical outer tubular body, the ratio may be defined by the outer diameter of the distal end of the outer tubular body over the displacement arc radius, wherein such ratio may be advantageously established to be at least about 1.

In another aspect, a deflectable member may be interconnected to the catheter body wall at the distal end of the outer tubular body. As will be further described, such interconnection may provide support functionality and/or selective deflection functionality. In the latter regard, the deflectable member may be deflectable about a deflection axis that is offset from a center axis of the outer tubular body. For example, the deflection axis may lie in a plane that extends transverse to the center axis of an outer tubular body and/or in a plane that extends parallel to the center axis. In the former regard, in one embodiment the deflection axis may lie in a plane that extends orthogonal to the center axis. In certain implementations, the deflection axis may lie in a plane that extends tangent to an exit port of a lumen that extends through the outer tubular body of the catheter.

In yet another aspect, the catheter may comprise a lumen for delivering an interventional device extending from the proximal end to an exit port located at the distal end of the outer tubular body, wherein the exit port has a center axis coaxially aligned with a center axis of the outer tubular body.

Such an arrangement facilitates the realization of relatively small catheter cross-dimensions, thereby enhancing catheter positioning (e.g., within small and/or tortuous vascular passageways). The deflectable member may also be disposed for deflection away from the coaxial center axes, thereby facilitating angled lateral positioning away from the initial catheter introduction (e.g., 0 degree) position of the deflectable member. In certain embodiments, the deflectable member may be deflectable through an arc of at least 90 degrees.

In a further aspect, the catheter may include an actuation device, extending from the proximal end to the distal end of the outer tubular body, wherein the actuation device may be interconnected to the deflectable member. Actuation devices may include devices selected from the group consisting of balloons, tether lines, pull wires, hypotubes, or stylets. The actuation device and outer tubular body may be disposed for relative movement such that the deflectable member is deflectable through an arc of at least 45 degrees in response to 0.5 cm or less relative movement between the actuation device and the outer tubular body. By way of example, in certain embodiments the deflectable member may be deflectable through an arc of at least 90 degrees in response to 1.0 cm or less relative movement of the actuation device and outer tubular body.

In a further aspect, the deflectable member may be interconnected to the outer tubular body. In one approach, the deflectable member may be supportably interconnected to the outer tubular body at the distal end thereof. In turn, an actuation device comprising one or more elongate members (e.g., of wire-like construction) may be disposed along the outer tubular body and interconnected at a distal end to the deflectable member, wherein upon applying a tensile force (e.g., a pull force) to a proximal end of the elongate member(s) the distal end of the elongate member(s) may cause the deflectable member to deflect. In this approach, the outer tubular body may define a lumen therethrough for delivering an interventional device extending from the proximal end of the outer tubular body to an exit port located distal to the proximal end.

In another approach, a deflectable member may be supportably interconnected to one of the outer tubular body and an actuation device, and restrainably interconnected by a restraining member (e.g., a ligature) to the other one of the outer tubular body and actuation device, wherein upon relative movement of the outer tubular body and actuation device the restraining member restrains movement of the deflectable member to affect deflection thereof.

For example, the deflectable member may be supportably interconnected to an actuation device and restrainably interconnected to the outer tubular body at the distal end thereof. In this approach, the actuation device may comprise an inner tubular body defining a lumen therethrough for delivering an interventional device extending from the proximal end of the catheter body to an exit port located distal to the proximal end.

More particularly, and in a further aspect, the catheter may comprise an inner tubular body, disposed within the outer tubular body for relative movement therebetween (e.g., relative slidable movement). A deflectable member located at the distal end may be supportably interconnected to the inner tubular body. In certain embodiments, the deflectable member may be disposed so that upon selective relative movement of the outer tubular body and inner tubular body the deflectable member is selectively deflectable and maintainable in a desired angular orientation.

For example, in one implementation an inner tubular body may be slidably advanced and retracted relative to an outer tubular body, wherein engagement between surfaces of the two components provides a mechanism interface sufficient to maintain a selected relative position of the two components and corresponding deflected position of the deflectable member. A proximal handle may also be provided to facilitate the maintenance of selected relative positioning of the two components.

In an additional aspect, the catheter may include an actuation device, extending from a proximal end to a distal end of the outer tubular body and moveable relative to the outer tubular body to apply a deflection force to the deflectable member. In this regard, the actuation device may be provided so that deflection force is communicated by the actuation device from the proximal end to the distal end in a balanced and distributed manner about a center axis of the outer tubular body. As may be appreciated, such balanced and distributed force communication facilitates the realization of a non-biased catheter yielding enhanced control and positioning attributes.

In conjunction with one or more of the above-noted aspects, the catheter may include a hinge that is supportably interconnected to the outer tubular body or, in certain embodiments, to an included actuation device (e.g., an inner tubular body). The hinge may be structurally separate from and fixedly interconnected to the catheter body (e.g., the outer tubular body or the inner tubular body). The hinge may be further fixedly interconnected to the deflectable member, wherein the deflectable member is deflectable in a pivot-like manner. The hinge member may be at least partially elastically deformable to deform from a first configuration to a second configuration upon the application of a predetermined actuation force, and to at least partially return from the second configuration to the first configuration upon removal of the predetermined actuation force. Such functionality facilitates the provision of a deflectable member that may be selectively actuated via an actuation device to move from an initial first position to a desired second position upon the application of a predetermined actuation force (e.g., a tensile or pulling force, or a compressive pushing force applied thereto), wherein upon selective release of the actuation force the deflectable member may automatically at least partially retract to its initial first position. In turn, successive deflectable positioning/retraction of the deflectable member may be realized during a given procedure, thereby yielding enhanced functionality in various clinical applications.

In certain embodiments, the hinge member may be provided to have a column strength sufficient to reduce unintended deflection of the deflectable member during positioning of the catheter (e.g., due to mechanical resistance associated with advancement of the catheter). By way of example, the hinge member may exhibit a column strength at least equivalent to that of the outer tubular body.

In certain implementations the hinge may be a portion of a one-piece, integrally defined member. For example, the hinge may comprise a shape memory material (e.g., Nitinol). In one approach, the hinge member may include a curved first portion and a second portion interconnected thereto, wherein the second portion is deflectable about a deflection axis defined by the curved first portion. By way of example, the curved first portion may comprise a cylindrically-shaped surface. In one embodiment, the curved first portion may include two cylindrically-shaped surfaces having corresponding center axes that extend in a common plane and intersect at an angle, wherein a shallow, saddle-like configuration is defined by the two cylindrically-shaped surfaces.

In yet a further aspect, the outer tubular body may be constructed to facilitate the inclusion of electrical componentry at the distal end thereof. More particularly, the outer tubular body may comprise a plurality of interconnected electrical conductors extending from the proximal end to the distal end. For example, in certain embodiments the electrical conductors may be interconnected in a ribbon-shaped member that is helically disposed about and along all or at least a portion of a catheter center axis, thereby yielding enhanced structurally qualities to the wall of the outer tubular body and avoiding excessive strain on the electrical conductors during flexure of the outer tubular body. For example, in certain embodiments the electrical conductors may be braided along at least a portion of the catheter center axis, thereby yielding enhanced structurally qualities to the wall of the outer tubular body. The outer tubular body may further include a first layer disposed inside of the first plurality of electrical conductors and extending from the proximal end to the distal end, and a second layer disposed on the outside of the first plurality of electrical conductors, extending from the proximal end to the distal end. The first tubular layer and second tubular layer may each be provided to have a dielectric constant of about 2.1 or less, wherein capacitive coupling may be advantageously reduced between the plurality of electrical conductors and bodily fluids present outside of the catheter and within a lumen extending through the outer tubular body.

In yet another aspect, a catheter may include a tubular body. The tubular body may include a wall with a proximal end and a distal end. The wall may include first and second layers extending from the proximal end to the distal end. The second layer may be disposed outside of the first layer. The first and second layers may each have a withstand voltage of at least about 2,500 volts AC. The wall may further include at least one electrical conductor extending from the proximal end to the distal end and disposed between the first and second layers. A lumen may extend through the tubular body. Combined, the first and second layers may provide an elongation resistance such that a tensile load of about 3 pound-force (lbf) (13 Newton (N)) results in no more than a 1 percent elongation of the tubular body.

In an arrangement, the tubular body may provide an elongation resistance such that a tensile load of about 3 lbf (13 N) applied to the tubular body results in no more than a 1 percent elongation of the tubular body, and in such an arrangement at least about 80 percent of the elongation resistance may be provided by the first and second layers.

In an embodiment, the first and second layers may have a combined thickness of at most about 0.002 inches (0.05 millimeters (mm)). Moreover, the first and second layers may have a combined elastic modulus of at least about 345,000 pounds per square inch (psi) (2,379 megapascal (MPa)). The first and second layers may exhibit a substantially uniform tensile profile about the circumference and along the length of the tubular body when a tensile load is applied to the tubular body. The first and second layers may each include helically wound material (e.g., film). For example, the first layer may include a plurality of helically wound films. A first portion of the plurality of films may be wound in a first direction, and a second portion of the films may be wound in a second direction that is opposite from the first direction. One or more of the plurality of films may include a high-strength tensilized film. One or more of the plurality of films may include non-porous fluoropolymer. The non-porous fluoropolymer may comprise non-porous ePTFE. The second layer may be constructed similarly to the first layer. The at least one electrical conductor may be in the form of a multiple conductor ribbon and/or conductive thin film and may be helically wrapped along at least a portion of the tubular body.

As will be appreciated, the construction of the tubular body of the current aspect may be utilized in other aspects described herein such as, for example, aspects where a tubular body is disposed within another tubular body and relative motion between the tubular bodies is used to deflect a deflectable member.

In an embodiment of the current aspect the first and second layers may have a combined thickness of at most about 0.010 inches (0.25 mm). Moreover, the first and second layers may have a combined elastic modulus of at least about 69,000 psi (475.7 MPa). In the present embodiment, the first layer may comprise a first sub-layer of the first layer and a second sub-layer of the first layer. The first sub-layer of the first layer is disposed inside the second sub-layer of the first layer. The second layer may comprise a first sub-layer of the second layer and a second sub-layer of the second layer. The first sub-layer of the second layer is disposed outside the second sub-layer of the first layer. The first sub-layer of the first layer and the first sub-layer of the second layer may include a first type of helically wound film. The second sub-layer of the first layer and the second sub-layer of the second layer may include a second type of helically wound film. The first type of helically wound film may include non-porous fluoropolymer and the second type of helically wound film may include porous fluoropolymer.

In another embodiment, the first layer may have a thickness of at most about 0.001 inches (0.025 mm) and the second layer may have a thickness of at most about 0.005 inches (0.13 mm). Moreover, the first layer may have an elastic modulus of at least about 172,500 psi (1,189 MPa) and the second layer may have an elastic modulus of at least about 34,500 psi (237.9 MPa).

In another aspect, the outer tubular body may comprise a plurality of electrical conductors extending from a proximal end to the distal end and a set of tubular layers inside and/or outside of the first plurality of electrical conductors. The set of tubular layers may comprise a low dielectric constant layer (e.g., located closest to the electrical conductors), and a high withstand voltage layer. In this regard, the low dielectric constant layer may have a dielectric constant of 2.1 or less, and the high withstand voltage layer may be provided to yield a withstand voltage of at least about 2500 volts AC. In certain embodiments, a set of low dielectric and high withstand voltage layers may be provided both inside and outside of the plurality of electrical conductors along the length of the outer tubular body.

In certain embodiments tie layers may be interposed between the electrical conductors and one or more inner and/or outer layers. By way of example, such tie layers may comprise a film material that may have a melt temperature that is lower than other components of the outer tubular body, wherein the noted layers of components may be assembled and the tie layers selectively melted to yield an interconnected structure. Such selectively melted tie layers may prevent other layers of the outer tubular body from migrating relative to each other during manipulation of the outer tubular body (e.g., during insertion into a patient).

For some arrangements, the outer tubular body may further include a shielding layer disposed outside of the electrical conductors. By way example, the shielding layer may be provided to reduce electromagnetic interference (EMI) emissions from the catheter as well as shield the catheter from external EMI.

In certain embodiments, lubricious inside and outside layers and/or coatings may also be included. That is, an inner layer may be disposed within the first tubular layer and an outer layer may be disposed outside of the second tubular layer.

In yet a further aspect, the catheter may be provided to comprise a first electrical conductor portion extending from a proximal end to a distal end of the catheter, and a second electrical conductor portion electrically interconnected to the first electrical conductive portion at the distal end. The first electrical conductor portion may comprise a plurality of interconnected electrical conductors arranged side-by-side with electrically non-conductive material therebetween. In certain implementations, the first electrical conductor portion may be helically disposed about a catheter center axis from the proximal end to the distal end thereof. In conjunction with such implementations, the second electrical conductor portion may comprise a plurality of electrical conductors interconnected to the plurality of interconnected electrical conductors of the first electrical conductor portion, and extending parallel to a center axis of the outer tubular body at the distal end. In certain embodiments, the first electrical conductor portion may be defined by a ribbon-shaped member included within the wall of the outer tubular body, thereby contributing to the structural integrity thereof.

In conjunction with the noted aspect, the first electrical conductor portion may define a first width across the interconnected plurality of electrical conductors, and the second electrical conductor portion may define a second width across the corresponding plurality of electrical conductors. In this regard, the second electrical conductor portion may be defined by electrically conductive traces disposed on a substrate. By way of example, the substrate may extend between the end of the first electrical conductor portion and electrical componentry provided at the distal end of a catheter, including for example an ultrasound transducer array.

In various embodiments, the second electrical conductor portion may be interconnected to a deflectable member and may be of a bendable construction, wherein at least a portion of the second electrical conductor portion is bendable with and in response to deflection of the deflectable member. More particularly, the second electrical conductor portion may be defined by electrically conductive traces on a substrate that is bendable in tandem with a deflectable member through an arc of at least 90 degrees.

In a further aspect, the catheter may comprise a deflectable member that includes an ultrasound transducer array, wherein at least a portion of the deflectable ultrasound transducer array may be located within the outer tubular body wall at the distal end. Further, the catheter may include a lumen for delivering an interventional device extending from the proximal end to a point distal thereto.

In a still further aspect, the catheter may comprise a steerable or pre-curved catheter segment located near the distal end of the outer tubular body and the deflectable member may comprise an ultrasound transducer array. Further, the catheter may include a lumen for delivering an interventional device extending from the proximal end to a point distal thereto.

In another aspect, the catheter may comprise an outer tubular body having a wall, a proximal end and a distal end. The catheter may further include a lumen for delivering an interventional device extending through the outer tubular body from the proximal end to an exit port located distal to the proximal end. The catheter may further include a first electrical conductor portion comprising a plurality of interconnected electrical conductors arranged side-by-side with electrically non-conductive material therebetween. The first electrical conductor portion may extend from the proximal end to the distal end. The catheter may further include a second electrical conductor portion electrically interconnected to the first electrical conductor portion at the distal end. The second electrical conductor portion may comprise a plurality of electrical conductors. The catheter may further include a deflectable member located at the distal end. The second electrical conductor portion may be electrically interconnected to the deflectable member and may be bendable in response to deflection of the deflectable member.

In another aspect, the catheter may comprise an outer tubular body having a wall, a proximal end and a distal end. The catheter may further include a lumen for delivering an interventional device or agent delivery device extending through the outer tubular body from the proximal end to an exit port located distal to the proximal end. The catheter may further include a deflectable member, at least a portion of which is permanently located outside of the outer tubular body at the distal end, selectively deflectable relative to the outer tubular body and distal to the exit port. In an embodiment, the catheter may further include a hinge located at the distal end where the deflectable member may be supportably interconnected to the hinge. In such an embodiment, the deflectable member may be selectively deflectable relative to the outer tubular body about a hinge axis defined by the hinge.

Numerous aspects described hereinabove comprising a selectively deflectable imaging device disposed at a distal end of an outer tubular body of a catheter. Additional aspects of the present invention may include deflectable members in place of such deflectable imaging devices. Such deflectable members may include imaging devices, diagnostic devices, therapeutic devices, or any combination thereof.

In another aspect, a method is provided for operating a catheter having a deflectable imaging device located at a distal end thereof. The method may include moving the distal end of the catheter from an initial position to a desired position and obtaining image data from the deflectable imaging device during at least a portion of the moving step. The deflectable imaging device may be located in a first position during the moving step. The method may further include utilizing the image data to determine when the catheter is located at the desired position, deflecting the deflectable imaging device from the first position to a second position after the moving step; and advancing an interventional device through an exit port at the distal end of the catheter and into an imaging field of view of the deflectable imaging device in the second position.

In an arrangement, the deflecting step may further include translating a proximal end of at least one of an outer tubular body of the catheter and actuation device of the catheter relative to a proximal end of the other one of the outer tubular body and actuation device.

A deflection force may be applied to a hinge in response to the translating step. The deflectable imaging device may be supportably interconnected by the hinge to one of the outer tubular body and the actuation device. The deflection force may be initiated in response to the translating step. The deflection force may be communicated in a balanced and distributed manner about a center axis of the outer tubular body. Communicating the deflection force in such a manner may reduce undesirable bending and/or whipping of the catheter.

In an arrangement, the position of the deflectable imaging device may be maintained relative to the distal end of the catheter during the moving and obtaining steps. In an embodiment, the deflectable imaging device may be side-looking in the first position and forward-looking in the second position. In an embodiment, the imaging field of view may be maintained in a substantially fixed registration relative to the distal end of the catheter during the advancing step.

The various features discussed above in relation to each aforementioned aspect may be utilized by any of the aforementioned aspects. Additional aspects and corresponding

BRIEF DESCRIPTION OF THE DRAWINGS

FIG. 2A shows a cross-sectional view of the catheter embodiment of FIG. 1.

FIG. 2B shows a catheter embodiment having a deflectable ultrasound transducer array located at a distal end of the catheter.

FIGS. 5B through 5E show an embodiment of a catheter that includes a deflectable member wherein the deflectable member is deflectable by moving an inner tubular body relative to an outer tubular body.

FIG. 5F shows an embodiment of an electrical interconnection between a helically disposed electrical interconnection member and a flexible electrical member.

FIGS. 10A and 10B demonstrate further alternative embodiments.

FIGS. 11, 11A and 11B demonstrate further embodiments.

DETAILED DESCRIPTION OF THE DRAWINGS

Figure 1:
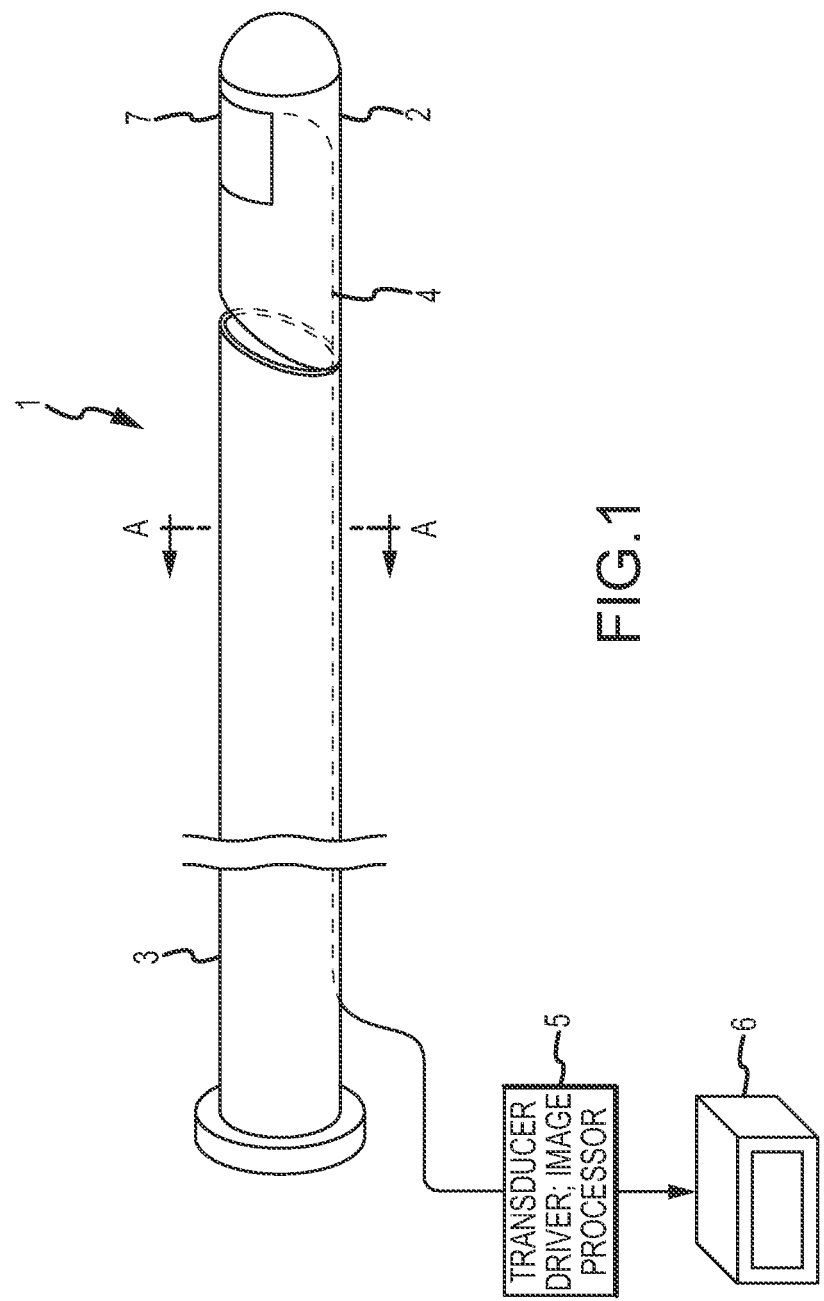
FIG. 1 shows a catheter embodiment having a deflectable ultrasound transducer array located at an end of the catheter.

The detailed description that follows is directed to various catheter embodiments that include a deflectable member that comprises an ultrasound transducer array, and a lumen for delivering an interventional device. Such embodiments are for exemplarily purposes and are not intended to limit the scope of the present invention. In that regard, the deflectable member may comprise componentry other than or in addition to an ultrasound transducer array. Further, additional embodiments may utilize inventive features described herein that do not necessitate the inclusion of a lumen.

An ultrasound transducer array built into a catheter presents unique design challenges. Two critical points include, for example, the resolution in the image plane and the ability to align that image plane with an interventional device.

The resolution in the imaging plane of an ultrasound array can be approximated by the following equation:

Lateral resolution=Constant*wavelength*Image Depth/Aperture Length

For catheters being described here, the wavelength is typically in the range of 0.2 mm (at 7.5 MHz). The constant is in the range of 2.0. The ratio of (Image Depth/Aperture Length) is a critical parameter. For ultrasound imaging in the range of 5-10 MHz for catheters presented here, acceptable resolution in the imaging plane can be achieved when this ratio is in the range of 10 or less.

For imaging with a catheter in the major vessels and the heart, it is desirable to image at depths of 70 to 100 mm. Catheters used in the heart and major vessels are typically 3 to 4 mm in diameter or smaller. Thus while conceptually a transducer array can be made of arbitrary size and placed at any position within the catheter body, this model shows that transducer arrays that readily fit within the catheter structure do not have sufficient width for acceptable imaging.

The ultrasound image plane produced by the array placed on the catheter typically has a narrow width normally referred to as the out of plane image width. For objects to be seen in the ultrasound image, it is important that they be in this image plane. When a flexible/bendable catheter is placed in a major vessel or heart, the image plane can be aligned to some degree. It is desirable to guide a second device placed in the body with the ultrasound image, but doing so requires placing that second device in the plane of the ultrasound image. If the imaging array and the interventional device are both on flexible/bendable catheters that are inserted into the body, it is extremely difficult to orient one interventional device into the ultrasound image plane of the imaging catheter.

Certain embodiments of the present invention utilize an ultrasound image to guide an interventional device. To accomplish this, a large enough aperture is needed to produce an image of acceptable resolution while being able to place the device in a known position that is stable relative to the imaging array and/or to be able to align and/or register the interventional device to the ultrasound image plane.

In certain implementations, the aperture length of the ultrasound array may be larger than the maximum cross dimension of the catheter. In certain implementations, the aperture length of the ultrasound array may be much larger (2 to 3 times larger) than the diameter of the catheter. This large transducer, however, may fit within the 3 to 4 mm maximum diameter of the catheter to be inserted into the body. Once in the body, the imaging array is deployed out of the catheter body leaving space to pass an interventional device through that same catheter that will then be located in a known position relative to the imaging array. In certain arrangements, the imaging array may be deployed in a way so that the interventional device can be readily kept within the ultrasound image plane.

The catheter may be configured for delivery through a skin puncture at a remote vascular access site (e.g., vessel in the leg). Through this vascular access site, the catheter may be introduced into regions of the cardiovascular system such as the inferior vena cava, heart chambers, abdominal aorta, and thoracic aorta.

Positioning the catheter in these anatomic locations provides a conduit for delivery of devices or therapy to specific target tissues or structures. One example of this includes bedside delivery of inferior vena cava filters in patients for whom transport to the catheterization laboratory is either high risk or otherwise undesirable. The catheter with the ultrasound transducer array allows the clinician to not only identify the correct anatomical location for placement of the inferior vena cava filter, but also provides a lumen through which the vena cava filter can be delivered under direct ultrasound visualization. Both location identification and delivery of a device can occur without withdrawal or exchange of the catheter and/or imaging device. In addition, post-delivery visualization of the device allows the clinician to verify placement location and function(s) prior to removal of the catheter.

Another application of such a catheter is as a conduit through which ablation catheters can be delivered within the atria of the heart. Although ultrasound imaging catheters are utilized today in many of these cardiac ablation procedures, it is very difficult to achieve proper orientation of the ablation catheters and ultrasound catheter so as to attain adequate visualization of the ablation site. The catheter described herein provides a lumen through which the ablation catheter can be directed and the position of the ablation catheter tip monitored under direct ultrasound visualization. As described, the coaxial registration of this catheter and other interventional devices and therapy delivery systems provides the means by which direct visualization and control can be achieved.

Turning now to the figures, FIG. 1 shows a catheter embodiment having an ultrasound transducer array 7 located on a deflectable distal end of the catheter 1. Specifically, catheter 1 comprises a proximal end 3 and a distal end 2. Located on the distal end 2 is the ultrasound transducer array 7. Attached to ultrasound transducer array 7 is at least one electrically conductive wire 4 (such as a microminiature flat cable) that extends from the array 7 to the proximal end 3 of catheter 1. The at least one electrically conductive wire 4 exits the catheter proximal end 3 through a port or other opening in the catheter wall and is electrically connected to transducer driver; image processor 5 which provides a visual image via device 6. Such an electrical connection may include a continuous conduction path through a conductor or series of conductors. Such an electrical connection may include an inductive element, such as an isolation transformer. Where appropriate, other electrical interconnections discussed herein may include such inductive elements.

FIG. 2A is a cross-section of FIG. 1 taken along lines A-A. As can be seen in FIG. 2A, the catheter 1 includes a catheter wall portion 12 that extends at least the length of proximal end 3 and further defines lumen 10 that extends at least the length of proximal end 3. Catheter wall 12 can be any suitable material or materials, such as extruded polymers, and can comprise one or more layers of materials. Further shown is the at least one electrically conductive wire 4 located at the bottom portion of wall 12.

Operation of the catheter 1 can be understood with reference to FIGS. 1 and 2B. Specifically, the catheter distal end 2 can be introduced into the desired body lumen and advanced to a desired treatment site with ultrasound transducer array 7 in a "side-looking" configuration (as shown in FIG. 1). Once the target area is reached, interventional device 11 can be advanced through the lumen 10 of the catheter 1 and out the distal port 13 and advanced in a distal direction. As can be seen, the catheter 1 can be configured such that advancing interventional device 11 in a distal direction out distal port 13 can deflect distal end 2 and thus result in ultrasound transducer array 7 being converted from "side-looking" to "forward-looking". Thus, the physician can advance interventional device 11 into the field of view of ultrasound transducer array 7.

"Deflectable" is defined as the ability to move the ultrasound transducer array, or a portion of the catheter body containing the ultrasound transducer array, away from the longitudinal axis of the catheter body, preferably such that 1) the transducer face is fully or partially forward facing or rearward facing, and 2) the distal exit port of the delivery lumen and the catheter body can be opened. Deflectable can include 1) "actively deflectable" meaning that the array or catheter portion containing the array can be moved by remote application of force (e.g., electrical (e.g., wired or wireless), mechanical, hydraulic, pneumatic, magnetic, etc.), transmission of that force by various means including pull wires, hydraulic lines, air lines, magnetic coupling, or electrical conductors; and 2) "passively deflectable" meaning that the array or catheter portion containing the array when in the resting, unstrained condition, tends to be in alignment with the catheter longitudinal axis and may be moved by local forces imparted by the introduction of interventional device 11.

Figure 2C:
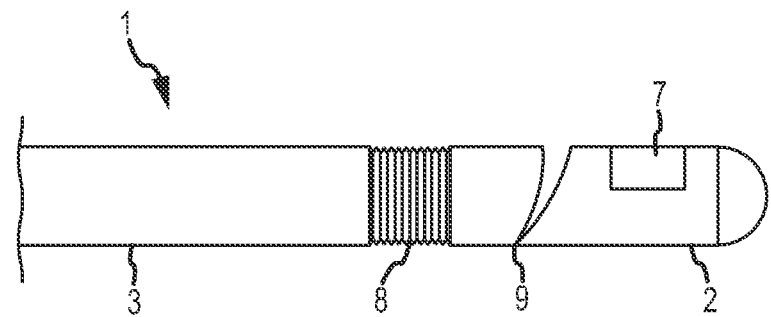
FIGS. 2C and 2D show the catheter embodiment of FIGS. 2A and 2B, wherein the catheter further includes an optional steerable segment.

In certain embodiments, the ultrasound transducer array may be deflected up to 90 degrees from the longitudinal axis of the catheter, as shown in FIG. 2B. Moreover, the deflectable ultrasound transducer array 7 can be attached to the catheter by a hinge 9 as shown in FIG. 2C. In an embodiment, hinge 9 can be a spring-loaded hinged device. Such a spring-loaded hinge can be actuated from the proximal end of the catheter by any suitable means. In an embodiment, the spring-loaded hinge is a shape memory alloy actuated by withdrawal of an outer sheath.

Figure 2D:
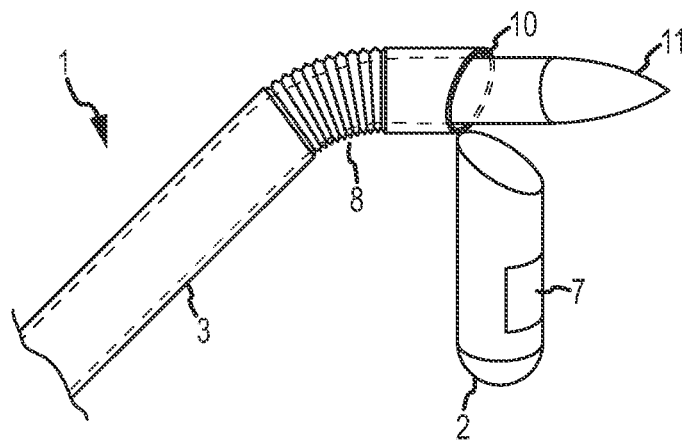

With reference to FIGS. 2C and 2D, the catheter 1 can further comprise a steerable segment 8. "Steerable" is defined as the ability to direct the orientation of the portions of the catheter 1 and lumen 10 distal to the steerable segment at an angle with respect to the catheter proximal to the steerable segment. FIG. 2D shows the steerable segment 8 deflected at an angle with respect to the catheter proximal to the steerable segment.

Figure 3A:
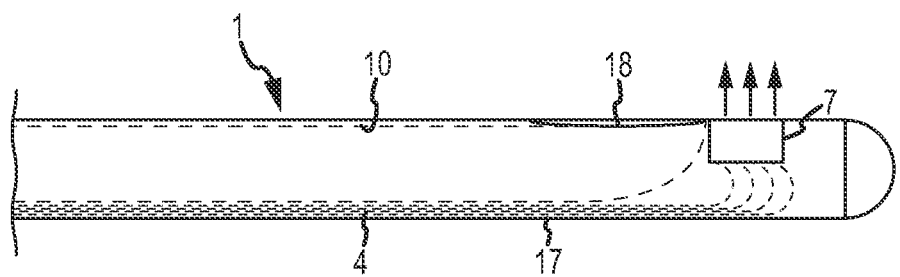
FIGS. 3A through 3D show further catheter embodiments having a deflectable ultrasound transducer array located at a distal end of the catheter.
Figure 3B:
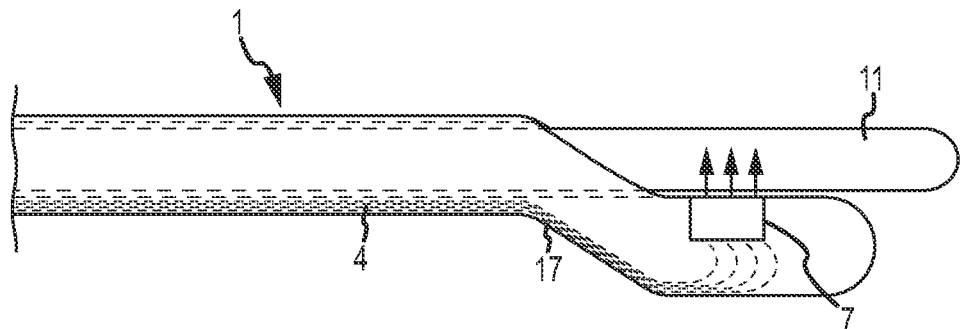

In a further embodiment, FIGS. 3A and 3B demonstrate a catheter 1 including an ultrasound transducer array 7 on a deflectable distal end 17 of the catheter 1. The catheter 1 comprises a proximal end (not shown) and a deflectable distal end 17. Ultrasound transducer array 7 is located at the deflectable distal end 17. Conductive wires 4 are attached to the ultrasound transducer array 7 and extend in a proximal direction to the proximal end of catheter 1. The catheter 1 also includes a generally centrally located lumen 10 that extends from the proximal end to the distal tip of the catheter. At distal end 17, the generally centrally located lumen 10 is essentially blocked or closed off by ultrasound transducer array 7. Finally, the catheter 1 also includes at least one longitudinally extending slit 18 that extends through a region proximal to the ultrasound transducer array 7.

As can be seen in FIG. 3B, once interventional device 11 is advanced distally through lumen 10, the interventional device 11 deflects deflectable distal end 17 and ultrasound transducer array 7 in a downward motion, thus opening lumen 10 so that interventional device 11 may be advanced distally past the ultrasound transducer array 7.

Figure 3C:
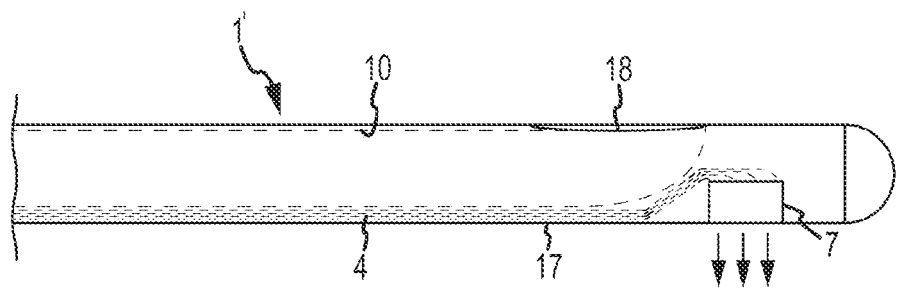

FIG. 3C illustrates a catheter 1' that is an alternate configuration of the catheter 1 of FIGS. 3A and 3B. The catheter 1' is configured the same as the catheter 1 with an exception that the ultrasound imaging array 7 is oriented such that it is operable to image a volume on a side of the catheter 1' opposite from the longitudinally extending slit 18 (e.g., in a direction opposite from the ultrasound imaging array 7 of FIGS. 3A and 3B). This may be beneficial, for example, to maintain registration with a fixed anatomical landmark as the interventional device 11 is deployed.

Figure 3D:
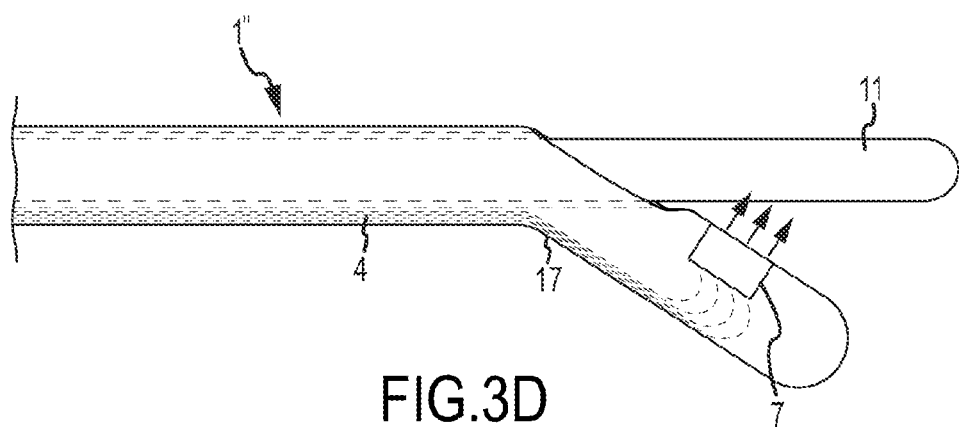

FIG. 3D illustrates a catheter 1" that is a variation of the catheter 1 of FIGS. 3A and 3B. The catheter 1" is configured such that the ultrasound imaging array 7 pivots to a partially forward-looking position when the interventional device 11 is advanced through the longitudinally extending slit 18. The ultrasound imaging array 7 of catheter 1" may be oriented as illustrated or it may be oriented to image in an opposite direction (similar to the ultrasound imaging array 7 of catheter 1'). In additional embodiments (not shown), a catheter similar to catheter 1 may include multiple imaging arrays (e.g., occupying the positions shown in both FIGS. 3A and 3C).

In various embodiments described herein, catheters may be provided having an ultrasound transducer array located near the distal end thereof. The catheter body may comprise a tube having a proximal end and a distal end. Moreover, the catheter may have at least one lumen extending from the proximal end to at least near the ultrasound transducer array. The catheter may comprise electrically conductive wires (e.g., a microminiature flat cable) attached to the ultrasound transducer array and being imbedded in the catheter wall and helically extending from the ultrasound transducer array to the proximal end of the catheter.

Figure 4:
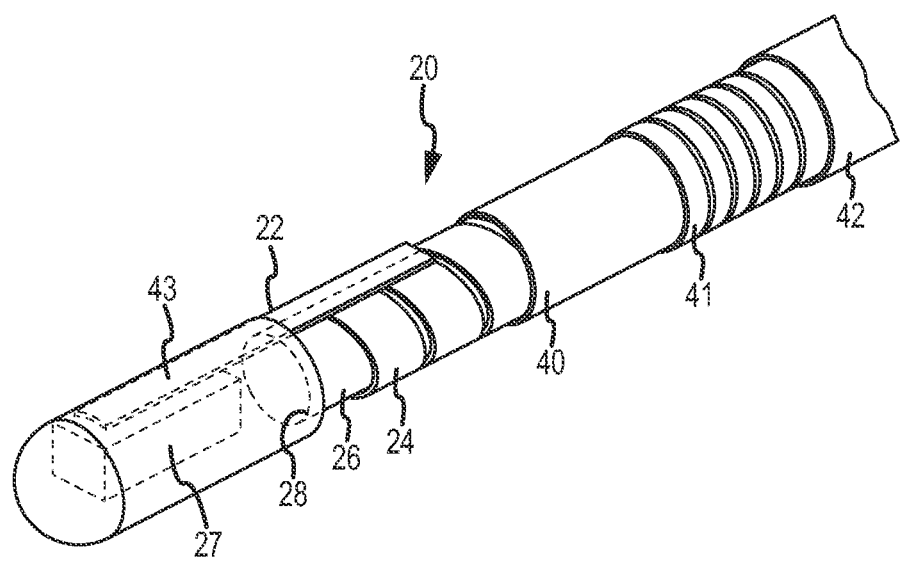
FIG. 4 shows a catheter embodiment having electrically conductive wires attached to an ultrasound transducer array located near the distal end of the catheter, wherein the electrically conductive wires helically extend to the proximal end of the catheter and are embedded in the catheter wall.
Figure 4A:
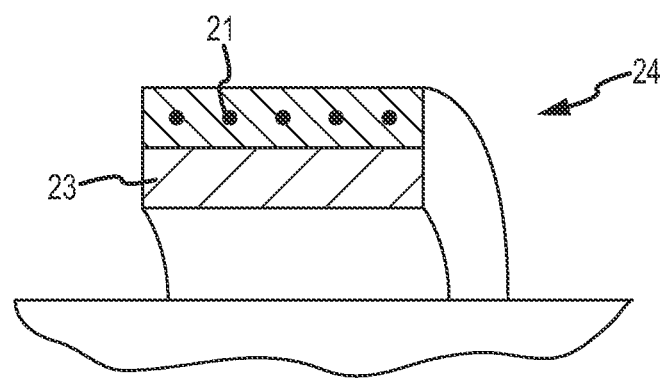
FIG. 4A shows an exemplary conductive wire assembly.

Such a catheter is depicted, for example, in FIGS. 4 and 4A. Specifically, FIGS. 4 and 4A demonstrate catheter 20 having a proximal end (not shown) and a distal end 22 with ultrasound transducer array 27 located at the distal end 22 of catheter 20. As can be seen, lumen 28 is defined by the inner surface of polymer tube 26, which can be formed from a suitable lubricious polymer (such as, for example, PEBAX® 72D, PEBAX® 63D, PEBAX® 55D, high density polyethylene, polytetrafluoroethylene, and expanded polytetrafluoroethylene, and combinations thereof) and extends from the proximal end to the distal end 22 near the ultrasound transducer array 27. The electrically conductive wires (e.g., microminiature flat cable) 24 are helically wrapped about polymer tube 26 and extend from near the ultrasound transducer array 27 proximally to the proximal end. An example of a suitable microminiature flat cable is shown in FIG. 4A where microminiature flat cable 24 includes electrically conductive wires 21 and suitable ground, such as copper 23. A conductive circuit element 43 (such as a flexboard) is attached to ultrasound transducer array 27 and to the electrically conductive wires 24. A suitable polymer film layer 40 (such as a lubricious polymer and or shrink wrap polymer) can be located over electrically conductive wires 24 to act as an insulating layer between the electrically conductive wires 24 and a shielding layer 41. Shielding layer 41 may comprise any suitable conductor that can be helically wrapped over polymer film 40, for example, in the opposing direction of the electrically conductive wires 21. Finally, outer jacket 42 can be provided over shielding layer 41 and can be of any suitable material, such as a lubricious polymer. Suitable polymers include, for example, PEBAX® 70D, PEBAX® 55D, PEBAX® 40D, and PEBAX® film 23D. The catheter depicted in FIGS. 4 and 4A can include the deflectable distal end and steerable segments discussed above.

The above catheter provides a means to electrically interface with an ultrasound probe at the distal end of a catheter while providing a working lumen to facilitate delivery of interventional devices to the imaged area. The construction of the catheter utilizes the conductors both to power the array as well as to provide mechanical properties that enhance kink resistance and torqueability. The novel construction presented provides a means to package the conductors and necessary shielding in a thin wall, thus providing a sheath profile that is suited for interventional procedures, with an OD targeted at or below 14 French (Fr) and an ID targeted at above 8 Fr, thus facilitating delivery of typical ablation catheters, filter delivery systems, needles, and other common interventional devices designed for vascular and other procedures.

Figure 5A:
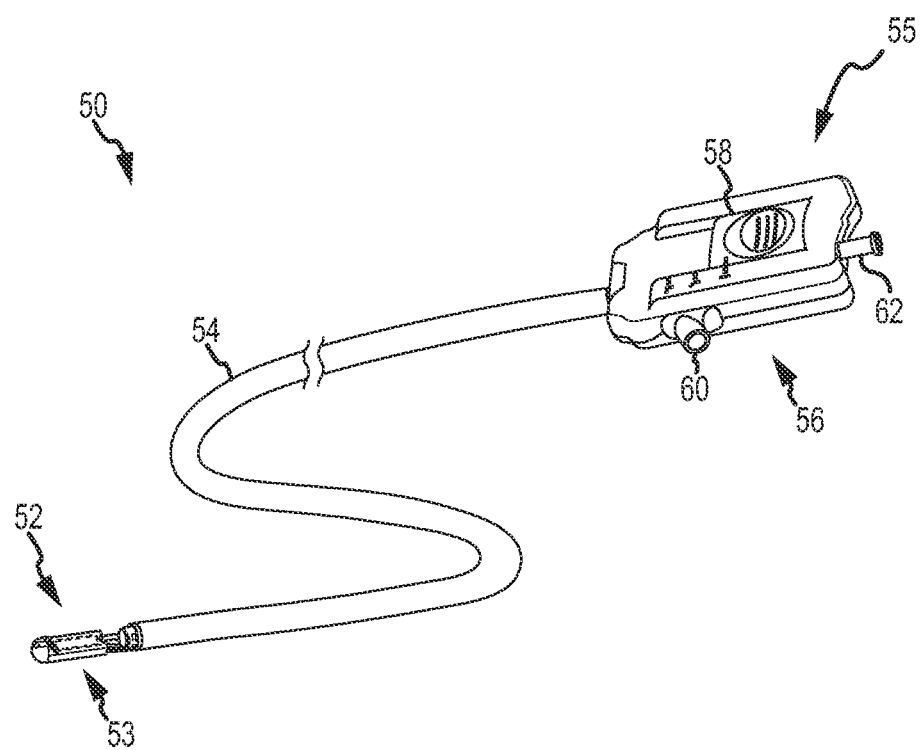
FIG. 5A shows an embodiment of a catheter that includes a deflectable member.

FIG. 5A shows an embodiment of a catheter 50 that includes a deflectable member 52 and a catheter body 54. The catheter body 54 may be flexible and capable of bending to follow the contours of a body vessel into which it is being inserted. The deflectable member 52 may be disposed at a distal end 53 of the catheter 50. The catheter 50 includes a handle 56 that may be disposed at a proximal end 55 of the catheter 50. During a procedure where the deflectable member 52 is inserted into the body of a patient, the handle 56 and a portion of the catheter body 54 remain outside of the body. The user (e.g., physician, technician, interventionalist) of the catheter 50 may control the position and various functions of the catheter 50. For example, the user may hold the handle 56 and manipulate a slide 58 to control a deflection of the deflectable member 52. In this regard, the deflectable member 52 may be selectively deflectable. The handle 56 and slide 58 may be configured such that the position of the slide 58 relative to the handle 56 may be maintained, thereby maintaining the selected deflection of the deflectable member 52. Such maintenance of position may at least partially be achieved by, for example, friction (e.g., friction between the slide 58 and a stationary portion of the handle 56), detents, and/or any other appropriate means. The catheter 50 may be removed from the body by pulling (e.g., pulling the handle 56).

Furthermore, the user may insert an interventional device (e.g., a diagnostic device and/or therapeutic device) through an interventional device inlet 62. The user may then feed the interventional device through the catheter 50 to move the interventional device to the distal end 53 of the catheter 50. Electrical interconnections between an image processor and the deflectable member may be routed through an electronics port 60 and through the catheter body 54 as described below.

FIGS. 5B through 5E show an embodiment of a catheter that includes a deflectable member 52 wherein the deflectable member 52 is deflectable by moving an inner tubular body 80 relative to an outer tubular body 79 of the catheter body 54. As shown in FIG. 5B, the illustrated deflectable member 52 includes a tip 64. The tip 64 may encase various components and members.

The tip 64 may have a cross section that corresponds to the cross section of the outer tubular body 79. For example, and as illustrated in FIG. 5B, the tip 64 may have a rounded distal end 66 that corresponds to the outer surface of the outer tubular body 79. The portion of the tip 64 that houses the ultrasound transducer array 68 may be shaped to at least partially correspond (e.g., along the lower outer surface of the tip 64 as viewed in FIG. 5B) to the outer surface of the outer tubular body 79. At least a portion of the tip 64 may be shaped to promote transport through internal structures of the patient such as the vasculature. In this regard, the rounded distal end 66 that may aid in moving the deflectable member 52 through the vasculature. Other appropriate end shapes may be used for the shape of the distal end 66 of the tip 64.

Figure 5C:
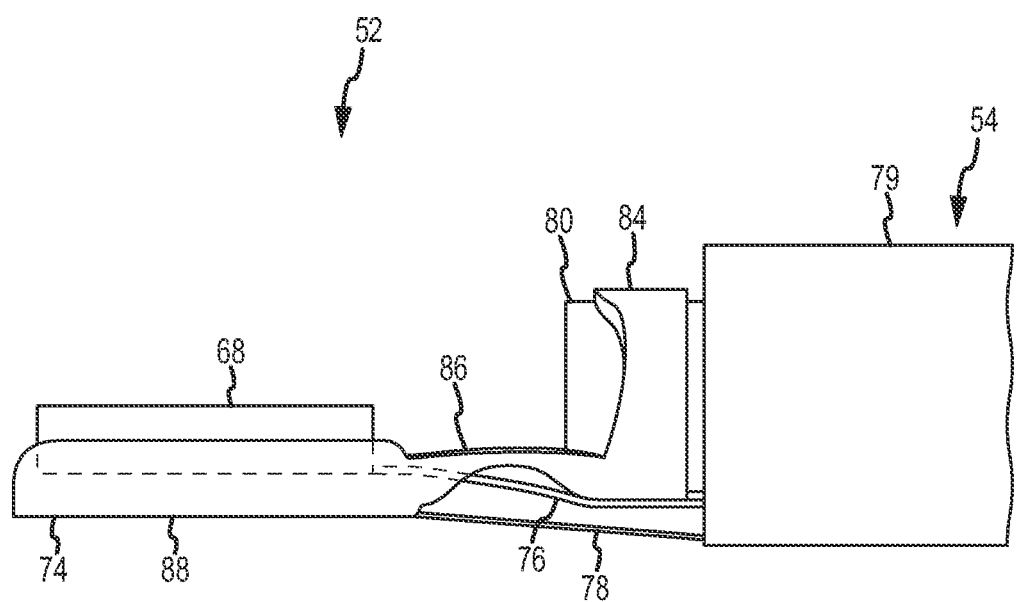
Figure 5D:
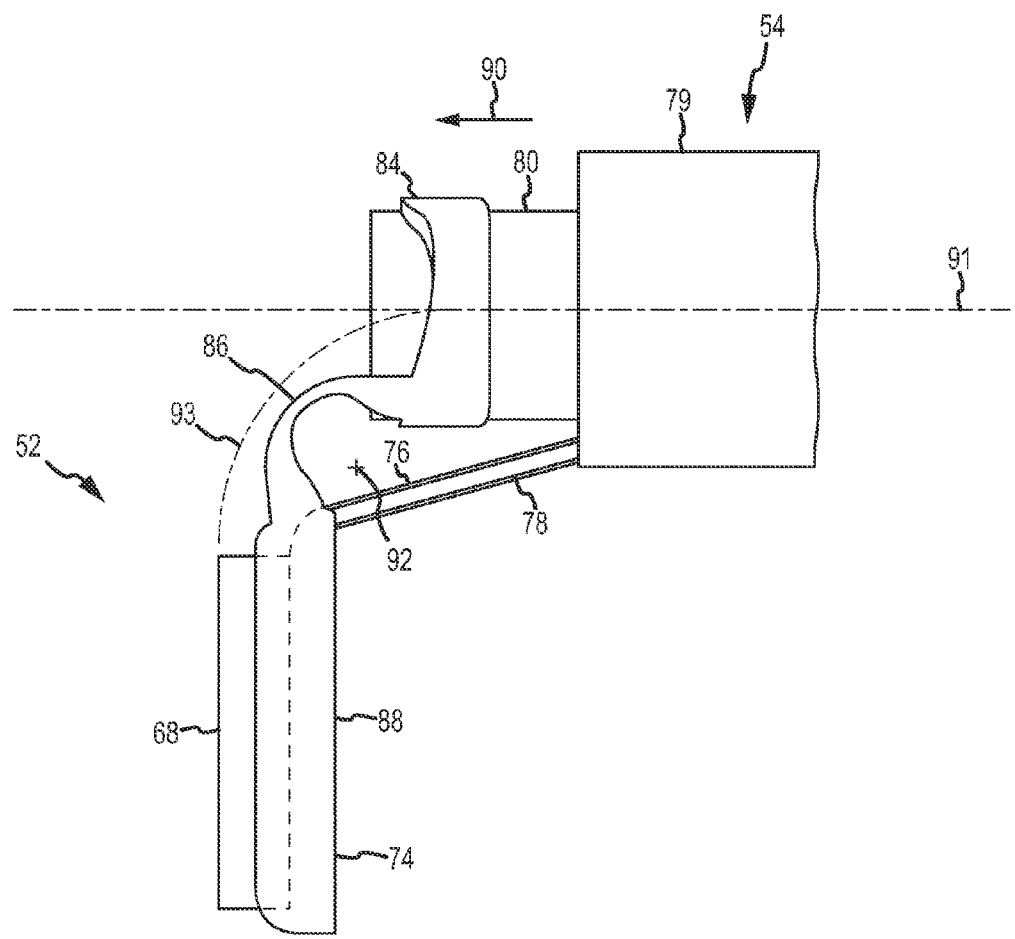

In an embodiment, such as the one illustrated in FIGS. 5B through 5D, the tip 64 may hold an ultrasound transducer array 68. As will be appreciated, as illustrated in FIG. 5B, the ultrasound transducer array 68 may be side-looking when the deflectable member 52 is aligned with the outer tubular body 79. The field of view of the ultrasound transducer array 68 may be located perpendicular to the flat upper face (as oriented in FIG. 5B) of the ultrasound transducer array 68. As illustrated in FIG. 5B, the field of view of the ultrasound transducer array 68 may be unobstructed by the outer tubular body 79 when the ultrasound transducer array 68 is side-looking. In this regard, the ultrasound transducer array 68 may be operable to image during catheter body 54 positioning, thereby enabling imaging of anatomical landmarks to aid in positioning the distal end of a lumen 82. The ultrasound transducer array 68 may have an aperture length. The aperture length may be greater than a maximum cross dimension of the outer tubular body 79. At least a portion of the deflectable member 52 may be permanently positioned distal to the distal end of the outer tubular body 79. In an embodiment, the entirety of the deflectable member 52 may be permanently positioned distal to the distal end of the outer tubular body 79. In such an embodiment, the deflectable member may be incapable of being positioned within the outer tubular body 79.

The tip 64 may further include a feature to enable the catheter to follow a guide wire. For example, as illustrated in FIG. 5B, the tip 64 may include a distal guide wire aperture 70 functionally connected to a proximal guide wire aperture 72. In this regard, the catheter may be operable to travel along the length of a guide wire threaded through the distal 70 and proximal 72 guide wire apertures.

As noted, the deflectable member 52 may be deflectable relative to the outer tubular body 79. In this regard, the deflectable member 52 may be interconnected to one or more members to control the motion of the deflectable member 52 as it is being deflected. A tether 78 may interconnect the deflectable member 52 to the catheter body 54. The tether 78 may be anchored to the deflectable member 52 on one end and to the catheter body 54 on the other end. The tether 78 may be configured as a tensile member operable to prevent the anchor points from moving a distance away from each other greater than the length of the tether 78. In this regard, through the tether 78, the deflectable member 52 may be restrainably interconnected to the outer tubular body 79.

An inner tubular body 80 may be disposed within the outer tubular body 79. The inner tubular body 80 may include the lumen 82 passing through the length of the inner tubular body 80. The inner tubular body 80 may be movable relative to the outer tubular body 79. This movement may be actuated by movement of the slide 58 of FIG. 5A. A support 74 may interconnect the deflectable member 52 to the inner tubular body 80. The support 74 may be structurally separate from the inner tubular body 80 and the outer tubular body 79. A flexboard 76 may contain electrical interconnections operable to electrically connect the ultrasound transducer array 68 to an electrical interconnection member 104 (shown in FIG. 5E) disposed within the outer tubular body 79. The exposed portion of flexboard 76 between the tip 64 and the outer tubular body 79 may be encapsulated to isolate it from possible contact with fluids (e.g., blood) when the deflectable member 52 is disposed within a patient. In this regard, the flexboard 76 may be encapsulated with an adhesive, a film wrap, or any appropriate component operable to isolate the electrical conductors of the flexboard 76 from the surrounding environment. In an embodiment, the tether 78 may be wrapped around the portion of the flexboard 76 between the tip 64 and the outer tubular body 79.

Deflection of the deflectable member 52 will now be discussed with reference to FIGS. 5C and 5D. FIGS. 5C and 5D illustrate the deflectable member 52 with the portion of the tip 64 surrounding the ultrasound image array 68 and support 74 removed. As illustrated in FIG. 5C, the support 74 may include a tubular body interface portion 84 operable to fix the support 74 to the inner tubular body 80. The tubular body interface portion 84 may be fixed to the inner tubular body 80 in any appropriate manner. For example, the tubular body interface portion 84 may be secured to the inner tubular body 80 with an external shrink wrap. In such a configuration, the tubular body interface portion 84 may be placed over the inner tubular body 80 and then a shrink-wrap member may be placed over the tubular body interface portion 84. Heat may then be applied causing the shrink wrap material to shrink and fix the tubular body interface portion 84 to the inner tubular body 80. An additional wrap may then be applied over the shrink wrap to further fix the tubular body interface portion 84 to the inner tubular body 80. In another example, the tubular body interface portion 84 may be secured to the inner tubular body 80 with an adhesive, a weld, fasteners, or any combination thereof. In another example, the tubular body interface portion 84 may be secured to the inner tubular body 80 as part of the assembly process used to build the inner tubular body 80. For example, the inner tubular body 80 may be partially assembled, the tubular body interface portion 84 may be positioned around the partially assembled inner tubular body 80, and then the inner tubular body 80 may be completed, thus capturing the tubular body interface portion 84 within a portion of the inner tubular body 80.

The support 74 may comprise, for example, a shape memory material (e.g., a shape memory alloy such as Nitinol). The support 74 may further include a hinge portion 86. The hinge portion 86 may comprise one or more members interconnecting the tubular body interface portion 84 with a cradle portion 88. The hinge portion 86, as illustrated in FIGS. 5B through 5C, may comprise two members. The cradle portion 88 may support the ultrasound transducer array 68. The support 74, including the hinge portion 86, may possess a column strength adequate to keep the deflectable member 52 substantially aligned with the outer tubular body 79 in the absence of any advancement of the inner tubular body 80 relative to the outer tubular body 79. In this regard, the deflectable member 52 may be operable to remain substantially aligned with the outer tubular body 79 when the outer tubular body 79 is being inserted into and guided through the patient.

The hinge portion 86 may be shaped such that upon application of an actuation force, the hinge portion 86 elastically deforms along a predetermined path about a deflection axis 92. The predetermined path may be such that the tip 64 and the hinge portion 86 each are moved to a position where they do not interfere with an interventional device emerging from the distal end of the lumen 82. An imaging field of view of the ultrasound transducer array 68 may be substantially maintained in a position relative to the outer tubular body 79 when the interventional device is advanced through the exit port 81 at the distal end of the lumen 82 and into the field of view. As illustrated in FIGS. 5B through 5D, the hinge portion may comprise two generally parallel sections 86a and 86b, where the ends of each of the generally parallel sections 86a and 86b (e.g., where the hinge portion 86 meets the cradle portion 88 and where the hinge portion 86 meets the tubular body interface portion 84) may be generally shaped to coincide with a cylinder oriented along a center axis 91 of the inner tubular body 80. A central portion of each of the generally parallel sections 86a and 86b may be twisted toward the center axis 91 of the outer tubular body 79 such that the central portions are generally aligned with the deflection axis 92. The hinge portion 86 is disposed such that it is disposed about less than the entirety of the circumference of the inner tubular body 80.

To deflect the deflectable member 52 relative to the outer tubular body 79, the inner tubular body 80 may be moved relative to the outer tubular body 79. Such relative movement is illustrated in FIG. 5D. As shown in FIG. 5D, movement of the inner tubular body 80 in an actuation direction 90 (e.g., in the direction of the ultrasound transducer array 68 when the deflectable member 52 is aligned with the outer tubular body 79) may impart a force on the support 74 in the actuation direction 90. However, since the cradle portion 88 is restrainably connected to the outer tubular body 79 by the tether 78, the cradle portion 88 is prevented from moving substantially in the actuation direction 90. In this regard, the movement of the inner tubular body 80 in the actuation direction 90 may result in the cradle portion 88 pivoting about its interface with the tether 78 and also in the hinge portion 86 bending as illustrated in FIG. 5D. Thus the movement of the inner tubular body 80 in the actuation direction 90 may result in the cradle portion 88 (and the ultrasound transducer array 68 attached to the cradle portion 80) rotating 90 degrees as illustrated in FIG. 5D. Accordingly, movement of the inner tubular body 80 may cause a controlled deflection of the deflectable member 52. As illustrated, the deflectable member 52 may be selectively deflectable away from the center axis 91 of the outer tubular body 79.

In an exemplary embodiment, a movement of the inner tubular body 80 of about 0.1 cm may result in the deflectable member 52 deflecting through an arc of about 9 degrees. In this regard, movement of the inner tubular body 80 of about 1 cm may result in the deflectable member 52 deflecting about 90 degrees. Thusly, the deflectable member 52 may be selectively deflected from a side-looking position to a forward-looking position. Intermediate positions of the deflectable member 52 may be achieved by moving the inner tubular body 80 a predeterminable distance. For example, in the current exemplary embodiment, the deflectable member 52 may be deflected 45 degrees from the side-looking position by moving the inner tubular body 80 about 0.5 cm relative to the outer tubular body 79 in the actuation direction 90. Other appropriate member geometries may be incorporated to produce other relationships between inner tubular body 80 and deflectable member 52 deflection. Moreover, deflections of greater than 90 degrees may be obtained (e.g., such that the deflectable member 52 is at least partially side-looking to a side of the catheter body 54 opposite from that illustrated in FIG. 5C). Moreover, an embodiment of the catheter 50 may be configured such that a predeterminable maximum deflection of the deflectable member 52 may be achieved. For example, the handle 56 may be configured to limit the movement of the slide 58 such that the full range of movement of the slide 58 corresponds to a 45 degree deflection (or any other appropriate deflection) of the deflectable member 52.

The slide 58 and handle 56 may be configured such that substantially any relative motion of the slide 58 to the handle 56 results in a deflection of the deflectable member 52. In this regard, there may be substantially no dead zone of the slide 58 where slide 58 movement does not result in deflection of the deflectable member 52. Furthermore, the relationship between movement of the slide 58 (e.g., relative to the handle 56) and the amount of corresponding deflection of the deflectable member 52 may be substantially linear.

When the deflectable member 52 is deflected from the position illustrated in FIG. 5C so that no part of the tip 64 occupies a cylinder the same diameter as and extending distally from the exit port 81, an interventional device may be advanced through the exit port 81 without contacting the tip 64. As such, the imaging field of view of the ultrasound transducer array 68 may be maintained in a fixed registration relative to the catheter body 54 while the interventional device is being advanced into the catheter body 54, through the exit port 81, and into the imaging field of view of the ultrasound transducer array 68.

When in a forward-looking position, the field of view of the ultrasound transducer array 68 may encompass an area in which an interventional device may be inserted through the lumen 82. In this regard, the ultrasound transducer array 68 may be operable to aid in the positioning and operation of the interventional device.

The deflectable member 52 may deflect about the deflection axis 92 (deflection axis 92 is aligned with the view of FIG. 5D and therefore is represented by a point). The deflection axis 92 may be defined as a point fixed relative to the tubular body interface portion 84 about which the cradle portion 88 rotates. As illustrated in FIG. 5D, the deflection axis 92 may be offset from the center axis 91 of the outer tubular body 79. For any given deflection of the deflectable member 52, a displacement arc 93 may be defined as the minimum arc that is tangent to a face of the deflectable member 52 and tangent the center axis 91 of the catheter. In an embodiment of the catheter 50, the ratio of a maximum cross-dimension of the distal end of the outer tubular body 79 to the radius of the displacement arc 93 may be at least about 1.

The deflectable member 52 may deflect about the deflection axis 92 such that the ultrasound transducer array 68 is positioned proximate to the exit port 81. Such positioning, in conjunction with a small displacement arc 93, reduces the distance an interventional device must travel between emerging from the exit port 81 and entering the field of view of the ultrasound transducer array 68. For example, upon deflection of 90 degrees as shown in FIG. 5D, the ultrasound transducer array 68 may be positioned such that the acoustical face of the ultrasound transducer array 68 is a distance from the exit port 81 (as measured along the central axis 91) that is less than the maximum cross dimension of the distal end of the outer tubular body 79.

As illustrated in FIGS. 5C and 5D, the flexboard 76 may remain interconnected to the catheter body 54 and the deflectable member 52 independent of the deflection of the deflectable member 52.

Figure 5E:
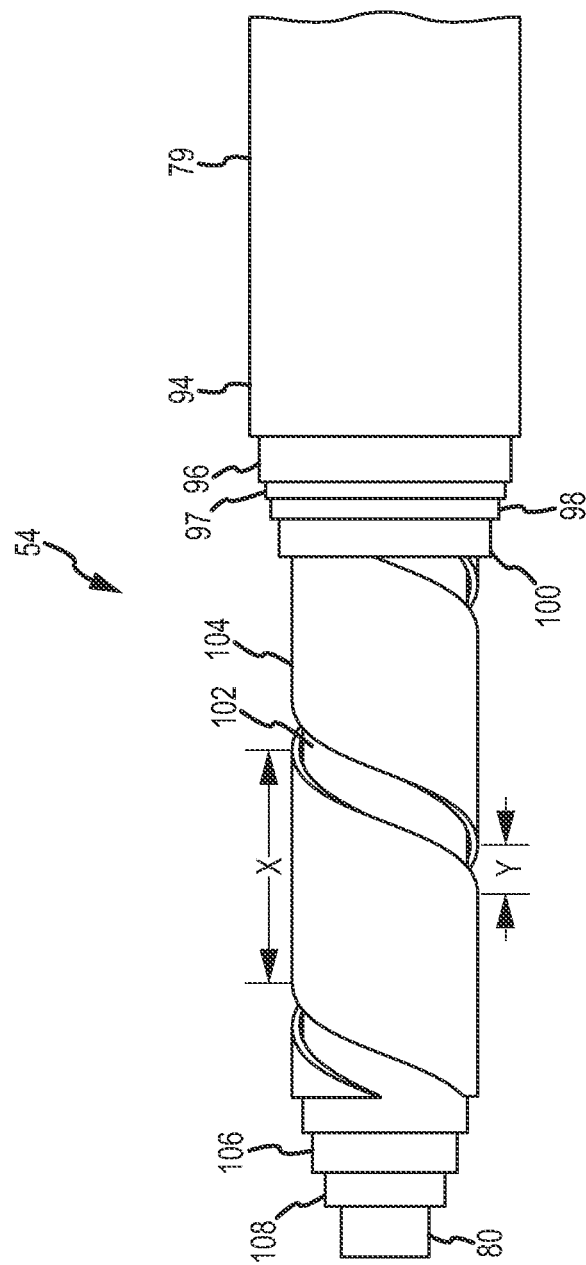

FIG. 5E illustrates an embodiment of the catheter body 54. The catheter body 54 as illustrated comprises the inner tubular body 80 and the outer tubular body 79. In the illustrated embodiment, the outer tubular body 79 comprises all of the components illustrated in FIG. 5E except for the inner tubular body 80. For the illustration of FIG. 5E, portions of various layers have been removed to reveal the construction of the catheter body 54. The outer tubular body 79 may include an outer covering 94. The outer covering 94 may, for example, be a high voltage breakdown material. In an exemplary configuration the outer covering 94 may comprise a substantially non-porous composite film including expanded polytetrafluoroethylene (ePTFE) with a thermal adhesive layer of ethylene fluoroethylene perfluoride on one side. The exemplary configuration may have a width of about 25 mm, a thickness of about 0.0025 mm, an isopropyl alcohol bubble point of greater than about 0.6 MPa, and a tensile strength of about 309 MPa in the length direction (e.g., the strongest direction). The outer covering 94 may be lubricious to aid in the passage of the outer tubular body 79 through the patient. The outer covering 94 may provide a high voltage breakdown (e.g., the outer covering 94 may have a withstand voltage of at least about 2,500 volts AC).

In an exemplary arrangement, the outer covering 94 may include a plurality of helically wound films. A first portion of the plurality of films may be wound in a first direction, and a second portion of the films may be wound in a second direction that is opposite from the first direction. Where each film of the plurality of films has a longitudinal modulus of at least 1,000,000 psi (6,895 MPa) and a transverse modulus of at least 20,000 psi (137.9 MPa), each film of the plurality of films may be wound about a central axis of the tubular body at an angle of less than about 20 degrees relative to the central axis of the tubular body 79.

Within the outer covering 94 may be disposed an outer low-dielectric constant layer 96. The outer low-dielectric constant layer 96 may reduce capacitance between the electrical interconnection member 104 and materials (e.g., blood) outside of the outer covering 94. The outer low-dielectric constant layer 96 may have a dielectric constant of less than about 2.2. In an embodiment, the outer low-dielectric constant layer 96 may be about 0.07-0.15 mm thick. In an embodiment, the outer low-dielectric constant layer 96 may comprise a porous material, such as ePTFE. The voids in the porous material may be filled with a low-dielectric material such as air.

In an exemplary arrangement, the combinative properties of the outer covering 94 and the outer low-dielectric constant layer 96 may include a maximum thickness of 0.005 inches (0.13 mm) and an elastic modulus of 34,500 psi (237.9 MPa). In this regard, the outer covering 94 and the outer low-dielectric constant layer 96 may be viewed as a single composite layer including two sub-layers (the outer covering 94 and the outer low-dielectric constant layer 96).

Moving toward the center of the outer tubular body 79, the next layer may be first tie layer 97. The first tie layer 97 may comprise a film material that may have a melt temperature that is lower then other components of the outer tubular body 79. During fabrication of the outer tubular body 79, the first tie layer 97 may be selectively melted to yield an interconnected structure. For example, selectively melting the first tie layer 97 may serve to secure the outer low-dielectric constant layer 96, the first tie layer 97, and a shield layer 98 (discussed below) to each other.

Moving toward the center of the outer tubular body 79, the next layer may be the shield layer 98. The shield layer 98 may be used to reduce electrical emissions from the outer tubular body 79. The shield layer 98 may be used to shield components internal to the shield layer 98 (e.g., the electrical interconnection member 104) from external electrical noise. The shield layer 98 may be in the form of a double served wire shield or braid. In an exemplary embodiment, the shield layer 98 may be about 0.05-0.08 mm thick. Moving toward the center of the outer tubular body 79, the next layer may be a second tie layer 100. The second tie layer 100 may comprise a film material that may have a melt temperature that is lower then other components of the outer tubular body 79. During fabrication of the outer tubular body 79, the second tie layer 100 may be selectively melted to yield an interconnected structure.

Interior to the second tie layer 100 may be the electrical interconnection member 104. The electrical interconnection member 104 may comprise a plurality of conductors arranged in a side-by-side fashion with an insulative (e.g., non-conductive) material between the conductors. The electrical interconnection member 104 may comprise one or more microminiature flat cables. The electrical interconnection member 104 may contain any appropriate number of conductors arranged in a side-by-side fashion. By way of example, the electrical interconnection member 104 may contain 32 or 64 conductors arranged in a side-by-side fashion. The electrical interconnection member 104 may be helically disposed within the outer tubular body 79. In this regard, the electrical interconnection member 104 may be helically disposed within the wall of the outer tubular body 79. The electrical interconnection member 104 may be helically disposed such that no part of the electrical interconnection member 104 overlies itself. The electrical interconnection member 104 may extend from the proximal end 55 of the catheter 50 to the distal end 53 of the outer tubular body 79. In an embodiment, the electrical interconnection member 104 may be disposed parallel to and along the center axis of the outer tubular body 79.

As illustrated in FIG. 5E, there may be a gap of width Y between the coils of the helically wound electrical interconnection member 104. In addition, the electrical interconnection member 104 may have a width of X as illustrated in FIG. 5E. The electrical interconnection member 104 may be helically disposed such that the ratio of the width X to the width Y is greater than 1. In such an arrangement, the helically disposed electrical interconnection member 104 may provide significant mechanical strength and flexural properties to the outer tubular body 79. This may, in certain embodiments, obviate or reduce the need for a separate reinforcing layer within the outer tubular body 79. Moreover, the gap Y may vary along the length of the outer tubular body 79 (e.g., continuously or in one or more discrete steps). For example, it may be beneficial to have a greater stiffness to the outer tubular body 79 toward the proximal end of the outer tubular body 79. Accordingly, the gap Y may be made smaller toward the proximal end of the outer tubular body 79.

An inner tie layer 102 may be disposed interior to the electrical interconnection member 104. The inner tie layer 102 may be configured similar to and serve a similar function as the second tie layer 100. The inner tie layer 102 may have a melting point of, for example, 160 degrees Celsius. Moving toward the center of the outer tubular body 79, the next layer may be an inner low-dielectric constant layer 106. The inner low-dielectric constant layer 106 may be configured similar to and serve a similar function as the outer low-dielectric constant layer 96. The inner low-dielectric constant layer 106 may be operable to reduce capacitance between the electrical interconnection member 104 and materials (e.g., blood, interventional device) within the outer tubular body 79. Moving toward the center of the outer tubular body 79, the next layer may be an inner covering 108.

The inner covering 108 may be configured similar to and serve a similar function as the outer covering 94. The inner covering 108 and the outer covering 94 may have a combined thickness of at most about 0.002 inches (0.05 mm). Moreover, the inner covering 108 and outer covering 94 may have a combined elastic modulus of at least about 345,000 psi (2,379 MPa). Combined, the inner covering 108 and the outer covering 94 may provide an elongation resistance such that a tensile load, applied to the inner covering 108 and the outer covering 94, of about 3 lbf (13 N) results in no more than a 1 percent elongation of the tubular body 79. In an arrangement, the tubular body 79 may provide an elongation resistance such that a tensile load, applied to the tubular body 79, of about 3 lbf (13 N) results in no more than a 1 percent elongation of the tubular body 79, and in such an arrangement at least about 80 percent of the elongation resistance may be provided by the inner covering 108 and outer covering 94.

The inner covering 108 and outer covering 94 may exhibit a substantially uniform tensile profile about their circumferences and along the length of the tubular body 79 when a tensile load is applied to the tubular body 79. Such a uniform response to an applied tensile load may, inter alia, help to reduce undesirable directional biasing of the catheter body 54 during positioning (e.g., insertion into a patient) and use (e.g., while deflecting the deflectable member 52).

As with the outer covering 94 and the outer low-dielectric constant layer 96, the inner low-dielectric constant layer 106 and the inner covering 108 may be viewed as sub-layers to a single composite layer.

The tie layers (first tie layer 97, second tie layer 100, and inner tie layer 102) may each have substantially the same melting point. In this regard, during construction, the catheter body 54 may be subjected to an elevated temperature that may melt each of the tie layers simultaneously and fix various layers of the catheter body 54 relative to each other. Alternatively, the tie layers may have different melting points allowing selective melting of one or two of the tie layers while leaving the other tie layer or tie layers unmelted. Accordingly, embodiments of catheter bodies 54 may comprise zero, one, two, three, or more tie layers that have been melted to secure various layers of the catheter body 54 to other layers of the catheter body 54.

The aforementioned layers (from the outer covering 94 through the inner covering 108) may each be fixed relative to each other. Together these layers may form the outer tubular body 79. Interior to these layers and movable relative to these layers may be the inner tubular body 80. The inner tubular body 80 may be disposed such that there is an amount of clearance between the outside surface of the inner tubular body 80 and the interior surface of the inner covering 108. The inner tubular body 80 may be a braid reinforced polyether block amide (e.g., the polyether block amide may comprise a PEBAX® material available from Arkema Inc., Philadelphia, Pa.) tube. The inner tubular body 80 may be reinforced with a braided or coiled reinforcing member. The inner tubular body 80 may possess a column strength adequate that it may be capable of translating a lateral motion of the slide 58 along the length of the inner tubular body 80 such that the deflectable member 52 may be actuated by the relative movement of the inner tubular body 80 where it interfaces with the support 74 at the tubular body interface portion 84. The inner tubular body 80 may also be operable to maintain the shape of the lumen 82 passing through the length of the inner tubular body 80 during deflection of the deflectable member 52. Accordingly, a user of the catheter 50 may be capable of selecting and controlling the amount of deflection of the deflectable member 52 through manipulation of the handle 56. The lumen 82 may have a center axis aligned with the center axis 91 of the outer tubular body 79.

To assist in reducing actuation forces (e.g., the force to move the inner tubular body 80 relative to the outer tubular body 79), the inner surface of the inner covering 108, the outer surface of the inner tubular body 80, or both may include a friction reduction layer. The friction reduction layer may be in the form of one or more lubricious coatings and/or additional layers.

In a variation of the embodiment illustrated in FIG. 5E, the inner tubular body 80 may be replaced with an external tubular body that is disposed outside of the outer covering 94. In such an embodiment, the components of the outer tubular body 79 (from the outer covering 94 to the inner covering 108) may remain substantially unchanged from as illustrated in FIG. 5E (the diameters of the components may be reduced slightly to maintain similar overall inner and outer diameters of the catheter body 54). The external tubular body may be fitted outside of the outer covering 94 and may be movable relative to the outer covering 94. Such relative movement may facilitate deflection of the deflectable member 52 in a manner similar to as described with reference to FIGS. 5A through 5D. In such an embodiment, the electrical interconnection member 104 would be a part of the outer tubular body 79 that would be located inside of the external tubular body. The external tubular body may be constructed similarly to the inner tubular body 80 described above.

In an exemplary embodiment, the catheter body 54 may have a capacitance of less than 2,000 picofarads. In an embodiment, the catheter body 54 may have a capacitance of about 1,600 picofarads. In the above-described embodiment of FIG. 5E, the outer covering 94 and outer low-dielectric constant layer 96 may, in combination, have a withstand voltage of at least about 2,500 volts AC. Similarly, the inner covering 108 and inner low-dielectric constant layer 106 may, in combination, have a withstand voltage of at least about 2,500 volts AC. Other embodiments may achieve different withstand voltages by, for example, varying the thicknesses of the covering and/or low-dielectric constant layers. In an exemplary embodiment, the outer diameter of the outer tubular body 79 may, for example, be about 12.25 Fr. The inner diameter of the inner tubular body may, for example, be about 8.4 Fr.

The catheter body 54 may have a kink diameter (the diameter of bend in the catheter body 54 below which the catheter body 54 will kink) that is less than ten times the diameter of the catheter body 54. Such a configuration is appropriate for anatomical placement of the catheter body 54.

As used herein, the term "outer tubular body" refers to the outermost layer of a catheter body and all layers of that catheter body disposed to move with the outermost layer. For example, in the catheter body 54 as illustrated in FIG. 5E, the outer tubular body 79 includes all illustrated layers of the catheter body 54 except the inner tubular body 80. Generally, in embodiments where there is no inner tubular body present, the outer tubular body may coincide with the catheter body.

The various layers of the outer tubular body 79 described with reference to FIG. 5E may, where appropriate, be fabricated by helically winding strips of material along the length of the catheter body 54. In an embodiment, selected layers may be wrapped in a direction opposite of other layers. By selectively winding layers in appropriate directions, some physical properties of the catheter body 54 (e.g., stiffness) may be selectively altered.

FIG. 5F shows an embodiment of an electrical interconnection between the helically disposed electrical interconnection member 104 and the flexboard 76 (a flexible/bendable electrical member). For explanatory purposes, all the parts of the catheter body 54 except the electrical interconnection member 104 and the flexboard 76 are not illustrated in FIG. 5F. The flexboard 76 may have a curved section 109. The curved section 109 may be curved to correspond with the curvature of the outer tubular body 79. The curved section 109 of the flexboard 76 may be disposed within the outer tubular body 79 at the end of the outer tubular body 79 proximate to the deflectable member 52 in the same position with respect to the layers of the outer tubular body 79 as the electrical interconnection member 104. Accordingly, the curved section 109 of the flexboard 76 may come into contact with the electrical interconnection member 104. In this regard, the distal end of the electrical interconnection member 104 may interconnect to the flexboard 76 in an interconnect region 110.

Within the interconnect region 110, the electrically conductive portions (e.g., wires) of the electrical interconnection member 104 may be interconnected to electrically conductive portions (e.g., traces, conductive paths) of the flexboard 76. This electrical interconnection may be achieved by peeling back or removing some of the insulative material of the electrical interconnection member 104 and contacting the exposed electrically conductive portions to corresponding exposed electrically conductive portions on the flexboard 76. The end of the electrical interconnection member 104 and the exposed conductive portions of the electrical interconnection member 104 may be disposed at an angle relative to the width of the electrical interconnection member 104. In this regard, the pitch (e.g., the distance between exposed electrically conductive portions) between the exposed electrically conductive portions of the flexboard 76 may be greater than the pitch (as measured across the width) of the electrical interconnection member 104, while maintaining an electrical interconnection between each conductor of both the electrical interconnection member 104 and the flexboard 76.

As illustrated in FIG. 5F, the flexboard 76 may comprise a flexing or bending region 112 that has a width narrower than the width of the electrical interconnection member 104. As will be appreciated, the width of each individual electrically conductive path through the flexing region 112 may be smaller than the width of each electrically conductive member within the electrical interconnection member 104. Furthermore the pitch between each electrically conductive member within the flexing region 112 may be smaller than the pitch of the electrical interconnection member 104.

The flexing region 112 may be interconnected to an array interface region 114 of the flexboard 76 through which the electrically conductive paths of the electrical interconnection member 104 and the flexboard 76 may be electrically interconnected to individual transducers of the ultrasound transducer array 68.

As illustrated in FIGS. 5C and 5D, the flexing region 112 of the flexboard 76 may be operable to flex during deflection of the deflectable member 52. In this regard, the flexing region 112 may be bendable in response to deflection of the deflectable member 52. The individual conductors of the electrical interconnection member 104 may remain in electrical communication with the individual transducers of the ultrasound transducer array 68 during deflection of the deflectable member 52.

In an embodiment, the electrical interconnection member 104 may comprises two or more separate sets of conductors (e.g., two or more microminiature flat cables). In such an embodiment, each of the separate sets of conductors may be interconnected to the flexboard 76 in a manner similar to as illustrated in FIG. 5F. Furthermore, the electrical interconnection member 104 (either a unitary electrical interconnection member 104 as illustrated in FIG. 5F or an electrical interconnection member 104 comprising a plurality of generally parallel distinct cables) may comprise members that extend from the distal end 53 to the proximal end 55 of the catheter body 54 or the electrical interconnection member 104 may comprise a plurality of discrete, serially interconnected members that together extend from the distal end 53 to the proximal end 55 of the catheter body 54. In an embodiment, the flexboard 76 may include the electrical interconnection member 104. In such an embodiment, the flexboard 76 may have a helically wrapped portion extending from the distal end 53 to the proximal end 55 of the catheter body 54. In such an embodiment, no electrical conductor interconnections (e.g., between the flexboard 76 and a microminiature flat cable) may be required between the array interface region 114 and the proximal end of the catheter body 54.

FIGS. 6A through 6D show an embodiment of a catheter that includes a deflectable member 116 wherein the deflectable member 116 is deflectable by moving an elongate member relative to an outer tubular body 118. It will be appreciated that the embodiment illustrated in FIGS. 6A through 6D does not include an inner tubular body and the outer tubular body 118 may also be characterized as a catheter body.

Figure 6A:
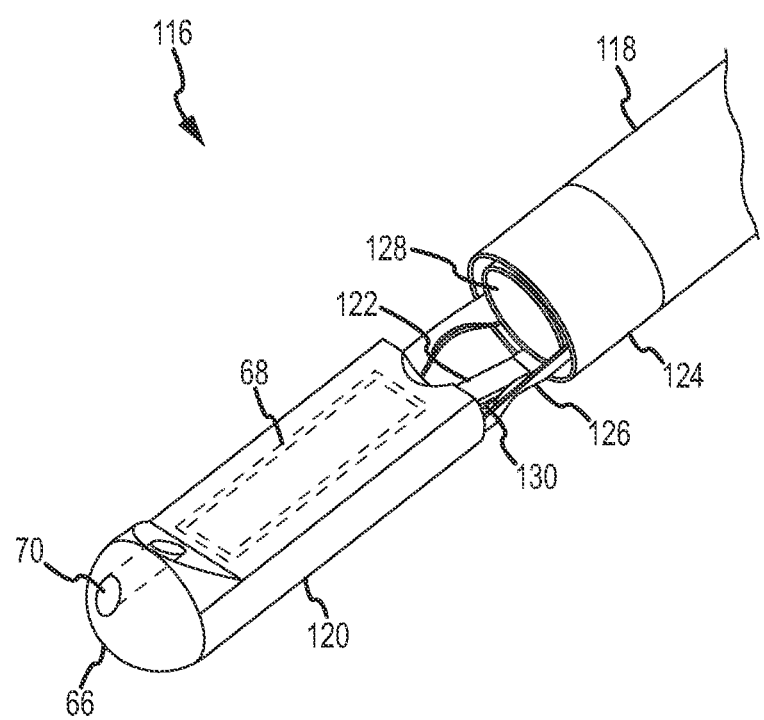
FIGS. 6A through 6D show an embodiment of a catheter that includes a deflectable member wherein the deflectable member is deflectable by moving an elongate member relative to a catheter body.

The deflectable member 116 may be selectively deflectable. As shown in FIG. 6A, the illustrated deflectable member 116 includes a tip 120. The tip 120 may include the ultrasound transducer array 68 and may include a rounded distal end 66 and guide wire aperture 70 similar to the tip 64 described with reference to FIG. 5B. As with the tip 64 of FIG. 5B, the ultrasound transducer array 68 may be side-looking when the deflectable member 116 is aligned with the outer tubular body 118. In this regard, the ultrasound transducer array 68 may be operable to image anatomical landmarks during catheter insertion to aid in guiding and/or positioning the outer tubular body 118.

The outer tubular body 118 may include a lumen 128 operable to allow an interventional device to pass therethrough. At least a portion of the deflectable member 116 may be permanently positioned distal to the distal end of with the outer tubular body 118. In an embodiment, the entirety of the deflectable member 116 may be permanently positioned distal to the distal end of the outer tubular body 118.

The deflectable member 116 may be deflectable relative to the outer tubular body 118. In this regard, the deflectable member 116 may be interconnected to one or more elongate members to control the motion of the deflectable member 116 as it is being deflected. The elongate member may take the form of a pull wire 130. The pull wire 130 may be a round wire. Alternatively, for example, the pull wire 130 may be rectangular in cross-section. For example, the pull wire may be rectangular in cross-section with a width-to-thickness ratio of about 5 to 1.

As with the catheter embodiment illustrated in FIGS. 5B through 5E, the catheter of FIGS. 6A through 6D may include a support 126 that supports the ultrasound transducer array 68. The support 126 may interconnect the deflectable member 116 to the outer tubular body 118. A flexboard 122 may contain electrical interconnections operable to electrically connect the ultrasound transducer array 68 to an electrical interconnection member 104 (shown in FIG. 6D) disposed within the outer tubular body 118. The exposed portion of flexboard 122 may be encapsulated similarly to the flexboard 76 discussed above.

The outer tubular body 118 may include a distal portion 124. The distal portion 124 may comprise a plurality of wrapped layers disposed about a securement portion 133 (shown in FIGS. 6B and 6C) of the support 126. The wrapped layers may serve to secure the securement portion 133 to an inner portion of the outer tubular body 118 as discussed below with reference to FIG. 6D.

Figure 6B:
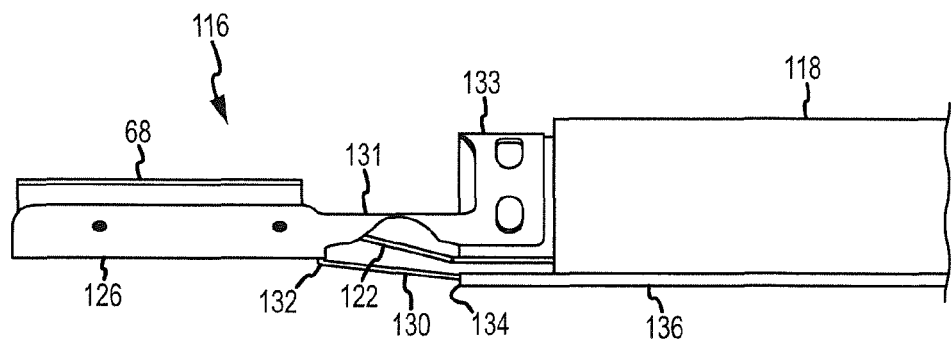
Figure 6C:
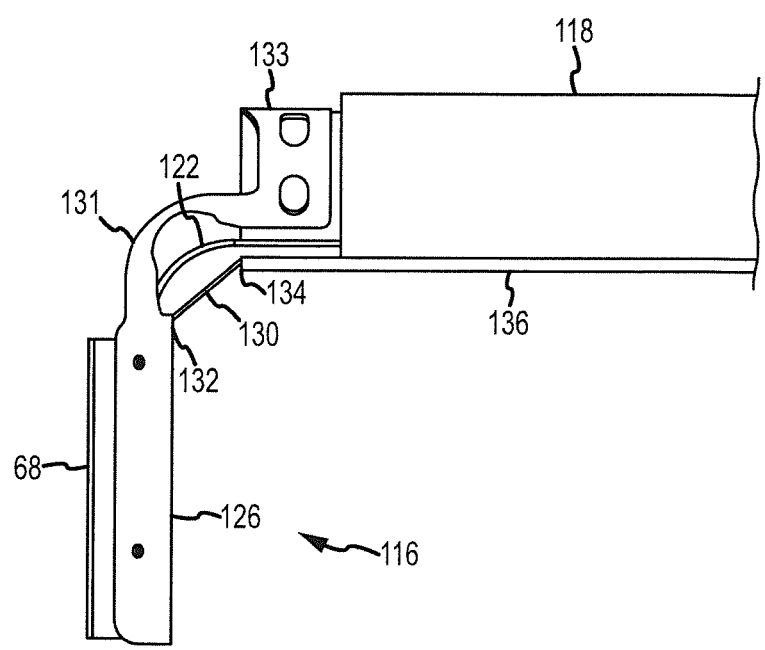

Deflection of the deflectable member 116 will now be discussed with reference to FIGS. 6B and 6C. FIGS. 6B and 6C illustrate the deflectable member 116 with the portion of the tip 120 surrounding the ultrasound image array 68 and support 126 removed. Also, the distal portion 124 of the outer tubular body 118 wrapped around the securement portion 133 has been removed. The support 126 may be configured similarly to the support 74 discussed above. The support 126 may further include a hinge portion 131 similar to the hinge portion 86.

To deflect the deflectable member 116 relative to the outer tubular body 118, the pull wire 130 may be moved relative to the outer tubular body 118. As shown in FIG. 6C, pulling the pull wire 130 (e.g., toward the handle 56) may impart a force on the support 126 at a pull wire anchor point 132 directed along the pull wire 130 toward a pull wire outlet 134. The pull wire outlet 134 is the point where the pull wire 130 emerges from a pull wire housing 136. The pull wire housing 136 may be fixed to the outer tubular body 118. Such a force may result in the deflectable member 116 bending toward the pull wire outlet 134. As in the embodiment illustrated in FIGS. 5C and 5D, the deflection of the deflectable member will be constrained by the hinge portion 131 of the support 126. As illustrated in FIG. 6C, the resultant deflection of the deflectable member 116 may result in the ultrasound transducer array 68 being pivoted to a forward-looking position. It will be appreciated that varying amounts of deflection of the deflectable member 116 may be achieved through controlled movement of the pull wire 130. In this regard, any deflection angle between 0 degrees and 90 degrees may be achievable by displacing the pull wire 130 a lesser amount than as illustrated in FIG. 6C. Furthermore, deflections of greater than 90 degrees may be obtainable by displacing the pull wire 130 a greater amount than as illustrated in FIG. 6C. As illustrated in FIGS. 6B and 6C, the flexboard 122 may remain interconnected to the outer tubular body 118 and the deflectable member 116 independent of the deflection of the deflectable member 116.

Figure 6D:
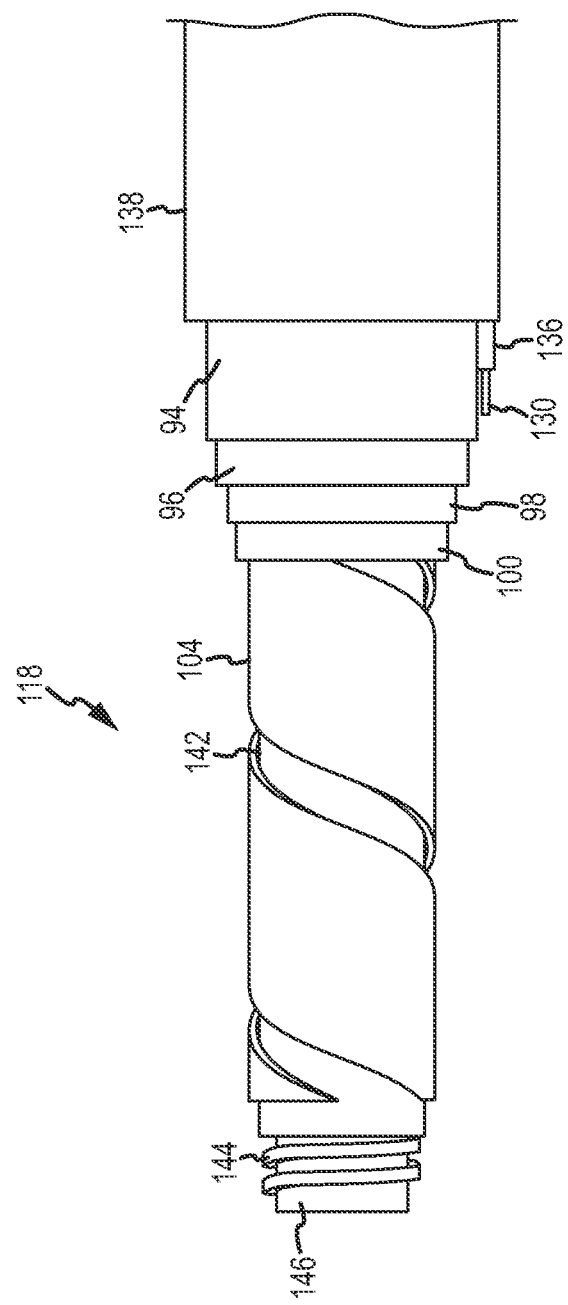

FIG. 6D illustrates an embodiment of the outer tubular body 118. For the illustration of FIG. 6D, portions of various layers have been removed to reveal the construction of the outer tubular body 118. Layers similar to those of the embodiment of FIG. 5E are labeled with the same reference numbers as in FIG. 5E and will not be discussed at length here. The pull wire housing 136 housing the pull wire 130 may be disposed proximate to the outer covering 94. An external wrap 138 may then be disposed over the outer covering 94 and pull wire housing 136 to secure the pull wire housing 136 to the outer covering 94. Alternatively, the pull wire housing 136 and pull wire 130 may, for example, be disposed between the outer covering 94 and the outer low-dielectric constant layer 96. In such an embodiment, the outer wrap 138 may not be needed. Other appropriate locations for the pull wire housing 136 and pull wire 130 may be utilized.

Disposed interior to the outer low-dielectric constant layer 96 may be the shield layer 98. A first tie layer (not shown in FIG. 6D), similar to first tie layer 97, may be disposed between the outer low-dielectric constant layer 96 and the shield layer 98. Disposed interior to the shield layer may be the second tie layer 100. Disposed interior to the second tie layer 100 may be the electrical interconnection member 104. Disposed interior to the electrical interconnection member 104 may be an inner low-dielectric constant layer 142. In this regard, the electrical interconnection member 104 may be helically disposed within the wall of the outer tubular body 118.

Moving toward the center of the outer tubular body 118, the next layer may be a coiled reinforcement layer 144. The coiled reinforcement layer 144 may, for example, comprise a stainless steel coil. In an exemplary embodiment, the coiled reinforcement layer 144 may be about 0.05-0.08 mm thick. Moving toward the center of the outer tubular body 118, the next layer may be an inner covering 146. The inner covering 146 may be configured similar to and serve a similar function as the outer covering 94. The lumen 128 may have a center axis aligned with the center axis of the outer tubular body 118.

As noted above, the wrapped layers of the distal portion 124 of the outer tubular body 118 may serve to secure the securement portion 133 of the support 126 to an inner portion of the outer tubular body 118. For example, each layer outboard of the electrical interconnection member 104 may be removed in the distal portion 124. Furthermore, the electrical interconnection member 104 may be electrically interconnected to the flexboard 122 proximal to the distal portion 124 in a manner similar to as described with reference to FIG. 5F. Accordingly, the securement portion 133 of the support 126 may be positioned over the remaining inner layers (e.g., the inner low-dielectric constant layer 142, the coiled reinforcement layer 144 and the inner covering 146) and a plurality of layers of material may be wrapped about the distal portion 124 to secure the securement portion 133 to the outer tubular body 118.

The outer diameter of the outer tubular body 118 may, for example, be about 12.25 Fr. The inner diameter of the outer tubular body 118 may, for example, be about 8.4 Fr.

Figure 7A:
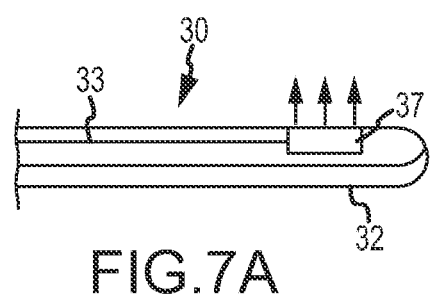
FIGS. 7A and 7B show a further aspect wherein an ultrasound transducer array is located near the distal end of the catheter. The array can be manipulated between side-looking and forward-looking by utilizing an actuation device attached to the array and extending to the proximal end of the catheter.
Figure 7B:
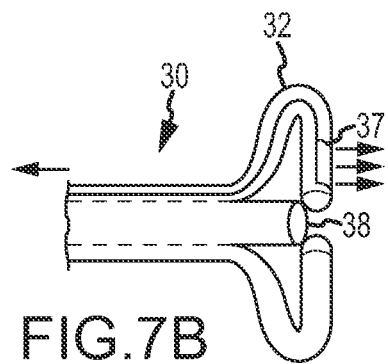

FIGS. 7A and 7B demonstrate further embodiments. As shown, the catheter 30 comprises a deflectable distal end 32. Located at deflectable distal end 32 is ultrasound transducer array 37. The catheter also includes wire 33 attached to the ultrasound transducer array 37 and extending to the proximal end of catheter 30 where it exits through a port or other opening at the proximal end of catheter 30. As shown in FIG. 7A, ultrasound transducer array 37 is in a "side-looking" configuration. The catheter can be delivered to the treatment site with the ultrasound transducer array 37 in the "side-looking" configuration, as shown in FIG. 7A. Once the treatment site is reached, wire 33 can be pulled in a proximal direction to deflect deflectable distal end 32 to result in ultrasound transducer array 37 being moved to a "forward-looking" configuration, as shown in FIG. 7B. As shown in FIG. 7B, once ultrasound transducer array 37 is positioned in the "forward-looking" position and deflectable distal end 32 is deflected as shown, generally centrally located lumen 38 is then available for delivery of a suitable interventional device to a point distal to the catheter distal end 32. Alternatively, a tube containing lumen 38 and movable relative to the outer surface of the catheter 30 may be used to deflect the deflectable distal end 32 to the "forward-looking" configuration.

Figure 8A:
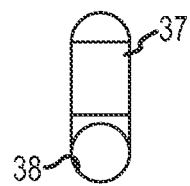
FIGS. 8A through 8D show various exemplary variations of the catheter of FIGS. 7A and 7B.
Figure 8B:
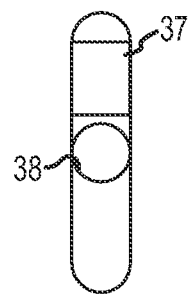
Figure 8C:
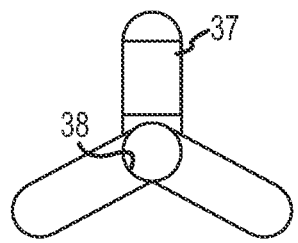
Figure 8D:
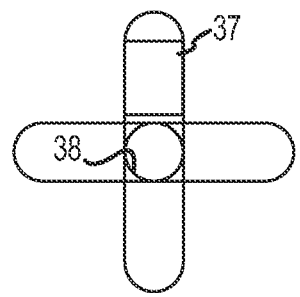

FIG. 8A is a front view of a single lobe configuration of the device shown in FIGS. 7A and 7B. FIG. 8B shows a dual-lobe configuration of the catheter shown in FIGS. 7A and 7B. FIG. 8C shows a tri-lobe configuration and FIG. 8D shows a quad-lobe configuration. As will be understood, any suitable number of lobes can be constructed as desired. Moreover, in multiple-lobe configurations, ultrasound transducer arrays 37 may be disposed on one or more of the lobes.

Figure 9:
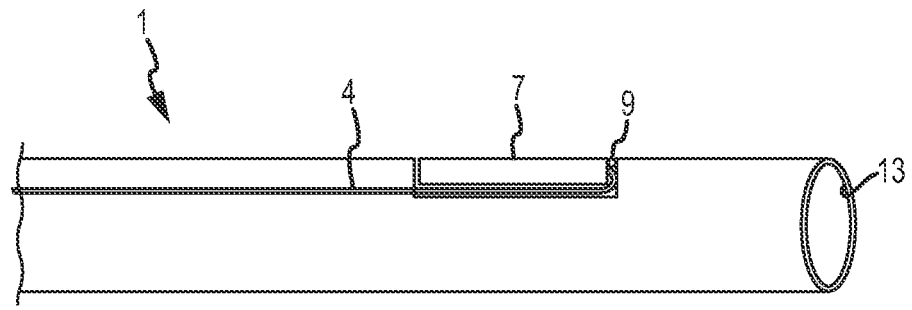
FIGS. 9, 9A and 9B demonstrate further embodiments wherein an ultrasound array is deflectable.
Figure 9A:
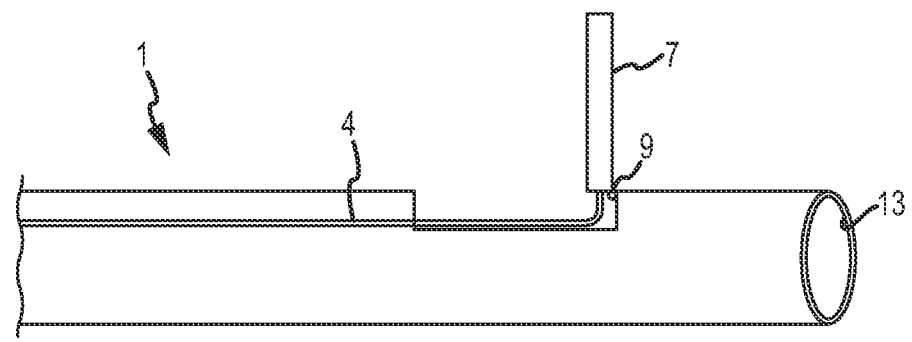
Figure 9B:
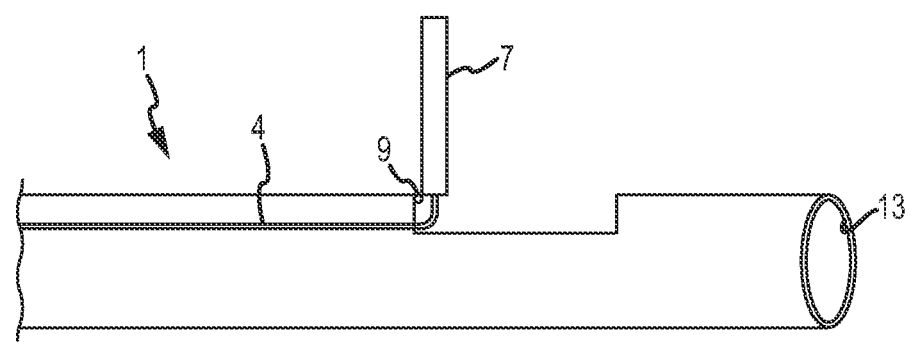

Further embodiments are shown in FIGS. 9, 9A and 9B. FIG. 9 shows catheter 1 having an ultrasound transducer array 7 near the distal end thereof. The ultrasound transducer array 7 is attached to catheter 1 by hinge 9. Electrically conductive wires 4 are connected to ultrasound transducer array 7 and extend proximally to the proximal end of the catheter 1. The catheter 1 includes distal exit port 13. The hinge 9 can be located at the distal end of ultrasound transducer array 7, as shown in FIG. 9A, or at the proximal end of ultrasound transducer array 7, as shown in FIG. 9B. In any event, the ultrasound transducer array 7 can be either passively or actively deflectable, as discussed above. Ultrasound transducer array 7 can be deflected up to the forward-looking configuration (as shown in FIGS. 9A and 9B) and an interventional device can be advanced at least partially out of distal exit port 13, such that at least a portion of the interventional device will be in the field of view of the ultrasound transducer array 7.

FIGS. 10A and 10B demonstrate a further embodiment where the catheter includes ultrasound transducer array 7 near the catheter distal end 2 of the catheter. The catheter further includes steerable segment 8 and lumen 10. Lumen 10 can be sized to accept a suitable interventional device that can be inserted at the proximal end of the catheter and advanced through lumen 10 and out port 13. The catheter can further include guidewire receiving lumen 16. Guidewire receiving lumen 16 can include proximal port 15 and distal port 14, thus allowing for the well known "rapid exchange" of suitable guidewires.

As further demonstrated in FIGS. 11 and 11A and 11B, the catheter steerable segment 8 can be bent in any suitable direction. For example, as shown in FIG. 11A the steerable segment is bent away from port 13 and as shown in FIG. 11B the steerable segment is bent toward port 13.

Figure 12:
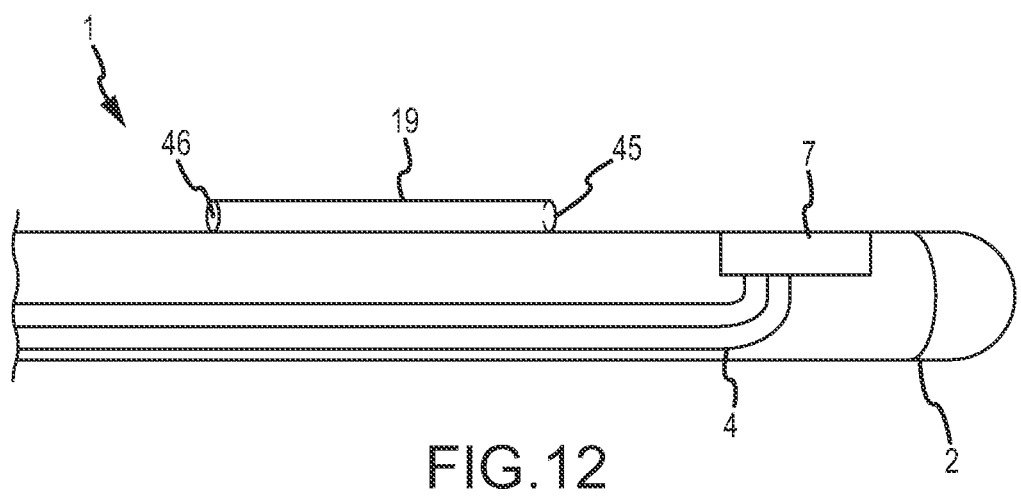
FIG. 12 demonstrates a still further embodiment.

FIG. 12 demonstrates yet another embodiment. Specifically, catheter 1 can include ultrasound transducer array 7 located at the distal end 2 of the catheter 1. Electrically conductive wires 4 are attached to the ultrasound transducer array 7 and extend to the proximal end of the catheter 1. Lumen 19 is located proximal to the ultrasound transducer array 7 and includes proximal port 46 and distal port 45. The lumen 19 can be sized to accept a suitable guidewire and/or interventional device. Lumen 19 can be constructed of a suitable polymer tube material, such as ePTFE. The electrically conductive wires 4 can be located at or near the center of the catheter 1.

Figure 13:
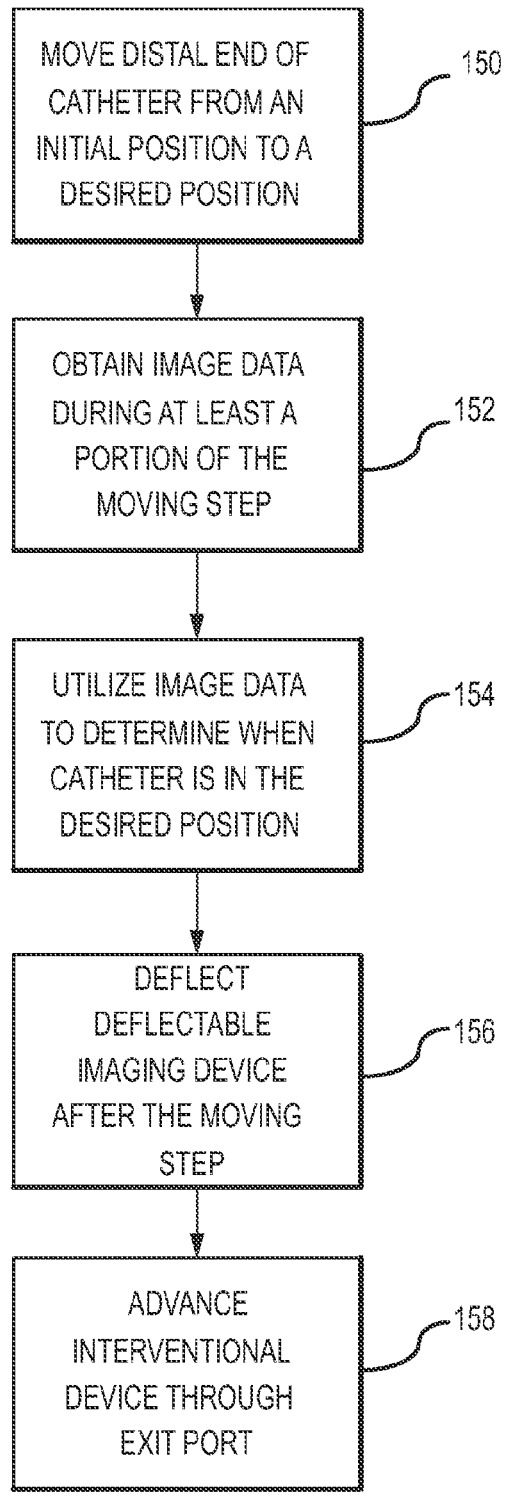
FIG. 13 is a flow chart for an embodiment of a method of operating a catheter.

FIG. 13 is a flow chart for an embodiment of a method of operating a catheter having a deflectable imaging device located at a distal end thereof. The first step 150 in the method may be to move the distal end of the catheter from an initial position to a desired position, wherein the deflectable imaging device is located in a first position during the moving step. The deflectable imaging device may be side-looking when in the first position. The moving step may include introducing the catheter into a body through an entry site that is smaller than the aperture of the deflectable imaging device. The moving step may include rotating the catheter relative to its surroundings.

The next step 152 may be to obtain image data from the deflectable imaging device during at least a portion of the moving step. The obtaining step may be performed with the deflectable imaging device located in the first position. During the moving and obtaining steps, a position of the deflectable imaging device relative to the distal end of the catheter may be maintained. Thus the deflectable imaging device may be moved and images may be obtained without moving the deflectable imaging device relative to the distal end of the catheter. During the moving step, the catheter, and therefore the deflectable imaging device, may be rotated relative to its surroundings. Such rotation may allow the deflectable imaging device to obtain images in a plurality of different directions transverse to the path traveled by the catheter during the moving step.

The next step 154 may be to utilize the image data to determine when the catheter is located at the desired position. For example, the image data may indicate the position of the deflectable imaging device, and therefore the distal end of the catheter, relative to a landmark (e.g., an anatomical landmark).

The next step 156 may be to deflect the deflectable imaging device from the first position to a second position. The deflecting step may follow the moving step. The deflectable imaging device may be forward-looking in the second position. The deflectable imaging device may be angled at least 45 degrees relative to a center axis of the catheter when in the second position. Optionally, after the deflecting step, the deflectable imaging device may be returned to the first position and the catheter repositioned (e.g., repeating the moving step 150, the obtaining step 152, and the utilizing step 154). Once repositioned, the deflecting step 156 may be repeated and the method may be continued.

In an embodiment, the catheter may comprise an outer tubular body and an activation device, each extending from a proximal end to the distal end of the catheter. In such an embodiment, the deflecting step may include translating a proximal end of at least one of the outer tubular body and actuation device relative to a proximal end of the other one of the outer tubular body and actuation device. The deflectable imaging device may be supportably interconnected by a hinge to one of the outer tubular body and the actuation device, and the deflecting step may further comprise applying a deflection force to the hinge in response to the translating step. Furthermore, the deflecting step may further include initiating the application of the deflection force to the hinge in response to the translating step. The deflection force may be applied and then maintained by manipulating a handle interconnected to the proximal end of the catheter. Moreover, the applying step may comprise communicating the deflection force by the actuation device from the proximal end to the distal end of the catheter in a balanced and distributed manner about a center axis of the outer tubular body.

The next step 158 may be to advance an interventional device through an exit port at the distal end of the catheter and into an imaging field of view of the deflectable imaging device in the second position. The imaging field of view may be maintained in substantially fixed registration to the distal end of the catheter during the advancing step.

After advancing and using the interventional device (e.g., to perform a procedure, to install or retrieve a device, to make a measurement), the interventional device may be withdrawn through the exit port. The deflectable imaging device may then be returned to the first position. The return to the first position may be facilitated by an elastic deformation quality of the hinge. For example, the hinge may be biased toward positioning the deflectable imaging device in the first position. As such, when the deflectable imaging device is in the second position and the deflection force is removed, the deflectable imaging device may return to the first position. After withdrawal of the interventional device through the exit port (and optionally from the entire catheter) and return of the deflectable imaging device to the first position, the catheter may then be repositioned and/or removed.

As with the supports 74, 126 above, the supports described below may be made from any appropriate material, such as, for example, a shape memory material (e.g., Nitinol). Any appropriate tubular body discussed herein may be configured to include any suitable electrical configuration member. For example, where appropriate in the embodiments discussed below, the outer tubular bodies may contain electrical interconnection members similar to the electrical interconnection member 104 of FIG. 5E.

Figure 14A:
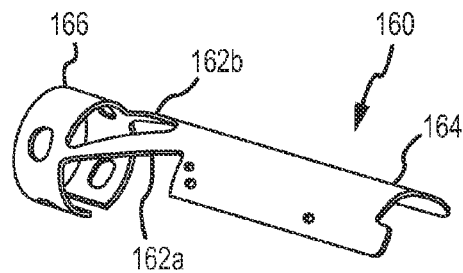
FIGS. 14A, 14B, 14C, 14D and 15 illustrate alternative support designs.
Figure 14B:
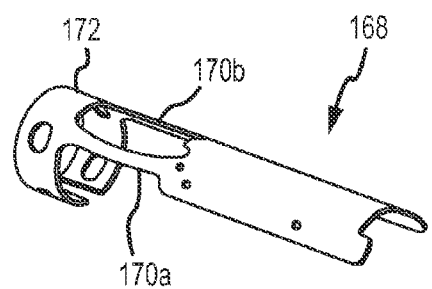
Figure 14C:
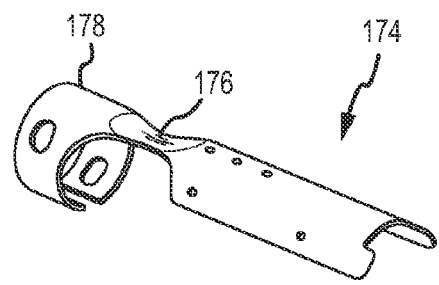

The support 74 of FIGS. 5B through 5D, the support 126 of FIGS. 6A through 6C, and any similarly configured support disclosed herein may contain variations of the hinge portion 86 described with reference to FIGS. 5B through 5D and hinge portion 131 described with reference to FIGS. 6A through 6C. For example, FIGS. 14A through 14C illustrate three alternative hinge portion designs. FIG. 14A illustrates a support 160 that includes hinge portions 162*a*, 162*b* that are tapered—the hinge portions 162 *a/b* become thinner as the distance from a cradle portion 164 increases in the direction of a tubular body interface portion 166.

Figure 14D:
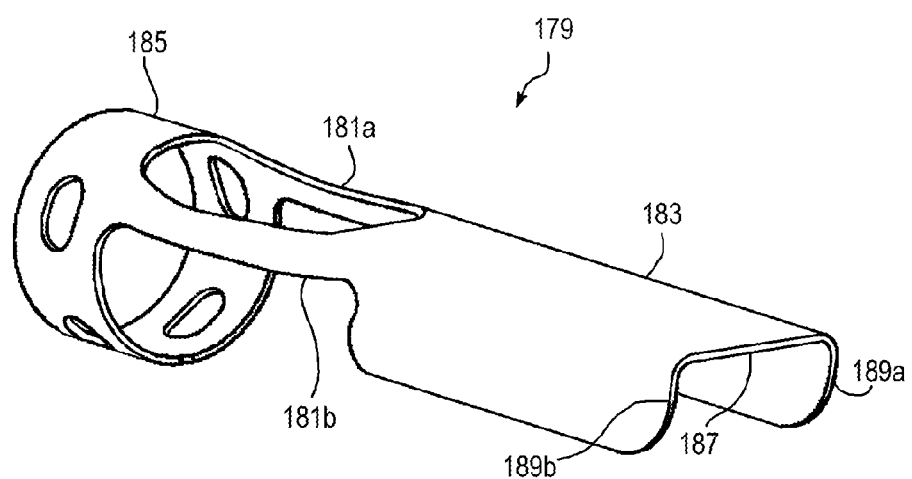

FIG. 14B illustrates a support 168 that includes hinge portions 170*a*, 170*b* that are scalloped and disposed within a curved plane of a tubular body interface portion 172. FIG. 14C illustrates a support 174 that includes a unitary hinge portion 176. The unitary hinge portion 176 is a scalloped with a narrow portion disposed proximate to its midpoint. Furthermore, the unitary hinge portion 176 is curved such that a portion of the unitary hinge portion 176 is disposed within the interior of a tube defined by and extending from a tubular body interface portion 178. FIG. 14D illustrates a support 179 that includes hinge portions 181*a*, 181*b*, a tubular body interface portion 185 and a cradle portion 183. The cradle portion 183 includes a flat section 187 and two side sections 189*a*, 189*b* oriented generally perpendicular to the flat section 187. Such design variations as those illustrated in FIGS. 14A through 14D may provide satisfactory cycles to failure (e.g., bending cycles), lateral stiffness and angular bending stiffness, while maintaining strain and plastic deformation within acceptable levels.

Figure 15:
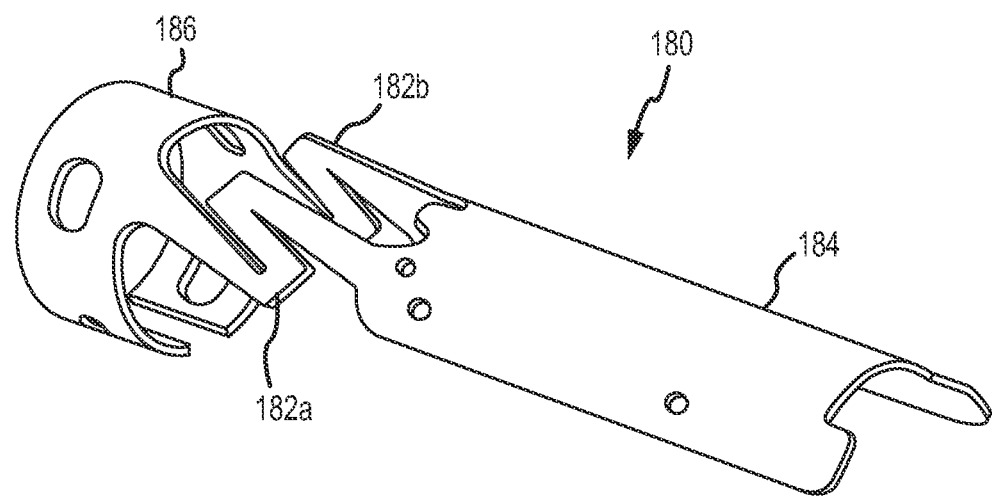

FIG. 15 illustrates a support 180 that incorporates a pair of zigzagging hinge portions 182*a*, 182*b*. Such a design allows for the maintenance of adequate hinge portion 182*a*, 182*b* width and thickness while allowing for a longer effective cantilever bend length, thus decreasing the level of force required to deflect a cradle portion 184 relative to a tubular body interface portion 186. Other appropriate configurations where the effective cantilever bend length may be increased (as compared to a straight hinge portion) may also be utilized.

Figure 16:
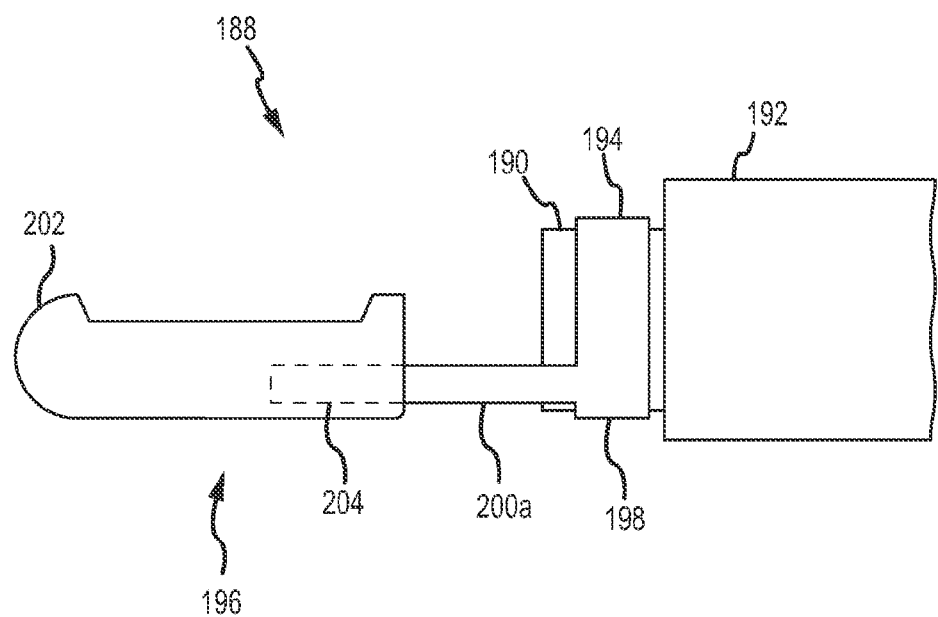
FIG. 16 illustrates a further embodiment of a catheter.

FIG. 16 illustrates a catheter 188 that includes an inner tubular body 190 and an outer tubular body 192. Attached to the inner tubular body 190 is a support 194 that supports a deflectable member 196. The support 194 includes a tubular body interface portion 198 that is attached to the inner tubular body 190 using any appropriate method of attachment such as, for example, clamping and/or gluing. The support 194 further includes two hinge portions: a first hinge portion 200*a* and a second hinge portion (not visible in FIG. 16 due to its position parallel to and directly behind the first hinge portion 200*a*). The deflectable member 196 includes a tip portion 202 that may, for example, be molded over an end portion 204 of the first hinge portion 200*a* and the second hinge portion. The tip portion 202 may also contain an ultrasound imaging array, appropriate electrical connections, and any other appropriate component. Any appropriate electrical interconnection scheme and any appropriate deflection actuation scheme, such as those described herein, may be used with the support 194 of FIG. 16.

Figure 17:
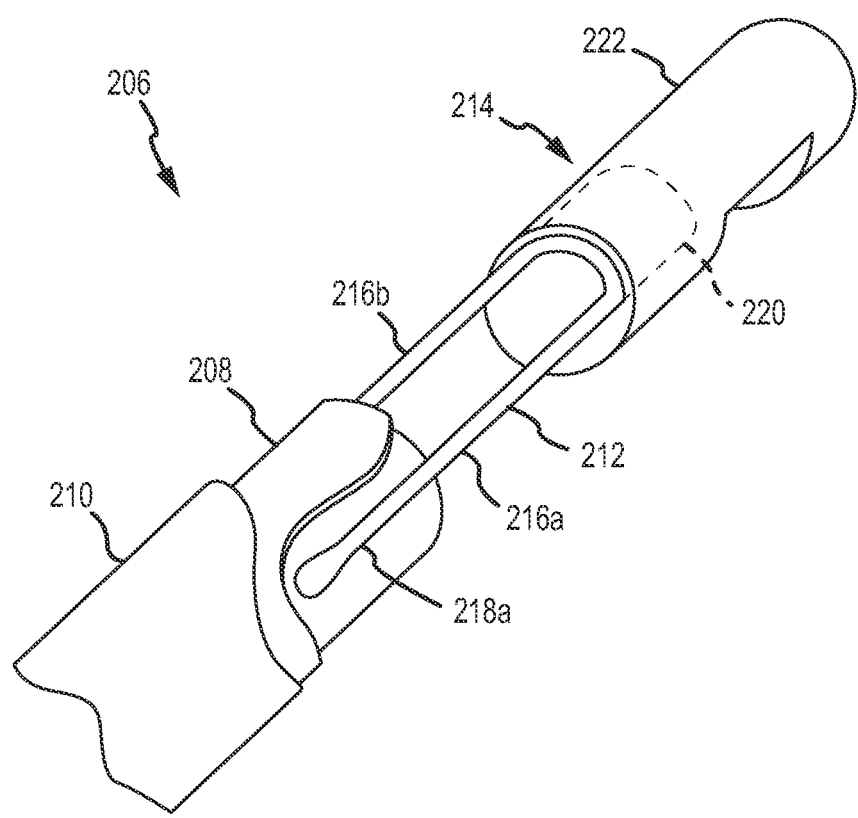
FIG. 17 illustrates a further embodiment of a catheter.

FIG. 17 illustrates a catheter 206 that includes an inner tubular body 208 and an outer tubular body 210. Attached to the inner tubular body 208 is a support 212 that supports a deflectable member 214. The support 212 includes first and second hinge portions 216*a*, 216*b* that allow for deflection of the deflectable member 214 relative to the inner and outer tubular bodies 208, 210. The outer tubular body 210 has been cut away in FIG. 17 to aid this description. The support 212 further includes a first inner tubular body interface region 218*a*. The first inner tubular body interface region 218*a* may be disposed between layers of the inner tubular body 208 to secure the support 212 to the inner tubular body 208. To illustrate this attachment in FIG. 17, a portion of the inner tubular body 208 disposed over the first inner tubular body interface region 218*a* has been cut away. A second inner tubular body interface region is attached to the second hinge portion 216*b* and is disposed within the layers of the inner tubular body 208 and is therefore not visible in FIG. 17. The inner tubular body interface regions may be attached to the inner tubular body 208 using any appropriate attachment method (e.g., glued, tacked). The support 212 may further include an end portion 220. The deflectable member may include a tip portion 222 that may be molded over the end portion 220 to secure the deflectable member 214 to the support 212 (similar to as described with reference to FIG. 16). The tip portion 222 may also contain an ultrasound imaging array, appropriate electrical connections, and any other appropriate component. Any appropriate electrical interconnection scheme and any appropriate deflection actuation scheme, such as those described herein, may be used with the support 212 of FIG. 17. In an alternate configuration, the support 212 may include a single hinge portion.

Figure 18A:
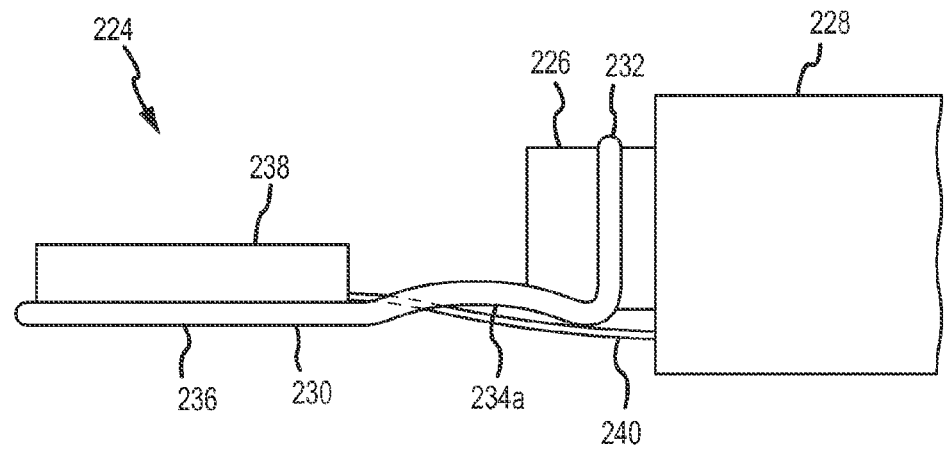
FIGS. 18A and 18B demonstrate a further embodiment wherein an ultrasound array is deflectable.
Figure 18B:
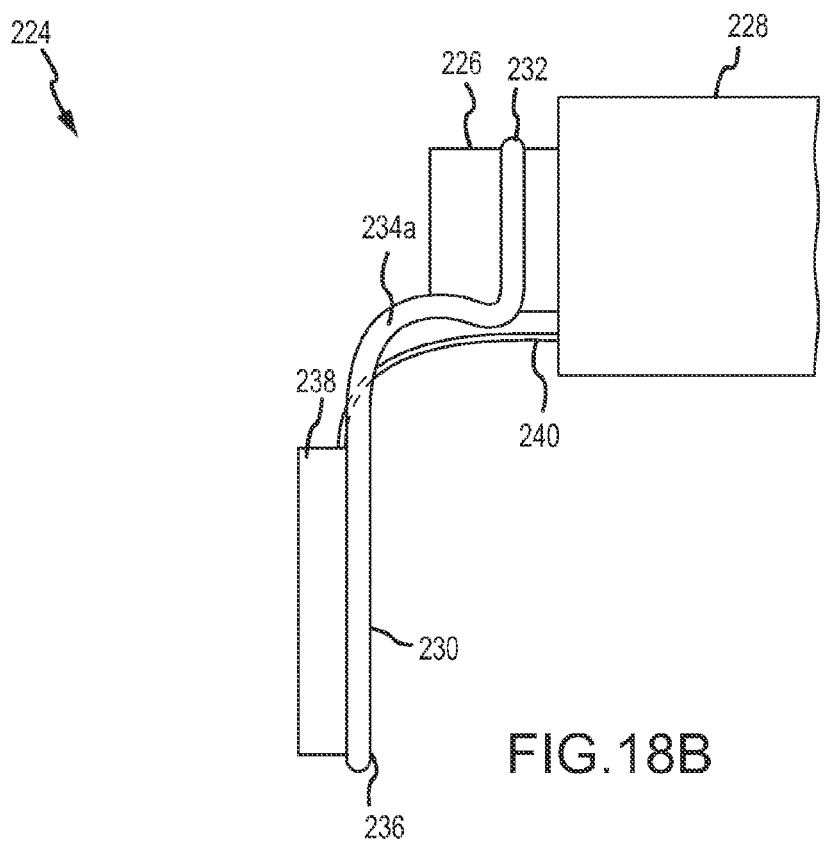

FIGS. 18A and 18B illustrate a catheter 224 that includes an inner tubular body 226 and an outer tubular body 228. Attached to the inner tubular body 226 is a support 230. The support 230 is constructed from a strand of wire bent into a shape to perform the functions described below. The support 230 may be constructed such that it is made from a continuous loop of wire (e.g., during formation, the ends of the wire strand used to make the support 230 may be attached to each other). The support 230 includes a tubular body interface portion 232 that is operable to be secured to the inner tubular body 226 in any appropriate way (e.g., clamped and/or bonded). The support 230 further includes two hinge portions: a first hinge portion 234*a* and a second hinge portion (not visible in FIGS. 18A and 18B due to its position parallel to and directly behind the first hinge portion 234*a*). The support 230 further includes an array support portion 236 operable to support an ultrasound imaging array 238. The hinge portions allow for deflection of the ultrasound imaging array 238 relative to the inner and outer tubular bodies 226, 228. The catheter 224 may further include a tether and/or electrical interconnection member 240. The catheter 224 may also further include a second tether and/or electrical interconnection member (not shown). As illustrated in FIGS. 18A and 18B, an extension (a leftward movement in FIGS. 18A and 18B) of the inner tubular body 226 relative to the outer tubular body 228 may result in the deflection of the ultrasound imaging array 238 relative to the outer tubular body 228. The catheter 224 may also include a tip portion (not shown) that may be molded over the ultrasound imaging array 238, array support portion 236, and any other appropriate components. Any appropriate electrical interconnection scheme and any appropriate deflection actuation scheme, such as those described herein, may be used with the support 230 of FIGS. 18A and 18B.

Returning briefly to FIGS. 5C and 5D, the tether 78 and flexboard 76 are illustrated interconnected between the outer tubular body 79 and the cradle portion 88. In an alternate arrangement of FIGS. 5C and 5D, the functions of the tether 78 and flexboard 76 may be combined. In such an arrangement, the flexboard 76 may also act as a tether. The flexboard 76 that also serves as a tether may be a typical flexboard, or it may be specially adapted (e.g., reinforced) to serve as a tether. Where appropriate, a flexboard or other electrical interconnection member between a deflectable member and a catheter body may also serve as a tether (e.g., such an arrangement could be employed in catheter 224 of FIGS. 18A and 18B).

Figure 19A:
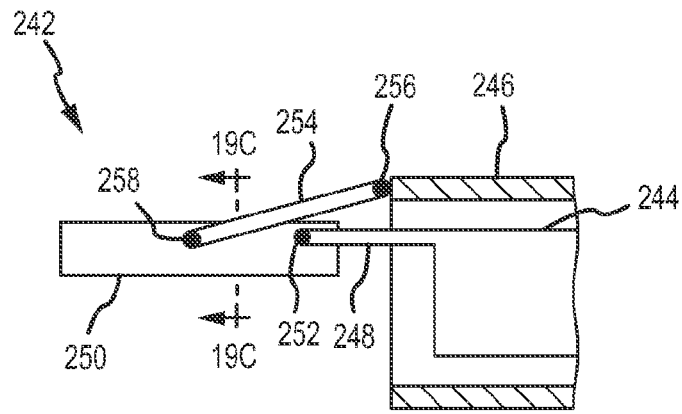
FIGS. 19A, 19B and 19C demonstrate a further embodiment wherein an ultrasound array is deflectable.
Figure 19B:
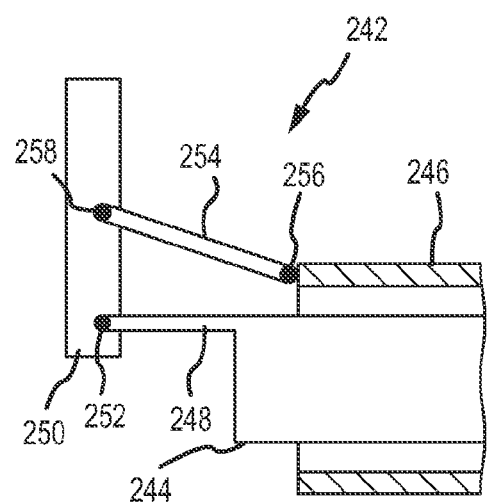
Figure 19C:
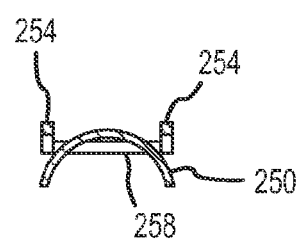

FIGS. 19A-19C illustrate a catheter 242 that includes an inner tubular body 244 and an outer tubular body 246. An inner tubular body extension 248 extends from a distal end of the inner tubular body 244. The inner tubular body extension 248 is pivotably interconnected to an array support 250 via an inner body to array support pivot 252. The inner tubular body extension 248 is generally rigid enough to be able to pivot the array support 250 as described below. The array support 250 may support an ultrasound imaging array (not shown in FIGS. 19A-19C). The array support 250 may be operable to pivot relative to the inner tubular body extension 248 about the inner body to array support pivot 252. The catheter 242 may also include a tether 254. The tether may be of sufficient rigidity to not substantially buckle as the array support 250 is pivoted. The tether 254 may include two individual members (only one of the members is visible in FIGS. 19A and 19B due to one of the members position parallel to and directly behind the other member). On a first end, the tether 254 may be pivotably interconnected to the outer tubular body 246 via an outer body to tether pivot 256. On a second end, the tether 254 may be pivotably interconnected to the array support 250 via a tether to array support 258. As shown in FIG. 19C (a cross sectional view of FIG. 19A along section lines 19C), the two members of the tether 254 may be disposed on each end of the tether to array support 258. The array support 250 may be curved and the tether to array support 258 may pass through corresponding holes in the array support 250. The other pivots 252, 256 may be similarly configured. The inner tubular body extension 248 may be configured similarly to the tether 254 in that it may also be made up of two members that straddle the array support 250 and interconnect to two ends of the inner body to array support pivot 252.

To pivot the array support 250 relative to the inner and outer tubular bodies 244, 246, the inner tubular body 244 is moved along a common central axis relative to the outer tubular body 246. As illustrated in FIGS. 19A and 19B, this relative motion, in combination with the tether's 254 maintenance of a fixed distance between the pivot 258 on the array support 250 and the pivot 256 on the outer tubular body 246, causes the array support 250 to rotate about the inner body to array support pivot 252 until, as shown in FIG. 19B, the array support is substantially perpendicular to the common central axis of the inner and outer tubular bodies 244, 246. Moving the inner tubular body 244 in the opposite direction causes the array support 250 to pivot back into the position shown in FIG. 19A. It will be appreciated that the inner tubular body 244 may be extended beyond the position illustrated in FIG. 19B such that the array support 250 is pivoted through an angle greater than 90 degrees. In an embodiment, the array support 250 may be pivotable through an angle approaching 180 degrees such that the open portion of the array support 250 is generally pointing upwards (e.g., in a direction opposite to that shown in FIG. 19A).

The catheter 242 may also include a tip portion (not shown) that may be molded over the array support 250, an ultrasound imaging array, and any other appropriate components. Any appropriate electrical interconnection, such as those described herein, may be used with the catheter 242 of FIGS. 19A through 19C.

In a variation of the embodiment of FIG. 19A, the inner tubular body extension 248 may be replaced with an outer tubular body extension of a similar configuration but part of the outer tubular body 246 instead of the inner tubular body 244. In such a variation, the outer tubular body extension may be rigidly fixed to the outer tubular body 246 and permanently positioned similar to the tether 254. In such a variation, the outer tubular body extension may be pivotably interconnected to the array support 250 in any appropriate manner. Such a pivotable interconnection may be disposed toward the proximate end of the array support 250 (e.g., the end closest to the inner tubular body 244). A link may be disposed between the proximate end of the array support 250 and the inner tubular body 244 such that when the inner tubular body 244 is advanced relative to the outer tubular body 246, the array support 250 pivots about the pivotable interface between the outer tubular body extension and the array support 250.

Figure 20A:
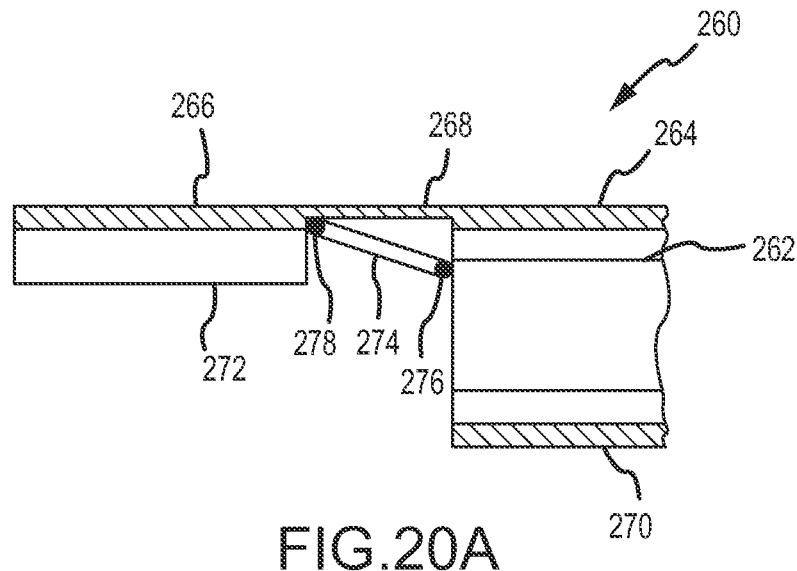
FIGS. 20A and 20B demonstrate a further embodiment wherein an ultrasound array is deflectable.
Figure 20B:
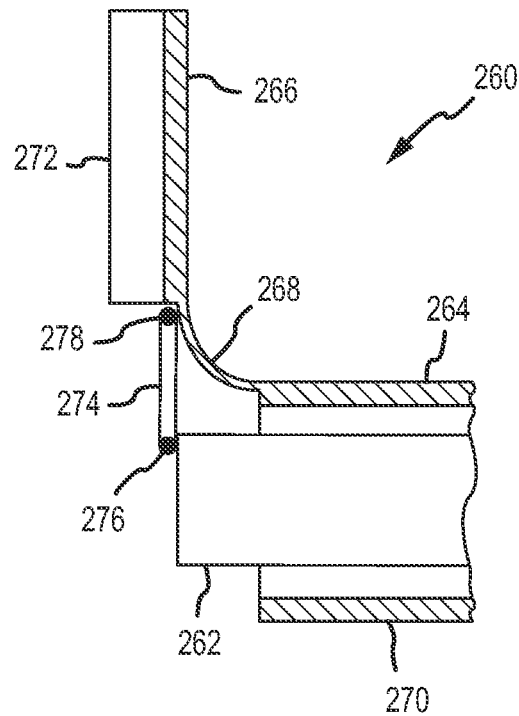

FIGS. 20A and 20B illustrate a catheter 260 that includes an inner tubular body 262 and an outer tubular body 264. The outer tubular body 264 includes a support portion 266 and a hinge portion 268 disposed between the support portion 266 and a tubular portion 270 of the outer tubular body 264. The hinge portion 268 may generally position the support portion 266 such that the support portion 266 is aligned with the tubular portion 270 as shown in FIG. 20A. The hinge portion 268 may be resilient in that it may impart a return force when deflected from the aligned position. For example, the hinge portion 268 may urge the support portion 266 back to the position shown in FIG. 20A when it is disposed in the position shown in FIG. 20B. The hinge portion 268 may be an appropriately sized portion of the outer tubular body 264 and/or it may include additional material such as a support member (e.g., to increase stiffness). An ultrasound imaging array 270 may be interconnected to the support portion 266. A link 274 may be disposed between the inner tubular body 262 and the support portion 266. The link 274 may be adequately rigid to resist buckling. The link 274 may be attached to the inner tubular body 262 via an inner tubular body to link pivot 276. The link 274 may be attached to the support portion 266 via a support portion to link pivot 278.

To pivot the support portion 266 and its attached ultrasound imaging array 272 relative to the inner and outer tubular bodies 262, 264, the inner tubular body 262 is moved along a common central axis relative to the outer tubular body 264. As illustrated in FIGS. 20A and 20B, this relative motion, in combination with the link's 274 maintenance of a fixed distance between the pivots 276, 278 causes the support portion 266 to rotate until, as shown in FIG. 20B, the array support is substantially perpendicular to the common central axis of the inner and outer tubular bodies 262, 264. Moving the inner tubular body 262 in the opposite direction causes the support portion 266 to pivot back into the position shown in FIG. 20A.

The catheter 260 may also include a tip portion (not shown) that may be molded over the support portion 266 and the ultrasound imaging array 272, and any other appropriate components. Any appropriate electrical interconnection, such as those described herein, may be used with the catheter 260 of FIGS. 20A and 20B.

In a first variation of the embodiment of FIG. 20A, link 274 may be replaced with bendable member fixedly attached to the support portion 266 on one end and the inner tubular body 262 on the other end. Such a bendable member may bend when the inner tubular body 244 is advanced relative to the outer tubular body 246 and allow for the support portion to be pivoted as shown in FIG. 20B. In a second variation of the embodiment of FIG. 20A, the support portion 266 and hinge portion 268 may be replaced by a separate member that may be configured similarly to, for example, supports 160, 168, 174 and/or 180, with the modification that the respective tubular body interface portion be sized and configured to be attached to the outer tubular body 264. The first and second variations may be incorporated singularly or both may be incorporated into an embodiment.

Figure 21:
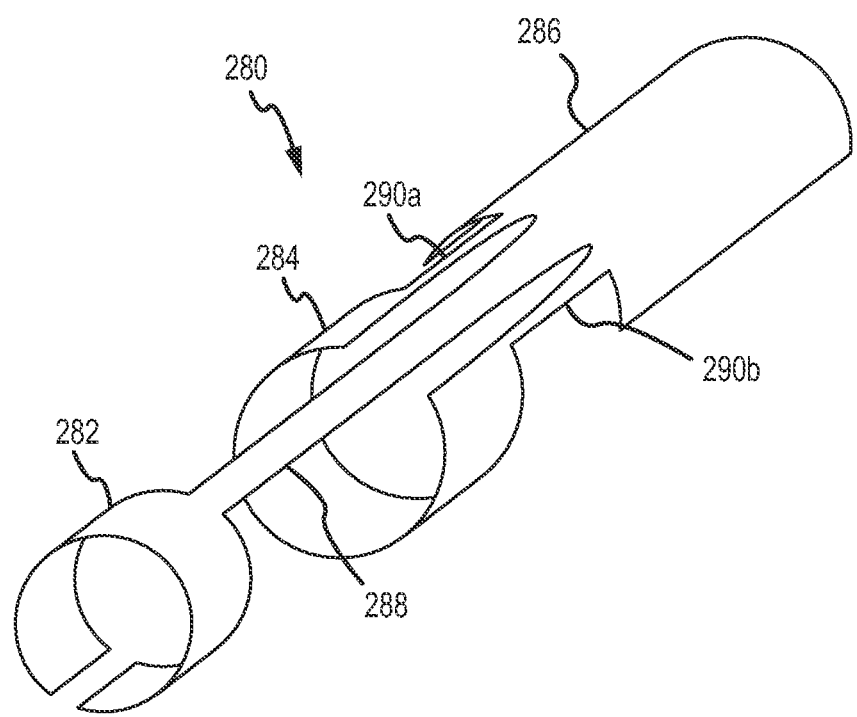
FIG. 21 illustrates an alternative support design.

FIG. 21 illustrates a support 280 that may be used in a catheter, where the catheter includes an inner tubular body, an outer tubular body and an ultrasound imaging array. The support 280 includes a proximal tubular body interface portion 282 that is capable of being attached to an inner tubular body using any appropriate method of attachment such as, for example, clamping and/or gluing. The support 280 further includes a distal tubular body interface portion 284 that is capable of being attached to an outer tubular body using any appropriate method of attachment. The support 280 further includes an array support portion 286 for supporting an ultrasonic imaging array. The support 280 further includes two links: a first link 288 and a second link. The second link includes two parts, link 290a and link 290b. The support 280 may be configured such that when the proximal tubular body interface portion 282 is moved relative to the distal tubular body interface portion 284, the array support portion 286 may pivot relative to a common axis of the proximal tubular body interface portion 282 and the distal tubular body interface portion 284. Such action may be achieved by selecting appropriate relative widths and/or shapes of the links 288, 290a, 290b. In an alternate arrangement of the support 280, the proximal tubular body interface portion 282 may be attached to an outer tubular body and the distal tubular body interface portion 284 may attached to an inner tubular body. In such an embodiment, the proximal tubular body interface portion 282 and the distal tubular body interface portion 284 would be sized to attach to the outer and inner tubular bodies, respectively.

Figure 22A:
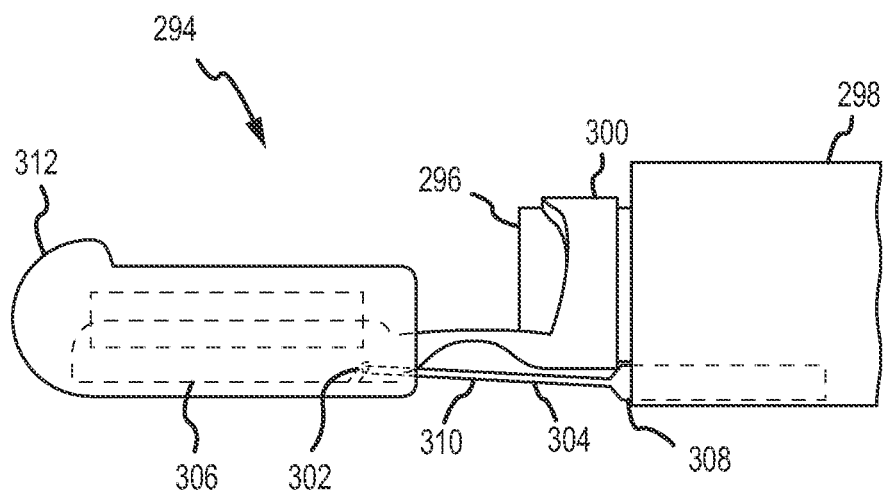
FIGS. 22A and 22B demonstrate a further embodiment wherein an ultrasound array is deflectable.
Figure 22B:
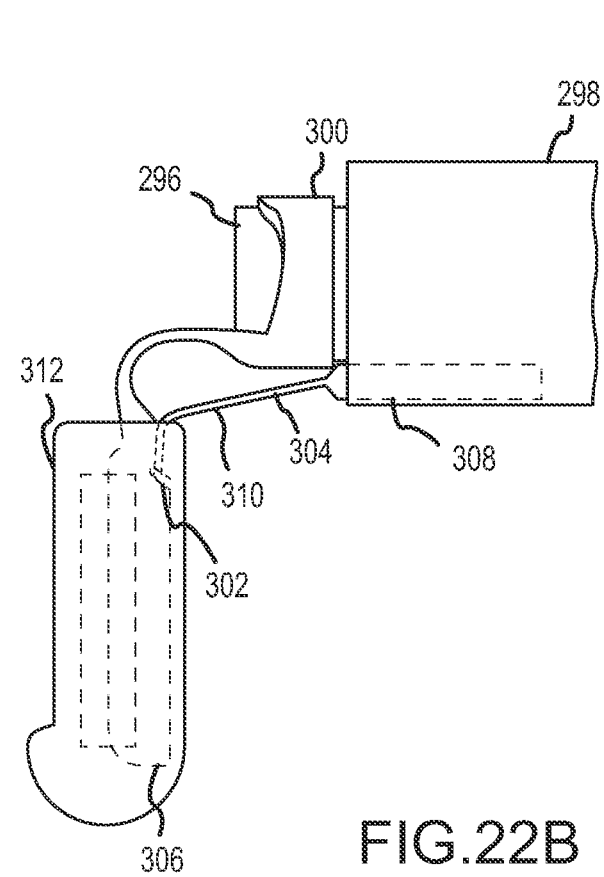

FIGS. 22A and 22B illustrate a catheter 294 that includes an inner tubular body 296 and an outer tubular body 298. Attached to the inner tubular body 296 is a support 300. The support 300 may be configured similarly to the support 74 of FIGS. 5B-5D with the addition of a notch 302. The catheter 294 may further include a tether 304 that interconnects the outer tubular body 298 to a cradle portion 306 of the support 300. Functionally, the tether 304 may perform a similar function to the tether 78 of FIGS. 5B-5D. The tether 304 may, for example, be formed from a flat ribbon (e.g., a flattened tube) including high strength toughened fluoropolymer (HSTF) and expanded fluorinated ethylene propylene (EFEP). The tether 304 may be configured such that it includes a flat portion 308 and a densified portion 310. The densified portion 310 of the tether 304 may be formed by twisting the tether 304 in the area to be densified and then heating the tether 304. The densified portion 310 may be generally round in cross section. Alternatively, the densified portion 310 may have a generally rectangular cross section, or a cross section having any other appropriate shape. In this regard, the flat portion 308 may be disposed between appropriate layers of the outer tubular body 298 without unacceptably affecting the diameter and/or shape of the outer tubular body 298, while the densified portion 310 may be generally round, which may, for example, aid in insertion and positioning within the notch 302 and help to avoid interference with other components (e.g., an electrical interconnection member and/or the support 300).

The notch 302 may be configured to accept the densified portion 310 of the tether 304 such that the densified portion 310 is hooked on to the notch 302. Accordingly, the notch 302 may be configured such that its opening is generally further away from the outer tubular body 298 than the deepest portion of the notch 302 where the tether 304 may tend to occupy.

Since the tether 304 will generally be in tension during deflection of the cradle portion 306, the tether 304 may tend to remain within the notch 302. A tip 312 may be formed over the cradle portion 306 and as such may aid in retention of the densified portion 310 within the notch 302. As noted, the support 300 may be configured similarly to the support 74 of FIGS. 5B-5D and as such may be actuated in a similar manner (e.g., by motion of the inner tubular body 296 relative to the outer tubular body 298 and a corresponding bend of the support 300 as shown in FIG. 22B). The catheter 294 may also include any other appropriate components. Any appropriate electrical interconnection scheme, such as those described herein, may be used with the catheter 294 of FIGS. 22A and 22B.

Figure 23A:
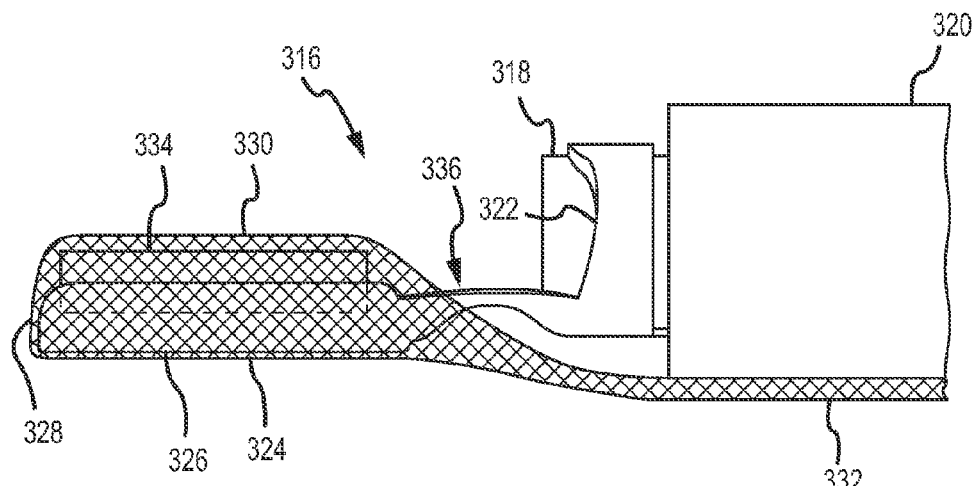
FIGS. 23A and 23B demonstrate a further embodiment wherein an ultrasound array is deflectable.
Figure 23B:
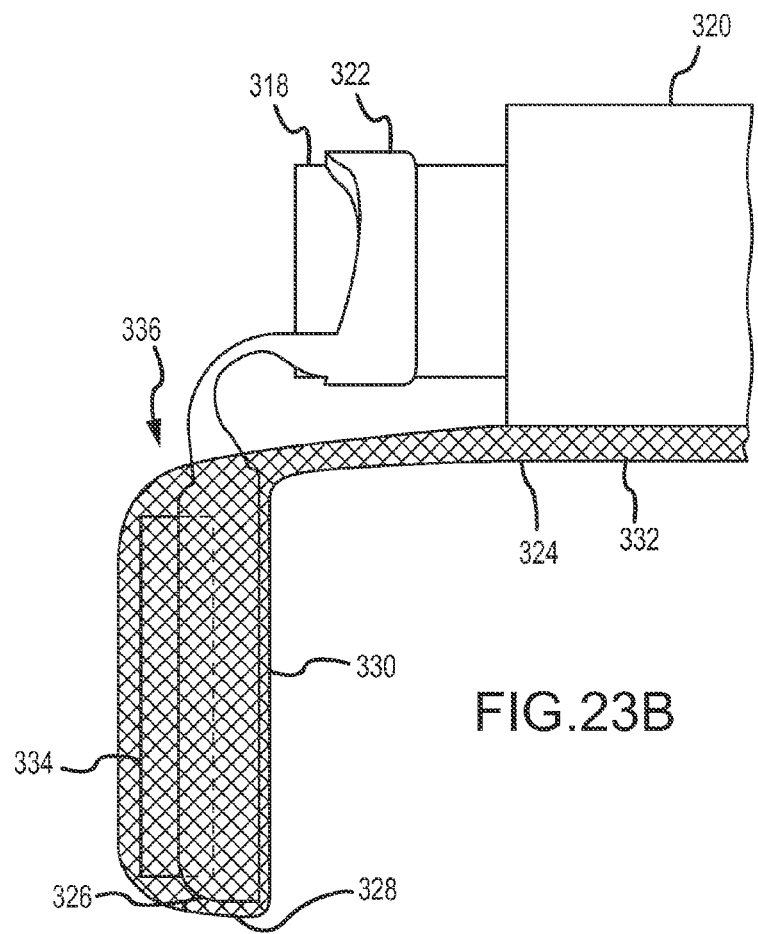

FIGS. 23A and 23B illustrate a catheter 316 that includes an inner tubular body 318 and an outer tubular body 320. Attached to the inner tubular body 318 is a support 322. The support 322 may be configured similarly to the support 74 of FIGS. 5B-5D. The catheter 316 may further include a tether sock 324 that functions to cause a cradle portion 326 of the support 322 to deflect (as shown in FIG. 23B) relative to the inner tubular body 318 when the inner tubular body 318 is moved relative to the outer tubular body 320. In this regard, the tether sock 324 performs a similar function as tether 78 of FIGS. 5B-5D. The tether sock may 324 may be generally tubular with a closed end 328. Once installed in the catheter 316, the tether sock 324 may include a tubular portion 330 and a collapsed portion 332. The tubular portion 330 may envelop the cradle portion 326 and an ultrasound imaging array 334. Alternatively, the tubular portion 330 may envelop the cradle portion 326 without covering the ultrasound imaging array 334. The collapsed portion 332 may generally be in the form of a collapsed tube and may be secured to the outer tubular body 320 in any appropriate manner. Between the tubular portion 330 and the collapsed portion 332, the tether sock 324 may include an opening 336. The opening 334 may be formed by, for example, cutting a slit into the tubular tether sock 324 prior to installation in the catheter 316. Such installation may include passing the cradle portion 326 through the opening 336 to dispose the cradle portion 326 within the closed end 328 of the tether sock 324. The remaining tether sock 324 (the portion of the tether sock 326 not disposed around the cradle portion 326) may be collapsed to form the collapsed portion 332 and attached to the outer tubular body 320 in any appropriate manner. The tether 324 may, for example, be formed from a material that includes a layer of HSTF sandwiched between two EFEP layers. The catheter 316 may also include any other appropriate components. Any appropriate electrical interconnection scheme, such as those described herein, may be used with the catheter 316 of FIGS. 23A and 23B.

Figure 24A:
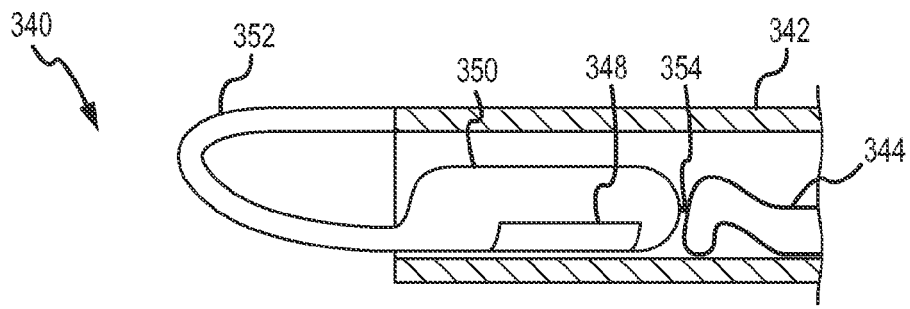
FIGS. 24A, 24B and 24C demonstrate a further embodiment of a catheter wherein an ultrasound array is deployable from within the catheter.
Figure 24B:
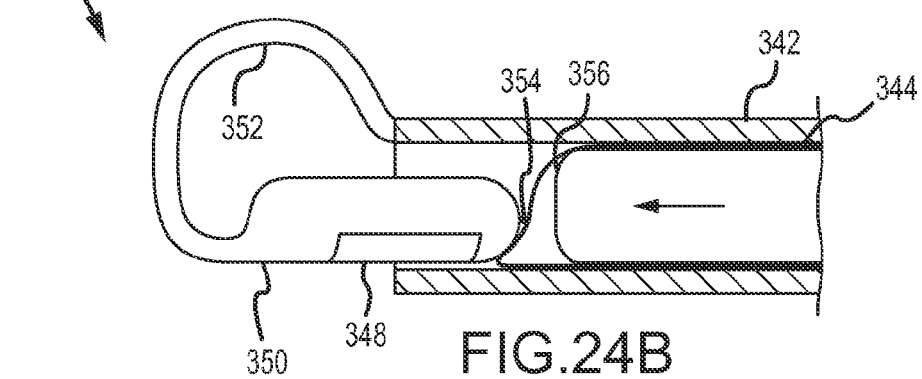
Figure 24C:
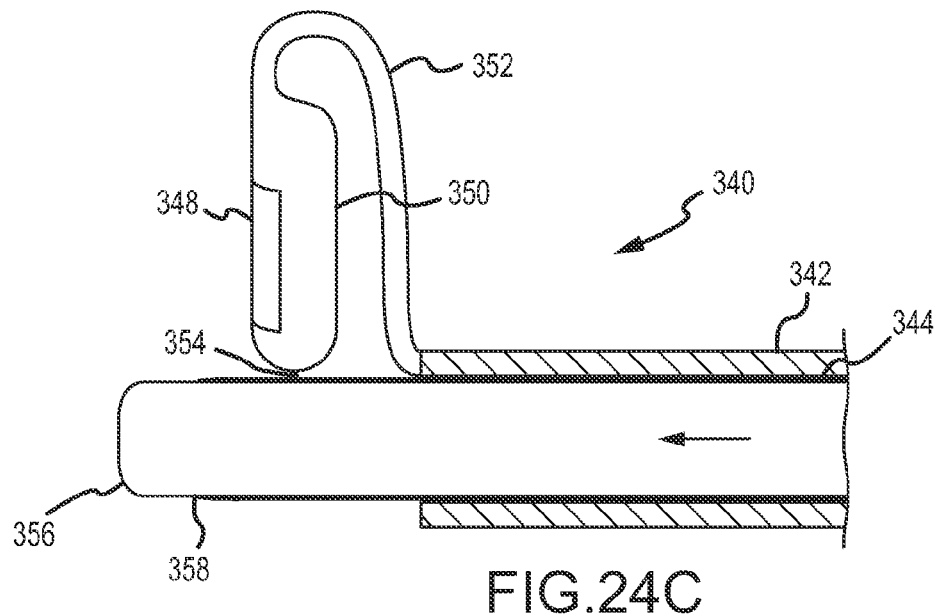

FIGS. 24A-24C illustrate a catheter 340 that includes an outer tubular body 342 and a collapsible inner lumen 344. In FIGS. 24A-24C, the collapsible inner lumen 344 and the outer tubular body 342 are shown in cross section. All other illustrated components of the catheter 340 are not shown in cross section.

While being inserted into a patient, the catheter 340 may be configured as shown in FIG. 24A with an ultrasound imaging array 348 disposed within the outer tubular body 342. The ultrasound imaging array 348 may be disposed within a tip portion 350. The ultrasound imaging array 348 may be electrically and mechanically interconnected to the outer tubular body 342 via a loop 352. The collapsible inner lumen 344 may be in a collapsed state while the tip portion 350 is disposed within the outer tubular body 342 as illustrated in FIG. 24A. The collapsible inner lumen 344 may be interconnected to the tip portion 350 by a joint 354. While in the position illustrated in FIG. 24A, the ultrasound imaging array 348 may be operable and thus images may be generated to aid in positioning of the catheter 340 before and/or during insertion of an interventional device 356.

FIG. 24B illustrates the catheter 340 as the interventional device 356 is displacing the tip portion 350. In this regard, as the interventional device 356 is advanced through the collapsible inner lumen 344, the interventional device 356 may push the tip portion 350 out of the outer tubular body 342.

Figure 25A:
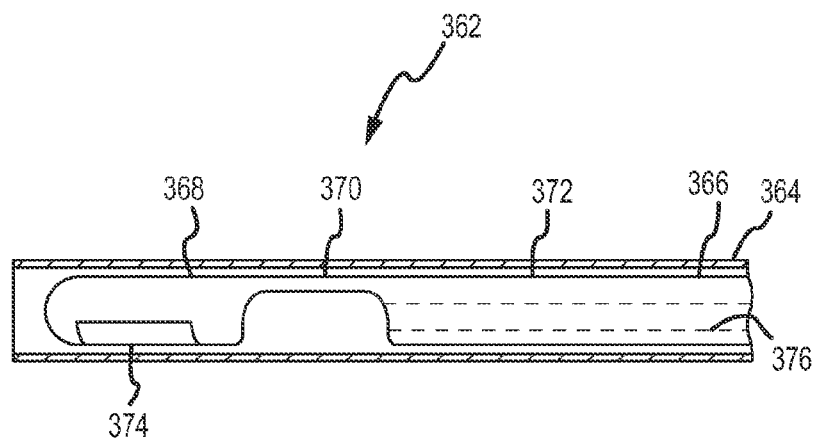
FIGS. 25A and 25B demonstrate a further embodiment of a catheter wherein an ultrasound array is deployable from within the catheter.
Figure 25B:
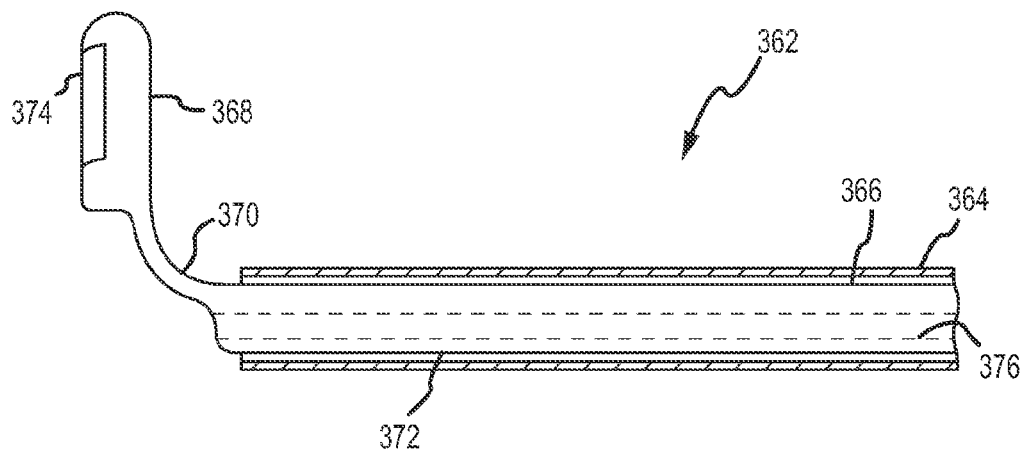

FIG. 24C illustrates the catheter 340 after the interventional device 356 has been pushed through an opening 358 at the end of the collapsible inner lumen 344. The tip portion 350 may remain interconnected to the collapsible inner lumen 344 by virtue of the joint 354 between the two components. Once the interventional device 356 is extended through the opening 358, the ultrasonic imaging array 348 may be generally forward facing (e.g., facing in a distal direction relative to the catheter 340). Such positioning may be facilitated by an appropriately configured loop 352. The ultrasound imaging array 348 may remain electrically interconnected through appropriate cabling in the loop 352. The catheter 340 may also include any other appropriate components FIGS. 25A and 25B illustrate a catheter 362 that includes an outer tubular body 364 and an inner member 366. In FIGS. 25A and 25B, the outer tubular body 364 is shown in cross section. All other illustrated components of the catheter 362 are not shown in cross section. The inner member 366 may include a tip portion 368 and an intermediate portion 370 disposed between the tip portion 368 and a tube portion 372 of the inner member 366. The intermediate portion 370 may be configured such that it positions the tip portion 368 at about a right angle relative to the tube portion 372 (as illustrated in FIG. 25B) in the substantial absence of externally applied forces. In this regard, when the tip portion 368 is disposed within the outer tubular body 364, the outer tubular body 364 may contain the tip portion 368 such that the tip portion 368 remains aligned with the tube portion 372 as illustrated in FIG. 25A. In certain embodiments, the end of the outer tubular body 364 may be structurally reinforced to aid in retaining the tip portion 368 in alignment with the tube portion 372 while the tip portion 368 is disposed therein. The tip potion 368 may include an ultrasound imaging array 374. The tip portion 368 may also house an electrical interconnection member (not shown) electrically interconnected to the ultrasound imaging array 374. The electrical interconnection member may continue through the intermediate portion 370 and then along the inner member 366. The inner member 366 may also include a lumen 376 therethrough. Although illustrated as a single element, the tip portion 368, the intermediate portion 370, and the tube portion 372 may be discrete portions that are interconnected during an assembly process. In this regard, the intermediate portion 370 may be constructed from a shape memory material (e.g., Nitinol) with the memorized configuration including a 90 degree bend to position the tip portion 368 as shown in FIG. 25B.

In use, the catheter 362 may be inserted into a patient with the tip portion 368 disposed within the outer tubular body 364. Once the catheter 362 is in a desired position, the inner member 366 may be advanced relative to the outer tubular body 364 and/or the outer tubular body 364 may be retracted such that the tip portion 368 is no longer disposed within the outer tubular body 364. Accordingly, the tip portion 368 may move to the deployed position (illustrated in FIG. 25B) and the ultrasound imaging array 374 may be used to generate images of a volume distal to the catheter 362. An interventional device (not shown) may be advanced through the lumen 376.

Figure 25C:
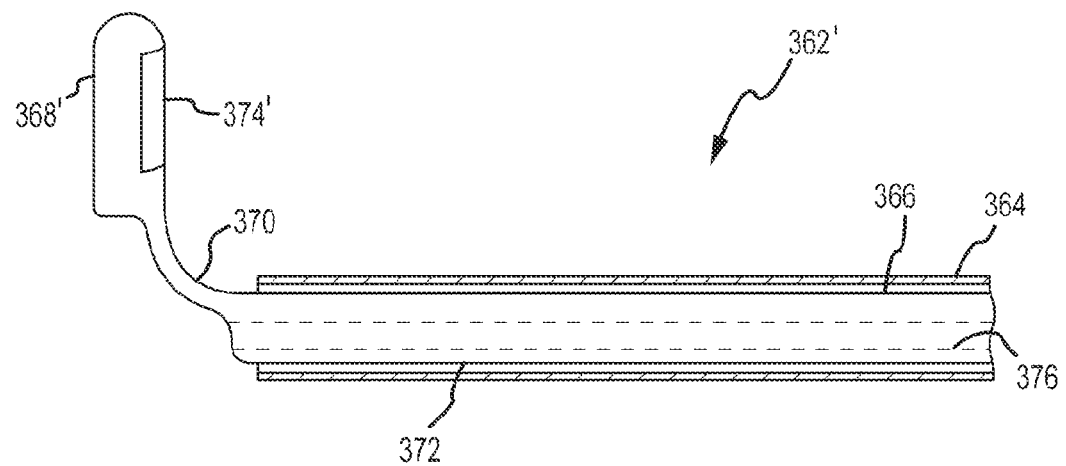
FIG. 25C demonstrates a further embodiment of a catheter wherein an ultrasound array is deployable from within the catheter to a rearward-looking position.

FIG. 25C illustrates a catheter 362' similar to catheter 362 of FIGS. 25A and 25B with a differently positioned ultrasound imaging array 374'. The ultrasound imaging array 374' is disposed on the tip portion 368' such that upon deflection of the tip portion 368', the ultrasound imaging array 374' may be pivoted into an at least partially rearward-looking position. The rearward-looking ultrasound imaging array 374' may be in place of the ultrasound imaging array 374 of FIGS. 25A and 25B, or it may be in addition to the ultrasound imaging array 374 of FIGS. 25A and 25B.

Where appropriate, other embodiments described herein may include ultrasound imaging arrays that may be displaced into rearward-looking positions. These may be in place of or in addition to the disclosed ultrasound imaging arrays. For example, the embodiment illustrated in FIG. 1 may include an ultrasound imaging array that may be displaced into an at least partially rearward-looking position.

Figure 26A:
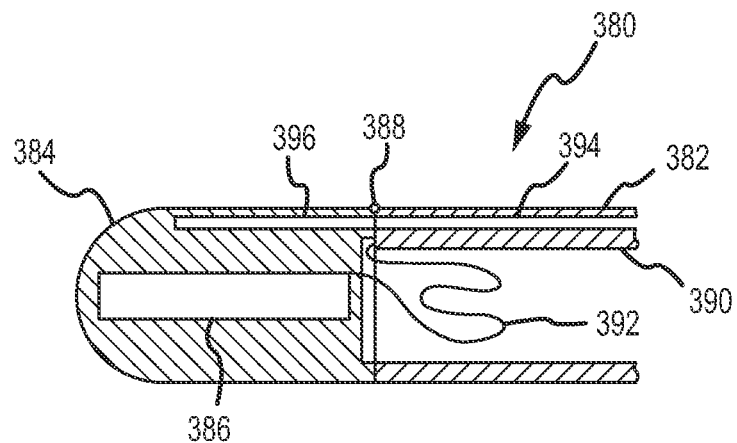
FIGS. 26A and 26B demonstrate a further embodiment of a catheter wherein a tip portion is temporarily bonded to a tubular body.
Figure 26B:
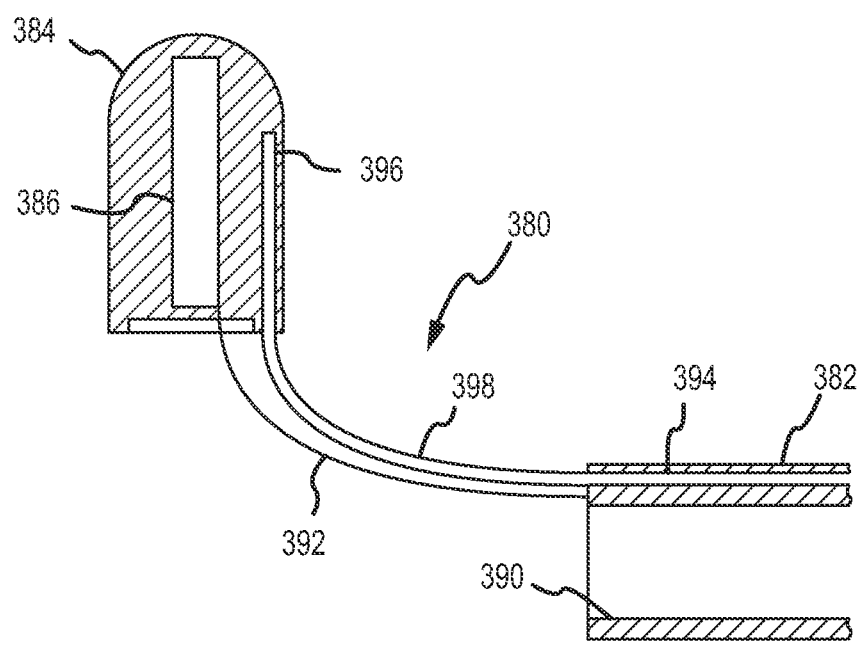

FIGS. 26A and 26B illustrate a catheter 380 that includes a tubular body 382 and a tip 384. In FIGS. 26A and 26B, the tubular body 382 and tip are shown in cross section. All other illustrated components of the catheter 380 are not shown in cross section. The tip 384 may include an ultrasound imaging array 386. The tip 384 may, for example, be fabricated by overmolding the tip 384 over the ultrasound imaging array 386. The tip 384 may be temporarily interconnected to the tubular body 382 by a temporary bond 388 to keep the tip 384 secured while the catheter 380 is inserted into a patient. The temporary bond 388 may, for example, be achieved by an adhesive or a severable mechanical link. Any other appropriate method of achieving a severable bond may be used for the temporary bond. To aid in insertion, the tip 384 may have a rounded distal end. The tubular body 382 includes a lumen 390 for the introduction of an interventional device or other appropriate device (not shown). The catheter 380 also includes a cable 392 that electrically interconnects the ultrasound imaging array 386 in the tip 384 to an electrical interconnection member (not shown) within the wall of the tubular body 382. While the tip is temporarily attached to the tubular body 382, the cable 392 may be disposed within a portion of the lumen 390, as illustrated in FIG. 26A. The tubular body 382 may include a tubular body channel 394 running along the length of the tubular body 382. A corresponding tip channel 396 may be disposed within the tip 384. Together, the tubular body channel 394 and the tip channel 396 may be configured to accept an actuation member, such as a flat wire 398. The flat wire 398 may be configured such that it positions the tip 384 at about a right angle relative to the tubular body 382 (as illustrated in FIG. 26B) in the substantial absence of externally applied forces. In this regard, the flat wire 398 may be constructed from a shape memory material (e.g., Nitinol) with the memorized configuration including a 90 degree bend as shown in FIG. 25B. Moreover, the flat wire 398 may be configured such that it is operable to be advanced through the tubular body channel 394 and the tip channel 396.

In use, the catheter 380 may be inserted into a patient with the tip 384 temporarily bonded to the tubular body 382. While in the position illustrated in FIG. 26A, the ultrasound imaging array 386 may be operable and thus images may be generated to aid in positioning of the catheter 380 during catheter 380 insertion. Once the catheter 380 is in a desired position, the flat wire 398 may be advanced relative to the tubular body 382 and into the tip through the tubular body channel 394 and the tip channel 396. Once the flat wire 398 contacts the end of the tip channel 396 (and/or once friction between the flat wire 398 and the tip 384 reaches a predeterminable threshold), additional insertion force applied to the flat wire 398 may cause the temporary bond 388 to fail and release the tip 384 from the tubular body 382. Once released, further advancement of the flat wire 398 relative to the tubular body 382 may result in pushing the tip 384 away from the tubular body 382. Once free from the tubular body 382, the section of flat wire 398 between the tip 384 and the tubular body 382 may return to a memorized shape which may cause the tip 384 to displaced as illustrated in FIG. 26B. In such a position, the ultrasound imaging array 386 may be used to generate images of a volume distal to the catheter 380. An interventional device (not shown) may be advanced through the lumen 376. Furthermore, the force required to break the temporary bond 388 may be selected such that the flat wire 398 ends up being press fit into the tip channel 396 to a degree that allows a subsequent retraction of the flat wire 398 to draw the tip 384 proximate to the end of the tubular body 382 for further positioning and/or removal of the catheter 380 from the patient.

Figure 27A:
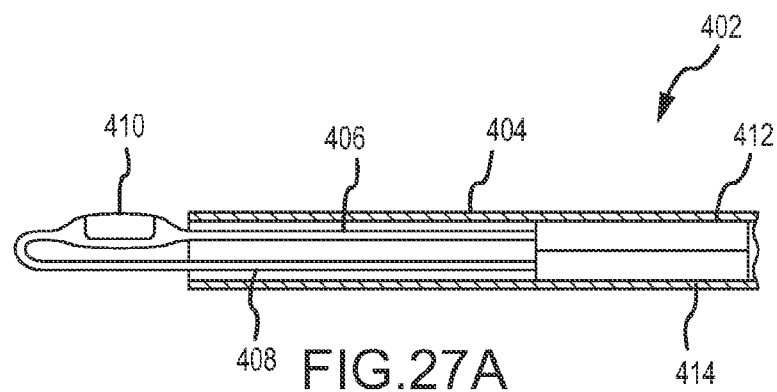
FIGS. 27A, 27B and 27C illustrate a further embodiment of a catheter wherein an ultrasound array is movable via a pair of cables.
Figure 27B:
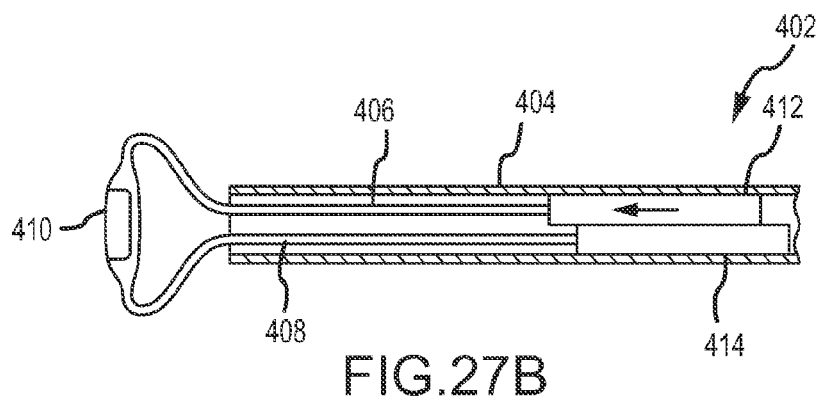
Figure 27C:
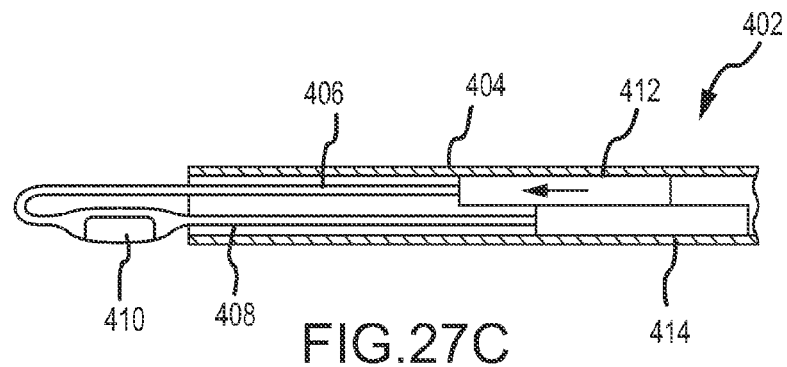

FIGS. 27A through 27C illustrate a catheter 402 that includes a tubular body 404. In FIGS. 27A through 27C, the tubular body 404 is shown in cross section. All other illustrated components of the catheter 402 are not shown in cross section. Disposed within a portion of the tubular body 404 are a first control cable 406 and a second control cable 408. The first and second control cables 406, 408 are operatively interconnected to opposite ends of an ultrasound imaging array 410. The control cables 406, 408 each have an appropriate level of stiffness such that, by moving the first control cable 406 relative to the second control cable 408, the position of the ultrasound imaging array 410 relative to the tubular body 404 may be manipulated. As shown in FIG. 27A, the control cables 406, 408 may be disposed such that the ultrasound imaging array 410 is pointed in a first direction (upward as shown in FIG. 27A). By moving the first control cable 406 in a distal direction relative to the second control cable 408, the ultrasound imaging array 410 may be adjusted to point in a distal direction (as shown in FIG. 27B). By moving the first control cable 406 still further in a distal direction relative to the second control cable 408, the ultrasound imaging array 410 may be adjusted to point in direction opposite form the first direction (downward as shown in FIG. 27C). It will be appreciated that any position between the illustrated positions may also be achieved. It will also be appreciated that the above described positions of the ultrasound imaging array 410 may be achieved by relative movement of the control cables 406, 408 and as such, may be achieved by anchoring either control cable 406, 408 relative to the tubular body 404 and moving the other of the control cables or by moving both control cables 406, 408 simultaneously. At least one of the control cables 406, 408 may contain electrical conductors to electrically interconnect to the ultrasound imaging array 410.

The first control cable 406 may be attached to a first half rod 412. The second control cable 408 may be attached to a second half rod 414. The half rods 412, 414 may each be half cylinders configured such that when proximate to each other, they form a cylinder about equal in diameter to the inner diameter of the tubular body 404. The half rods 412, 414 may be made of flexible and/or lubricious material (e.g., PTFE) and may be operable to flex along with the tubular body 404 (e.g., while the catheter 402 is disposed within the patient). The half rods 412, 414 may be disposed proximate to the distal end of the catheter 402, and the second half rod 414 may be fixed relative to the tubular body 404, while the first half rod 412 remains movable relative to the tubular body 404. Moreover, an actuator (not shown), such as a flat wire or the like, may be attached to the first half rod 412 and run along the length of the tubular body 404 to enable a user move the first half rod 412 relative to the second half rod 414 and thus manipulate the position of the ultrasound imaging array 410.

The repositioning of the ultrasound imaging array 410 has been described as a result of moving the first half rod 412 while the second half rod 414 remains stationary relative to the tubular body 404. In alternate embodiments, the ultrasound imaging array 410 may be repositioned by moving the second half rod 414 while the first half rod 412 remains stationary or by moving both the first half rod 412 and the second half rod 414 simultaneously, sequentially or a combination of simultaneously and sequentially.

Figure 28A:
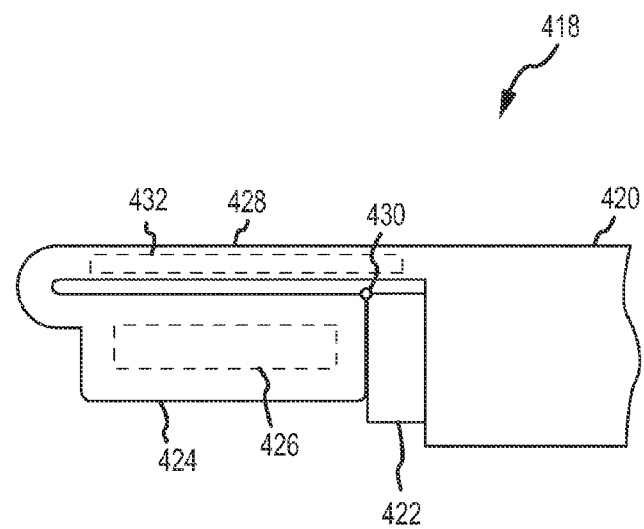
FIGS. 28A and 28B demonstrate a further embodiment of a catheter that is pivotably interconnected to an inner tubular body.
Figure 28B:
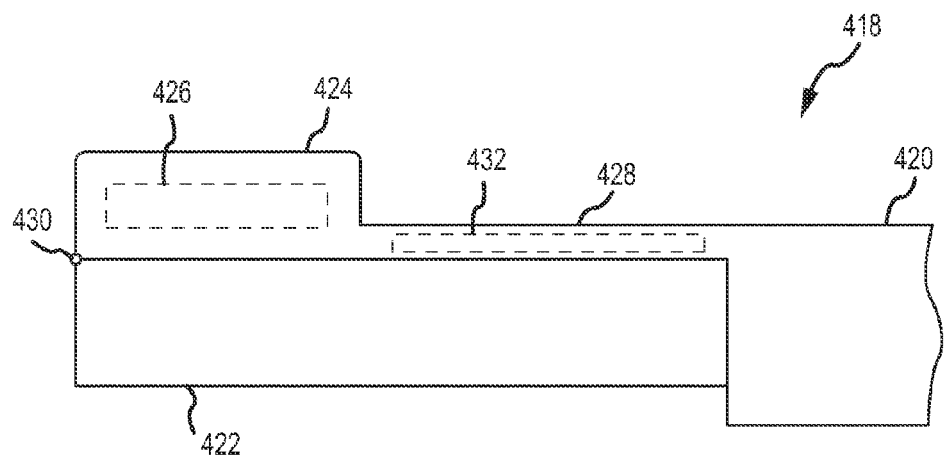

FIGS. 28A and 28B illustrate a catheter 418 that includes an outer tubular body 420 and an inner tubular body 422. The inner tubular body 422 may include a lumen therethrough. The catheter 418 also includes a tip portion 424 that includes an ultrasound imaging array 426. The tip portion 424 is interconnected to the outer tubular body 420 by a tip support 428. The tip support 428 may include an electrical interconnection member (e.g., flexboard, cable) to electrically interconnect to the ultrasound imaging array 426. Although illustrated as a single piece, the outer tubular body 420, the tip support 428, and the tip portion 424 may each be separate components that are joined together in an assembly process. One end of the tip portion 424 may be joined to the tip support 428 and the other end may be joined to the distal end of the inner tubular body 422 at a hinge 430. The hinge 430 may allow the tip portion 424 to rotate about the hinge 430 relative to the inner tubular body 422. The tip support 428 may be of a uniform or non-uniform predetermined stiffness to facilitate the positioning as illustrated in FIG. 28A (e.g., axial alignment of the tip portion 424 with the inner tubular body 422). The tip support 428 may include a shape memory material.

In the embodiment of FIGS. 28A and 28B and all other appropriate embodiments described herein, the hinge 430 or other appropriate hinge may be a live hinge and may be constructed from any appropriate material (e.g., the hinge may be a polymeric hinge). The hinge 430 or other appropriate hinge may be a true hinge and may include multiple components such as pins and corresponding holes and/or loops.

During insertion into a patient, the catheter 418 may be arranged as in FIG. 28A with the tip portion 424 in axial alignment with the inner tubular body 422 and a field of view of the ultrasound imaging array 426 pointing perpendicular to the longitudinal axis of the catheter 418 (downward as illustrated in FIG. 28A). In this regard, the catheter 418 may be substantially contained within a diameter equal to the outer diameter of the outer tubular body 420. As desired, the tip portion 424 may be pivoted relative to the inner tubular body 422 to vary the direction of the field of view of the ultrasound imaging array 426. For example, by moving the inner tubular body 422 distally relative to the outer tubular body 420, the tip portion 424 may be pivoted to the position illustrated in FIG. 28B such that the field of view of the ultrasound imaging array 426 is pointing upward. It will be appreciated that positions between those illustrated in FIGS. 28A and 28B may be achieved during rotation, including a position where the tip portion 424 is disposed vertically (relative to the position illustrated in FIGS. 28A and 28B) and the field of view of the ultrasound imaging array 426 is pointing distally. It will also be appreciated that once the tip portion 424 is disposed vertically, the distal end of the lumen of the inner tubular body 422 will be clear from obstruction by the tip portion 424 and an interventional device may then be inserted through the lumen.

In a variation of the embodiment of FIGS. 28A and 28B, the inner tubular body may be a collapsible lumen. In such an embodiment, introduction of the interventional device may be used to deploy the tip portion 424 to a distally looking position and subsequent retraction of the collapsible lumen may be used to return the tip portion 424 to the position of FIG. 28A.

In another variation of the embodiment of FIGS. 28A and 28B, the tip support 428 may include a stiffening member 432. The stiffening member 432 may be configured such that it remains straight during deployment of the catheter 418. As such, during pivoting of the tip portion 424, the tip support 428 may substantially only bend in the regions between the stiffening member 432 and the tip portion 424 and between the stiffening member 432 and the outer tubular body 420.

Figure 29A:
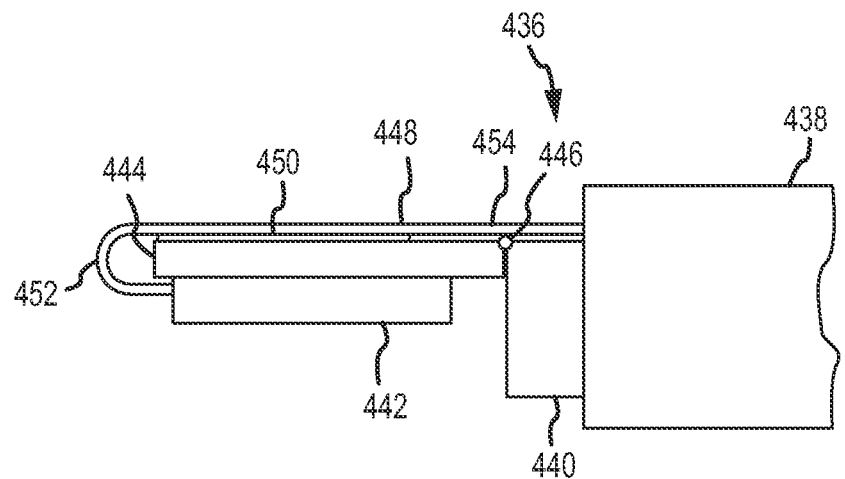
FIGS. 29A and 29B demonstrate another embodiment of a catheter that is pivotably interconnected to an inner tubular body.
Figure 29B:
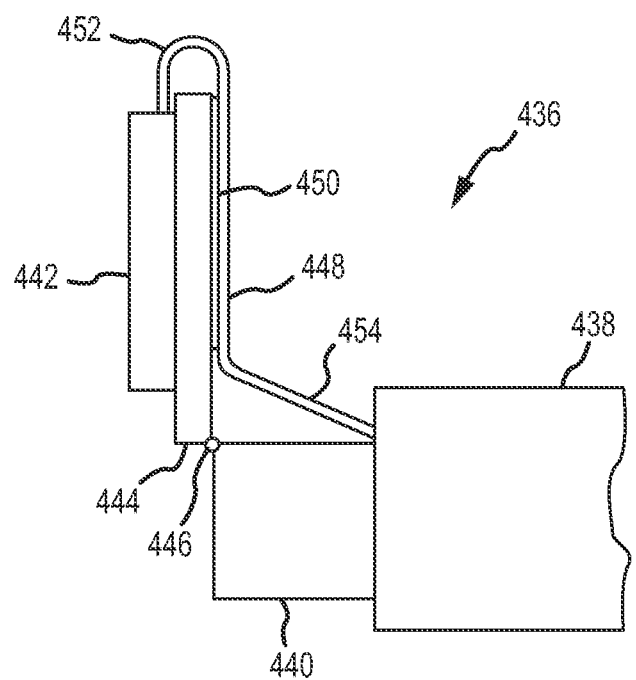

FIGS. 29A and 29B illustrate a catheter 436 that includes an outer tubular body 438 and an inner tubular body 440. The inner tubular body 440 may include a lumen therethrough. The catheter 436 also includes an ultrasound imaging array 442 interconnected to a tip support 444. The tip support 444 is interconnected to the distal end of the inner tubular body 440 at a hinge 446. The hinge 446 may allow the tip support 444 to rotate about the hinge 446 relative to the inner tubular body 440. An electrical interconnection member 448 may electrically interconnect to the ultrasound imaging array 442. The electrical interconnection member 448 is connected to a distal end of the ultrasound imaging array 442. The electrical interconnection member 448 may be bonded or otherwise fixed to a portion 450 of the tip support 444 on an opposite side of the tip support from the ultrasound imaging array 442. The electrical interconnection member 448 may include a loop 452 between the connection to the ultrasound imaging array 442 and the bonded portion 450. The bonded portion 450, by virtue of its fixed position relative to the tip support 444 may serve as a strain relief preventing strain associated with pivoting of the ultrasound imaging array 442 from being translated to the loop 452 and array 442 through the electrical interconnection member 448. A tether portion 454 of the electrical interconnection member 448 may be disposed between the bonded portion 450 and the point where the electrical interconnection member 448 enters into the outer tubular body 436. The tether portion 454 may be an unmodified portion of the electrical interconnection member 448 or it may be modified (e.g., structurally reinforced) to accommodate additional forces due to its serving as a tether. The tip support 444 and the ultrasound imaging array 442 may be encased or otherwise disposed within a tip (not shown).

During insertion into a patient, the catheter 436 may be arranged as in FIG. 29A with the ultrasound imaging array 442 in axial alignment with the inner tubular body 440 and a field of view of the ultrasound imaging array 442 pointing perpendicular to the longitudinal axis of the catheter 436 (downward as illustrated in FIG. 29A). In this regard, the catheter 436 may be substantially contained within a diameter equal to the outer diameter of the outer tubular body 438. As desired, the ultrasound imaging array 442 may be pivoted relative to the inner tubular body 440 by moving the inner tubular body 440 distally relative to the outer tubular body 438. Such relative motion will cause the ultrasound imaging array 442 to pivot about the hinge 446 due to the restraint of motion of the ultrasound imaging array 442 by the tether portion 454. The ultrasound imaging array 442 may be returned to the position illustrated in FIG. 29A by moving the inner tubular body 440 proximally relative to the outer tubular body 438.

Figure 30A:
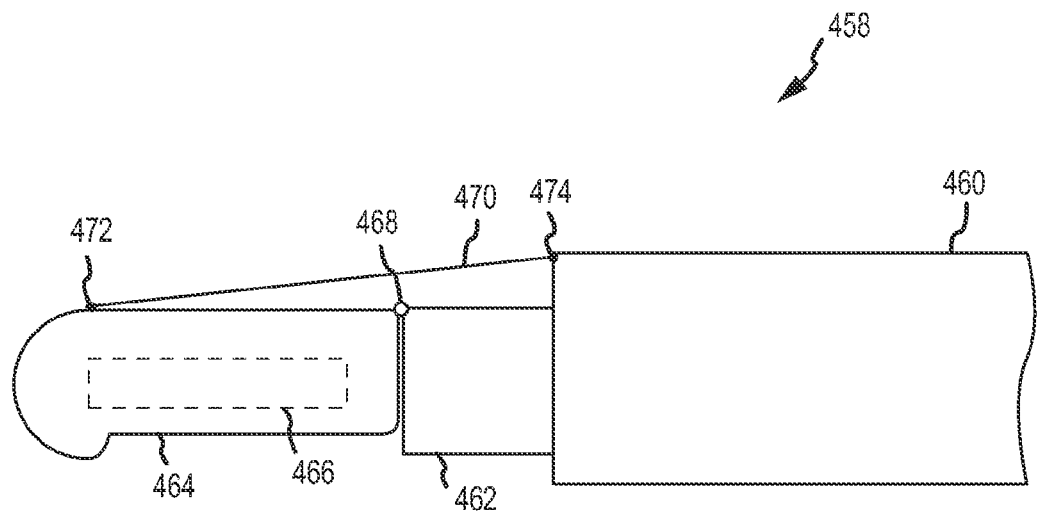
FIGS. 30A and 30B demonstrate yet another embodiment of a catheter that is pivotably interconnected to an inner tubular body.
Figure 30B:
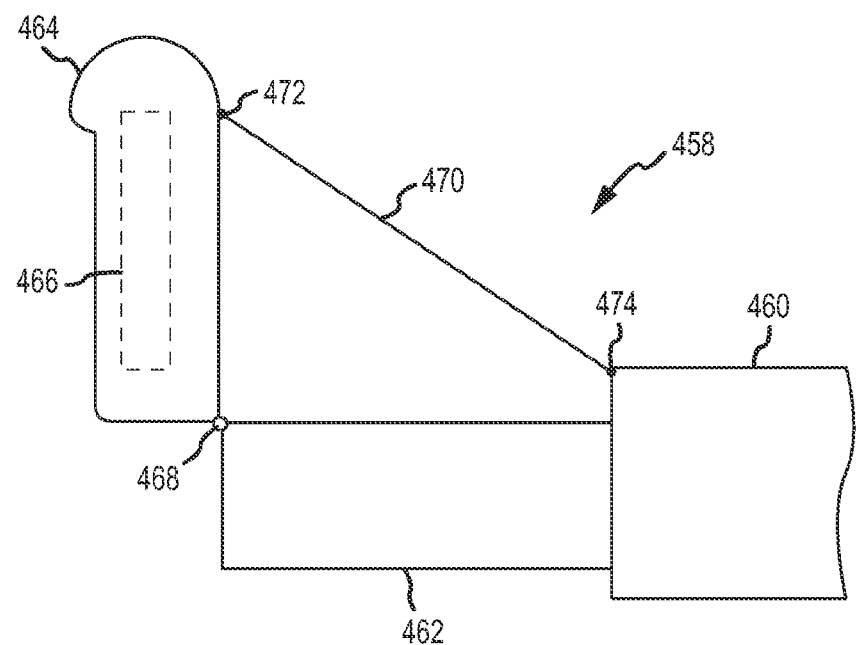

FIGS. 30A and 30B illustrate a catheter 458 that includes an outer tubular body 460 and an inner tubular body 462. The inner tubular body 462 may include a lumen therethrough. The catheter 458 also includes an ultrasound imaging array 466 disposed within a tip portion 464. The tip portion 464 is interconnected to the distal end of the inner tubular body 462 at a hinge 468. The hinge 468 may allow the tip portion 464 to rotate about the hinge 468 relative to the inner tubular body 462. The catheter 458 may further include a tether 470. The tether 470 may be anchored to a distal region of the tip portion 464 at tip anchor point 472. The tether 470 may be anchored to a distal end of the outer tubular body 460 at an outer tubular body anchor point 474. Any appropriate electrical interconnection scheme, such as those described herein, may be used with the catheter 458 of FIGS. 30A and 30B.

During insertion into a patient, the catheter 458 may be arranged as in FIG. 30A with the tip portion 464 in axial alignment with the inner tubular body 462 and a field of view of the ultrasound imaging array 466 pointing at a right angle to the longitudinal axis of the catheter 458 (downward as illustrated in FIG. 30A). Such positioning of the tip portion 464 may be facilitated by a spring or other appropriate mechanism or component biasing the tip portion 464 toward the position illustrated in FIG. 30A. In this regard, the catheter 458 may be substantially contained within a diameter equal to the outer diameter of the outer tubular body 460. As desired, the tip portion 464 may be pivoted relative to the inner tubular body 462 by moving the outer tubular body 460 proximally relative to the inner tubular body 462. Such relative motion will cause the tip portion 464 to pivot about the hinge 468 due to the restraint of motion of the tip portion 464 by the hinge 468. The tip portion 464 may be returned to the position illustrated in FIG. 30A by moving the outer tubular body 460 distally relative to the inner tubular body 462 and allowing the biasing mechanism or component to return the tip portion 464 to the position illustrated in FIG. 30A. In an alternate embodiment, the tether 470 may possess enough rigidity such that substantially no biasing of the tip portion 464 to the position illustrated in FIG. 30A is needed.

It will be appreciated that the hinges 446, 468 of FIGS. 29A and 30A, respectively (along with, where appropriate, any other hinge discussed herein), may be in the form of live hinges such as the live hinge that is part of the support 174 illustrated in FIG. 14C. It will also be appreciated that the hinges 446, 468 of FIGS. 29A and 30A, respectively, may be in the form of live hinges and array supports that are parts of the inner tubular bodies 440, 462, respectively. Such inner tubular bodies that also serve as supports for the arrays would be similar in configuration to the outer tubular body 264 with support portion 266 illustrated in FIG. 20B.

Figure 31A:
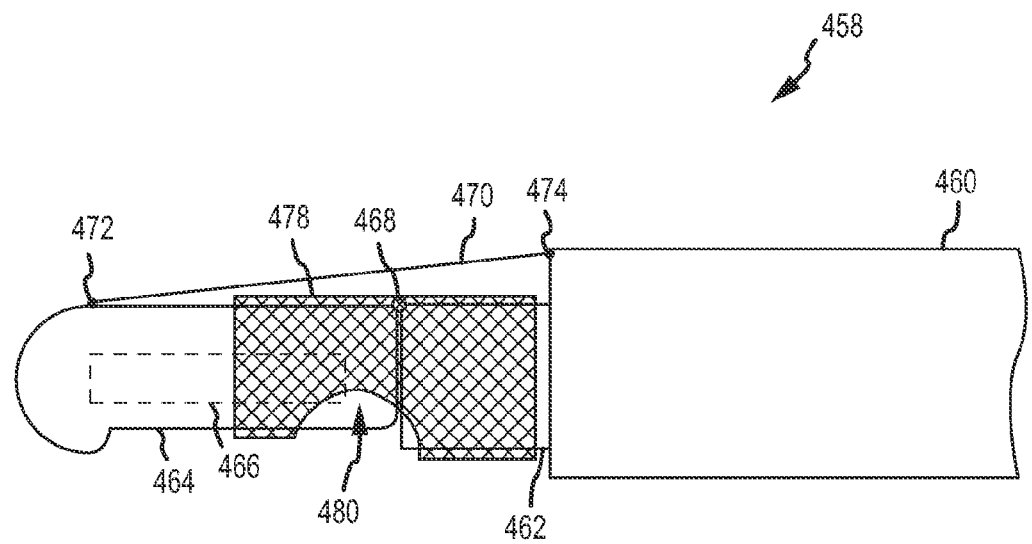
FIGS. 31A and 31B illustrate the embodiment of FIGS. 30A and 30B with the addition of a resilient tube.
Figure 31B:
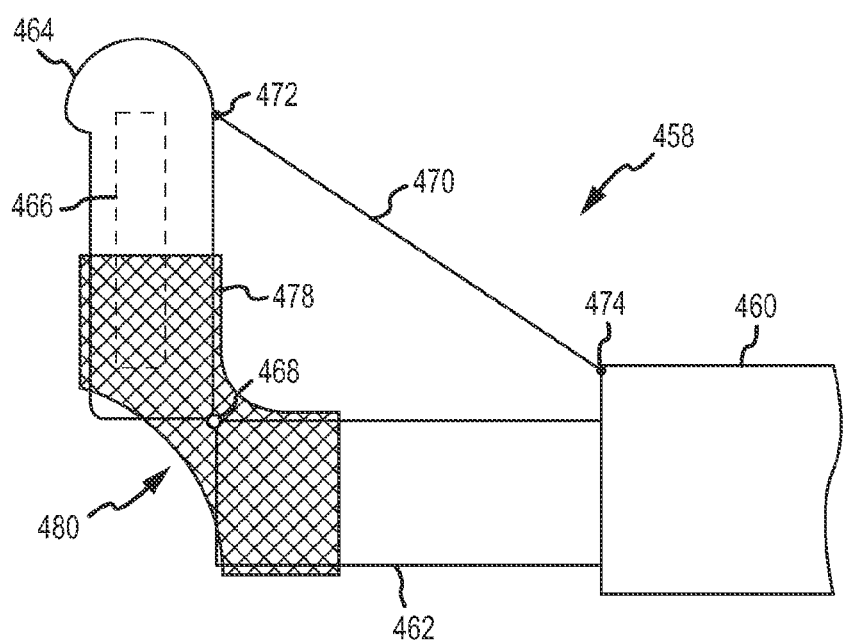

FIGS. 31A and 31B illustrate the catheter 458 and components thereof of FIGS. 30A and 30B with the addition of a resilient tube 478. The resilient tube 478 may act as a biasing mechanism to bias the tip portion 464 toward the position illustrated in FIG. 31A. The resilient tube 478 may also assist in making the catheter 458 more atraumatic to a vessel into which it has been inserted. The resilient tube 478 may include, for example, an elastic material capable of being deformed as shown in FIG. 31B when the tip portion 464 is deflected and returning toward the state illustrated in FIG. 31A once the deflection force has been removed or reduced (e.g., when the outer tubular body 460 is returned to the position relative to the inner tubular body 462 illustrated in FIG. 31A). To preserve the ability to introduce an interventional device through the lumen of the inner tubular body 462, the resilient tube 478 may include an opening 480. When in the position illustrated in FIG. 31B, the opening 480 may align with the lumen and therefore not interfere with an interventional device deployed through the lumen. The resilient tube 478 may be interconnected to the inner tubular body 462 and the tip portion 464 in any appropriate manner, such as for example, shrink fit, bonding, welding, or with an adhesive. Although illustrated as occupying the field of view of the ultrasound imaging array 466, alternatively, the resilient member 478 may be disposed such that it is not within the field of view of the ultrasound imaging array 466. This may be accomplished by reconfiguring the resilient member 478 relative to as illustrated and/or by repositioning the ultrasound imaging array 466 relative to as illustrated. The resilient member 478, or a similar, appropriately modified resilient member, may be used in any suitable embodiment disclosed herein.

Figure 32A:
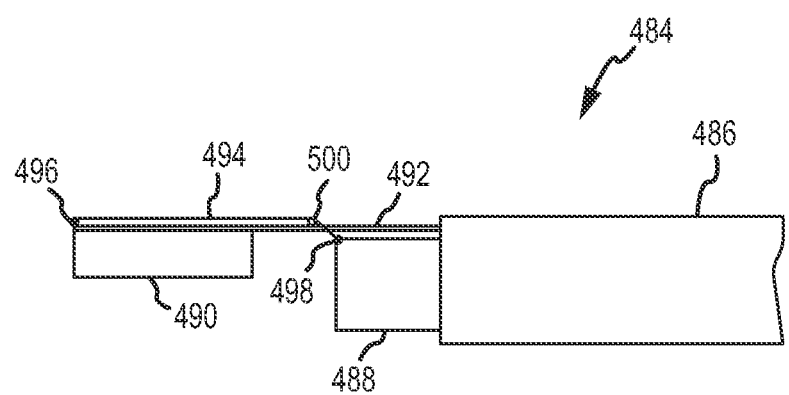
FIGS. 32A and 32B demonstrate a further embodiment of a catheter that includes a buckling initiator.
Figure 32B:
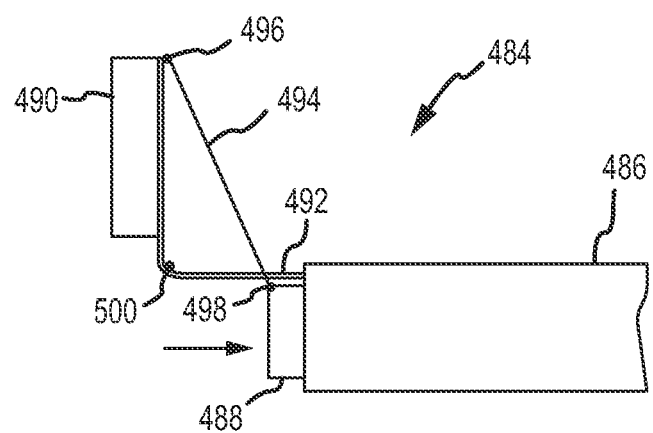

FIGS. 32A and 32B illustrate a catheter 484 that includes an outer tubular body 486 and an inner tubular body 488. The inner tubular body 488 may include a lumen therethrough. The catheter 484 also includes an ultrasound imaging array 490 interconnected to an electrical interconnection member 492. The electrical interconnection member 492 may, for example, be in the form of a flexboard interconnected to a spirally wound electrical interconnection member within the outer tubular body 486 on one end and interconnected to the ultrasound imaging array 490 on the other end. The catheter 484 also includes a tether 494 anchored on one end to a distal end of the electrical interconnection member 492 and/or ultrasound imaging array 490 at a tether to array anchor 496. On the other end, the tether 494 may be anchored to the inner tubular body 488 at a tether to inner tubular body anchor 498. As shown in FIG. 32A, the tether 494 may be disposed such that it bends around a buckling initiator 500 when the ultrasound imaging array 490 is aligned with the inner tubular body 488. The electrical interconnection member 492 may serve both to provide an electrical connection to the ultrasound imaging array 490 and act as a spring member to bias the ultrasound imaging array 490 toward the position illustrated in FIG. 32A (e.g., aligned with the inner tubular body 488). To achieve this, the electrical interconnection member 492 may include a stiffener and/or spring element interconnected to the electrical interconnection member 492 in the region between the ultrasound imaging array 490 and the outer tubular body 486. A tip (not shown) may be molded over the ultrasound imaging array 490.

During insertion into a patient, the catheter 484, with an appropriately configured tip (not shown), may be arranged as in FIG. 32A with the ultrasound imaging array 490 in axial alignment with the inner tubular body 488 and a field of view of the ultrasound imaging array 490 pointing generally perpendicularly from the longitudinal axis of the catheter 484 (illustrated as downward in FIG. 32A). In this regard, the catheter 484 may be substantially contained within a diameter equal to the outer diameter of the outer tubular body 486. As desired, the ultrasound imaging array 490 may be pivoted relative to the inner tubular body 488 by moving the inner tubular body 440 proximally relative to the outer tubular body 486. Such relative motion will place the tether 494 in tension, resulting in a downward force by the tether 494 on the buckling element 500. The downward force may cause the electrical interconnection member 492 to buckle in a controlled manner such that the electrical interconnection member 492 pivots in a clockwise direction (relative to the view of FIG. 32A). Once the buckling has been initiated, continued relative movement of the inner tubular body 488 may result in the ultrasound imaging array 490 pivoting to the forward-looking position shown in FIG. 32B. The ultrasound imaging array 490 may be returned to the position illustrated in FIG. 32A by moving the inner tubular body 488 distally relative to the outer tubular body 438. In such a case, the aforementioned biasing of the electrical interconnection member 492 may result in the ultrasound imaging array 490 returning to the position illustrated in FIG. 32A.

It will be appreciated that, where appropriate, the electrical interconnection members described herein that are disposed between tubular bodies and ultrasound imaging arrays that move relative to those tubular bodies, may be configured to additionally serve as biasing members (such as described above with respect to FIGS. 32A and 32B).

Figure 33A:
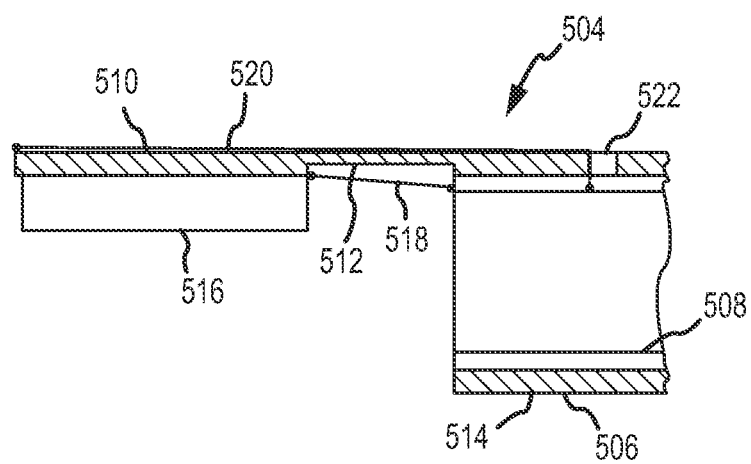
FIGS. 33A and 33B demonstrate a further embodiment of a catheter that includes two tethers.
Figure 33B:
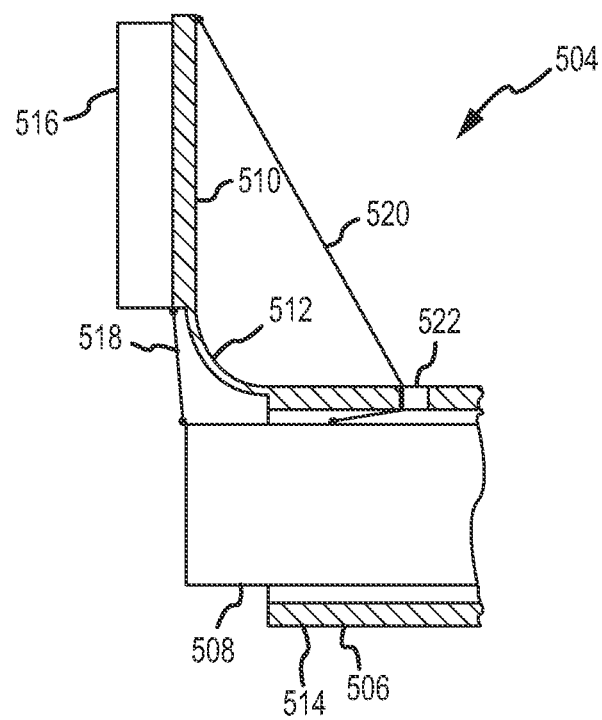

FIGS. 33A and 33B illustrate a catheter 504 that includes an outer tubular body 506 and an inner tubular body 508. The inner tubular body 508 may include a lumen therethrough. In FIGS. 33A and 33B, the outer tubular body 506 is shown in cross section. All other illustrated components of the catheter 504 are not shown in cross section. The outer tubular body 506 includes a support portion 510 and a hinge portion 512 disposed between the support portion 510 and a tubular portion 514 of the outer tubular body 506. The hinge portion 512 may generally restrict the motion of the support portion 510 to pivoting relative to the tubular portion 514 (e.g., pivoting between the position shown in FIG. 33A and the position shown in 33B).

The hinge portion 512 may, as illustrated in FIGS. 33A and 33B, be an appropriately sized portion of the outer tubular body 506 and/or it may include additional material such as a support member (e.g., to increase stiffness). In a variation of the embodiment of FIGS. 33A and 33B, the support portion 510 and hinge portion 512 may be replaced by a separate member that may be configured similarly to, for example, supports 160, 168, 174 and/or 180, with the modification that the respective tubular body interface portion be sized and configured to be attached to the outer tubular body 506.

An ultrasound imaging array 516 may be interconnected to the support portion 510. A first end of a first tether 518 may be interconnected to a distal end of the inner tubular body 508 and a second end of the first tether 518 may be interconnected to a proximal end of the support portion 510. A first end of a second tether 520 may be interconnected to the inner tubular body 508 and a second end of the second tether 520 may be interconnected to a distal end of the support portion 510. The second tether may be threaded through a through hole 522 in the outer tubular body 506.

To pivot the support portion 510 and its attached ultrasound imaging array 516 from the position illustrated in FIG. 33a (e.g., aligned with the inner tubular body 508) to the position illustrated in FIG. 33B (e.g., perpendicular to a longitudinal axis of the catheter 504 and forward looking), the inner tubular body 508 is moved distally relative to the outer tubular body 506. Such movement results in the second tether 520 being drawn into the interior of the outer tubular body 506 through the through hole 522. As the second tether is drawn through the through hole 522, the effective length of the tether between the through hole 522 and the distal end of the support portion 510 is shortened, causing the support portion 510 to pivot. To return the support portion 510 to the position illustrated in FIG. 33A from the position illustrated in FIG. 33B, the inner tubular body 508 is moved proximally relative to the outer tubular body 506. Such movement results in the inner tubular body 508 pulling (by virtue of their interconnection via the first tether 518) the support portion 510 back toward a position where the support portion 510 is aligned with the inner tubular body 508. It will be appreciated that when causing one of the tethers 518, 520 to be in tension due to movement of the inner tubular body 508 relative to the outer tubular body 506, tension will be relieved in the other one of the tethers 518, 520. In an alternative configuration of catheter 504, the first and second tethers 518, 520 may be combined into a single tether anchored along the inner tubular body 508 as shown and threaded along the support portion 510. Such a tether may be anchored to the support portion 510 at a single point.

The catheter 504 may also include a tip portion (not shown) that may be molded over the support portion 510, the ultrasound imaging array 516, and/or any other appropriate components. Any appropriate electrical interconnection, such as those described herein, may be used with the catheter 504 of FIGS. 33A and 33B.

Figure 34A:
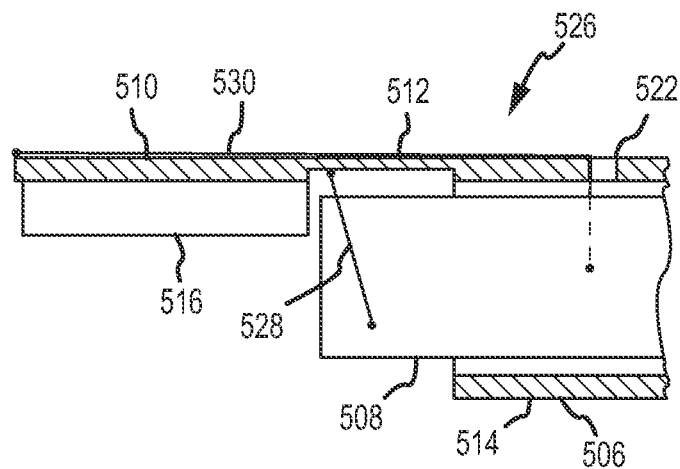
FIGS. 34A and 34B demonstrate a further embodiment of a catheter that includes two tethers partially wrapped about an inner tubular body.
Figure 34B:
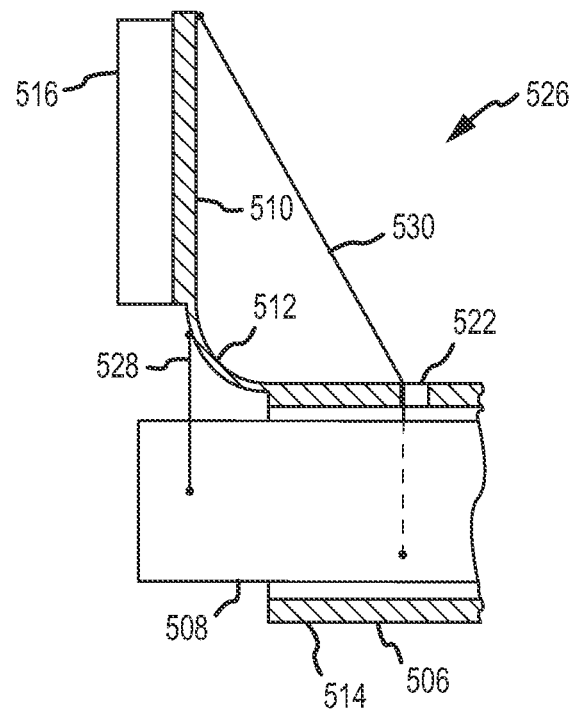

FIGS. 34A and 34B present catheter 526 that is a variation of the catheter 504 of FIGS. 33A and 33B. As such, similar components are similarly numbered and will not be discussed with reference to FIGS. 34A and 34B. A first end of a first tether 528 may be interconnected to a sidewall of the inner tubular body 508 and a second end of the first tether 528 may be interconnected to a distal point on the hinge portion 512. A first end of a second tether 530 may be interconnected to the sidewall of the inner tubular body 508 at a point along the length of the inner tubular body 508 that corresponds to the position of the through hole 522 and a second end of the second tether 520 may be interconnected to a distal end of the support portion 510. The second tether may be threaded through the through hole 522 in the outer tubular body 506. The inner tubular body 508 may be disposed such that a distal portion of it extends distally from the distal end of the outer tubular body 506. The inner tubular body 508 is rotatable relative to the outer tubular body 506.

With the support portion 510 aligned with the tubular portion 514 as shown in FIG. 34A, the tethers 528, 530 may be disposed as follows. The first tether 528 may be at least partially wrapped about and anchored to the outer circumference of the inner tubular body 508. The second tether 530 may be at least partially wrapped about, in a direction opposite from that of the first tether 528, and anchored to the outer circumference of the inner tubular body 508. As illustrated in FIG. 34A, when seen from the perspective of a point distal to the distal end of the inner tubular body 508 and looking toward the distal end of the inner tubular body 508 (hereinafter referred to as an end view), the first tether 528 is partially wrapped about the inner tubular body 508 in a clockwise direction and the second tether 530 is partially wrapped about the inner tubular body 508 in a counterclockwise direction. The tethers 528, 530 may be in the form of cord like members able to transmit tensile forces along their length and to conformally wrap about the inner tubular body 508. In an arrangement, the tethers 528, 530 may be in the form of a spring wound about the inner tubular body 508.

To pivot the support portion 510 and its attached ultrasound imaging array 516 from the position illustrated in FIG. 34a (e.g., aligned with the inner tubular body 508) to the position illustrated in FIG. 34B (e.g., perpendicular to a longitudinal axis of the catheter 526 and forward looking), the inner tubular body 508 is rotated counterclockwise (as seen in an end view) relative to the outer tubular body 506. Such rotation results in the second tether 530 being drawn into the interior of the outer tubular body 506 through the through hole 522 due to its wrapping about the inner tubular body 508. As the second tether is drawn through the through hole 522, the effective length of the tether between the through hole 522 and the distal end of the support portion 510 is shortened, causing the support portion 510 to pivot. Simultaneously, the first tether 528 is being unwrapped from the inner tubular body 508. To return the support portion 510 to the position illustrated in FIG. 34A from the position illustrated in FIG. 34B, the inner tubular body 508 is rotated in a clockwise direction (as seen in an end view) relative to the outer tubular body 506. Such rotation results in the first tether 528 being wrapped about the inner tubular body 508, thus pulling the support portion 510 back toward the position illustrated in FIG. 34A. Simultaneously, the second tether 530 is being unwrapped from the inner tubular body 508. Where the catheter 526 is configured such that the support portion 510 is biased toward the position illustrated in FIG. 34A, the first tether 528 may be unnecessary (e.g., the biasing may be adequate to return the support portion 510 to the position illustrated in FIG. 34A by unwrapping the second tether 530). Along the same lines, where the catheter 526 is configured such that the support portion 510 is biased toward the position illustrated in FIG. 34B, the second tether 530 may be unnecessary (e.g., the biasing may be adequate to move the support portion 510 to the position illustrated in FIG. 34B by unwrapping the first tether 528). Similarly, the first tether 518 of the catheter 504 of FIGS. 33A and 33B may be unnecessary where the support portion 510 is biased toward the position illustrated in FIG. 33A, and the second tether 520 of the catheter 504 of FIGS. 33A and 33B may be unnecessary where the support portion 510 is biased toward the position illustrated in FIG. 33B.

The catheter 526 may also include a tip portion (not shown) that may be molded over the support portion 510, the ultrasound imaging array 516, and/or any other appropriate components. Any appropriate electrical interconnection, such as those described herein, may be used with the catheter 526 of FIGS. 34A and 34B.

Figure 35A:
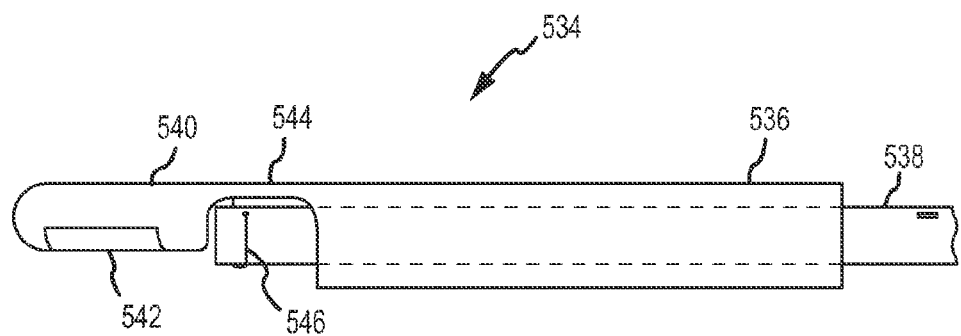
FIGS. 35A and 35B demonstrate a further embodiment of a catheter that is secured in an introductory configuration by a tether wound about an inner tubular body.
Figure 35B:
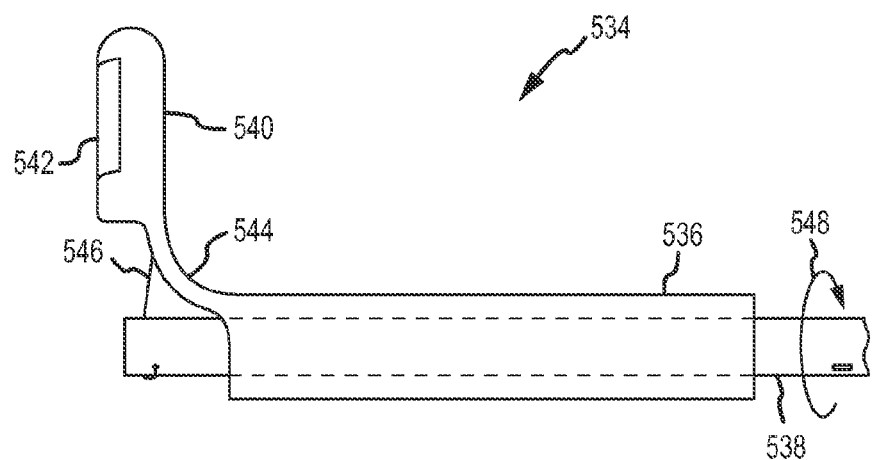

FIGS. 35A and 35B illustrate a catheter 534 that includes an outer tubular body 536 and an inner tubular body 538. The inner tubular body 538 may include a lumen therethrough. The outer tubular body 536 includes a support portion 540 and a hinge portion 544. The hinge portion 544 may be biased such that it generally positions the support portion 540 such that the support portion 540 is at about a right angle relative to the inner tubular body 538 (as illustrated in FIG. 35B) in the substantial absence of externally applied forces. An ultrasound imaging array 542 may be interconnected to the support portion 540. The hinge portion 544 may be an appropriately sized portion of the outer tubular body 536 and/or it may include additional material (e.g., to increase stiffness).

The catheter 534 includes a tether 546 disposed between a distal portion of the hinge portion 544 and the inner tubular body 538. The tether 546 may be at least partially wrapped about and anchored to the outer circumference of the inner tubular body 538. The tether 546 may be in the form of a cord like member able to transmit tensile forces along its length and to conformally wrap about the inner tubular body 538.

To pivot the support portion 540 and its attached ultrasound imaging array 542 from the position illustrated in FIG. 35A (e.g., aligned with the inner tubular body 538) to the position illustrated in FIG. 35B (e.g., perpendicular to a longitudinal axis of the catheter 534 and forward looking), the inner tubular body 538 may be rotated clockwise (as seen in an end view) relative to the outer tubular body 536. Such rotation results in the tether 546 being unwrapped from the inner tubular body 538 and the support portion 540 moving toward the position illustrated in FIG. 35B due to the aforementioned biasing of the hinge portion 544.

To return the support portion 540 to the position illustrated in FIG. 35A from the position illustrated in FIG. 35B, the inner tubular body 538 may be rotated in a counterclockwise direction (as seen in an end view) relative to the outer tubular body 536. Such rotation results in the tether 546 wrapping about the inner tubular body 538, thus pulling the support portion 540 back toward the position illustrated in FIG. 35A.

The catheter 534 may also include any appropriate electrical interconnection to the ultrasound imaging array 542, including appropriate connection schemes described herein. In a variation of the embodiment of FIG. 35A, the support portion 540 and hinge portion 544 may be replaced by a separate member that may be configured similarly to, for example, supports 160, 168, 174 and/or 180, with the modification that the respective tubular body interface portion be sized and configured to be attached to the outer tubular body 536.

In use, the catheter 534 may be inserted into a patient with the support portion 540 aligned with the outer tubular body 536. Once the catheter 534 is in a desired position, the inner tubular body 538 may be rotated relative to the outer tubular body to allow the hinge portion 544 to move the support portion 540 to a desired angle relative to the longitudinal axis of the catheter 534. An interventional device (not shown) may be advanced through the lumen within the inner tubular body 538.

Figure 36A:
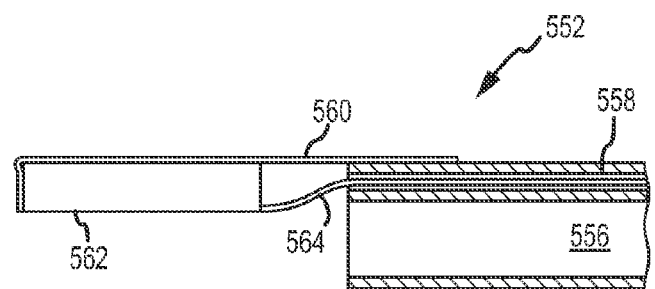
FIGS. 36A through 36C demonstrate a further embodiment of a catheter attached to a pivoting arm and deployable with a push wire.
Figure 36B:
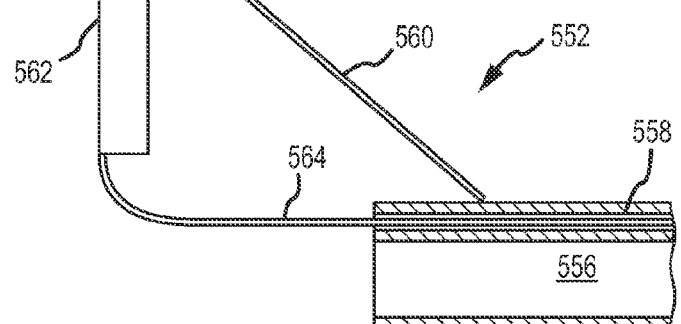
Figure 36C:
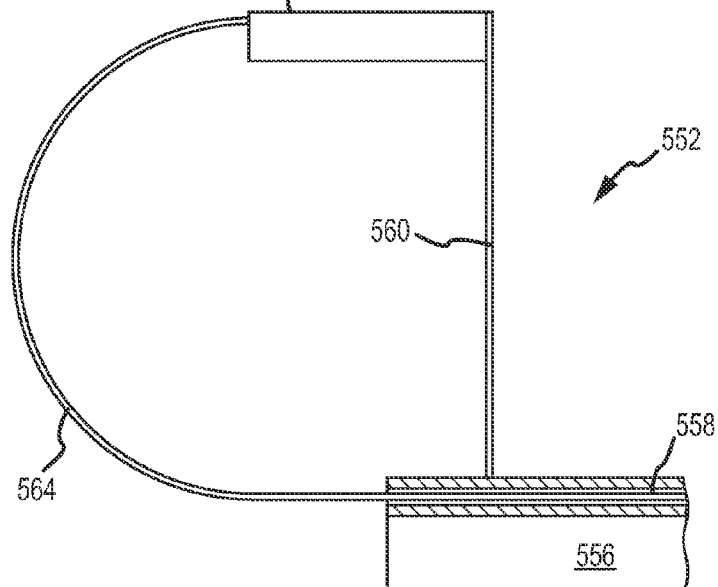

FIGS. 36A through 36C illustrate a catheter 552 that includes a tubular body 554. The tubular body 554 includes a lumen 556 therethrough. The tubular body 554 further includes a channel 558 running through a sidewall of the tubular body 554. A proximal end of an arm 560 is attached to the tubular body 554 in a manner such that the arm 560 may pivot relative to the tubular body 554. The arm 560 may be of sufficient rigidity to allow for the pivoting of an ultrasound imaging array 562 as described below. A distal end of the ultrasound imaging array 562 may be interconnected to a distal end of the arm 560 such that when the ultrasound imaging array 562 is aligned with the tubular body 554, a rear face (pointing upward in the orientation shown in FIG. 36A) of the ultrasound imaging array 562 may be generally parallel to the arm 560. The catheter 552 further includes a push wire 564 running along the channel 558. A distal end of the push wire 564 is interconnected to a proximal end of the ultrasound imaging array 562. The interconnection between the distal end of the push wire 564 and the proximal end of the ultrasound imaging array 562 may be a rigid connection as illustrated in FIGS. 36A through 36C, or it may be a hinged connection or any other appropriate type of connection. The interconnection point between the push wire 564 and the ultrasound imaging array 562 may be disposed closer a front face (pointing downward in the orientation shown in FIG. 36A) of the ultrasound imaging array 562 than to the rear face of the ultrasound imaging array 562. Such disposition may aid in initial displacement of the ultrasound imaging array 562 away from the position illustrated in FIG. 36A by imparting a larger torque on the ultrasound imaging array 562 than would be achieved if the push wire 564 were closer to being collinear with the arm 560.

To pivot the ultrasound imaging array 562 from the position illustrated in FIG. 36A (e.g., aligned with the tubular body 554) to the position illustrated in FIG. 36B (e.g., perpendicular to a longitudinal axis of the catheter 552 and forward looking), the push wire 564 may be advanced relative to the tubular body 554. As illustrated in FIGS. 36A and 36B, this relative motion, in combination with the arm's 560 maintenance of a fixed distance between its attachment point to the tubular body 554 and the distal end of the ultrasound imaging array 562 may result in the ultrasound imaging array 562 pivoting to the forward-looking position of FIG. 36B. It will be appreciated that the push wire 564 should have appropriate column strength to transfer the necessary degree of force to move the ultrasound imaging array 562 as illustrated. To return the ultrasound imaging array 562 to the position illustrated in FIG. 36A from the position illustrated in FIG. 36B, the push wire 564 may be withdrawn.

The catheter 552 may also include any appropriate electrical interconnection to the ultrasound imaging array 562, including appropriate connection schemes described herein. For example, an electrical interconnection member may be disposed along the arm 560 and may electrically interconnect the ultrasound imaging array 562 to an electrical interconnection member disposed within a wall of the tubular body 554. A tip (not shown) may be molded over the ultrasound imaging array 562.

The catheter 552 may be further operable to deploy the ultrasound imaging array 562 to the position illustrated in FIG. 36C where the ultrasound imaging array 562 is facing in a direction substantially opposite from the insertion position illustrated in FIG. 36A. This may be achieved by continuing to advance the push wire 564 relative to the tubular body 554 beyond the position shown in FIG. 36B. It will be appreciated that further advancement of the push wire 564 may yield further pivoting of the ultrasound imaging array 562 beyond that illustrated in FIG. 36C. It will also be appreciated that the ultrasound imaging array 562 may be positioned in any intermediate position between the discussed positions.

Figure 37A:
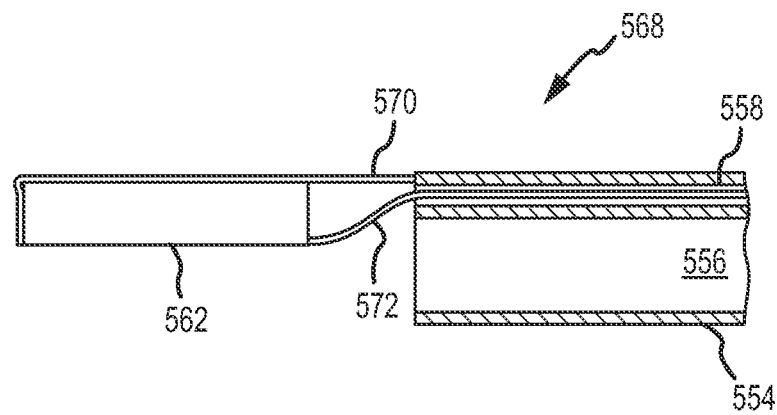
FIGS. 37A and 37B demonstrate a further embodiment of a catheter deployable with a push wire.
Figure 37B:
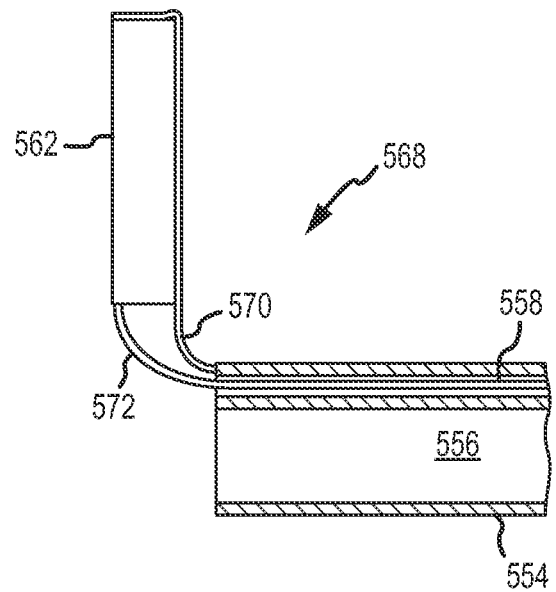

FIGS. 37A and 37B present a catheter 568 that is a variation of the catheter 552 of FIGS. 36A and 36B. As such, similar components are similarly numbered and will not be discussed with reference to FIGS. 37A and 37B. An arm 570 is attached to the distal end of the tubular body 554. The arm 570 may, for example, be in the form of a flexboard that includes electrical conductors for interconnection to the ultrasound imaging array 562. In embodiments where the arm 570 includes a flexboard, the flexboard may include reinforcing or other members to facilitate the use of the flexboard as described below (e.g., use as a hinge). The arm 570 may be of sufficient flexibility to allow for the pivoting of an ultrasound imaging array 562 as described below. The arm 570 may be connected to the ultrasound imaging array 562 along the rear face of the ultrasound imaging array 562. The catheter 568 further includes a push wire 572 running along the channel 558. A distal end of the push wire 572 is interconnected to a proximal end of the ultrasound imaging array 562 as in catheter 552 of FIGS. 36A and 36B.

To pivot the ultrasound imaging array 562 from the position illustrated in FIG. 37A to the position illustrated in FIG. 37B, the push wire 572 may be advanced relative to the tubular body 554. As illustrated in FIGS. 37A and 37B, this relative motion, in combination with the arm's 570 flexibility may result in the ultrasound imaging array 562 pivoting to the forward-looking position of FIG. 37B. To return the ultrasound imaging array 562 to the position illustrated in FIG. 37A from the position illustrated in FIG. 37B, the push wire 572 may be withdrawn. A tip (not shown) may be molded over the ultrasound imaging array 562.

Figure 38A:
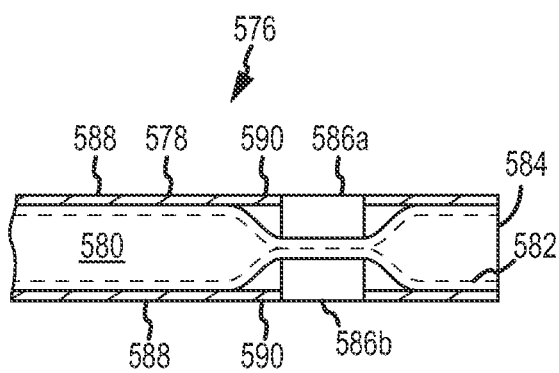
FIGS. 38A and 39B demonstrate two further embodiments of catheters with ultrasound imaging arrays deployed on a plurality of arms.
Figure 38B:
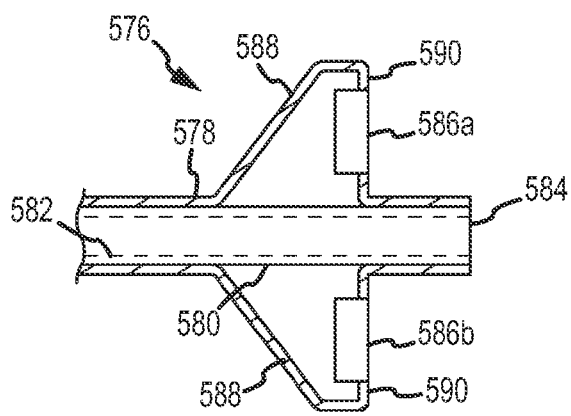

FIGS. 38A and 38B present a catheter 576 that is configured somewhat similarly to the catheters of FIGS. 7A through 8D in that relative movement of components can cause a deflectable portion of an outer tubular body 578 to deflect an ultrasound imaging array to a forward-looking position. In the case of the catheter 576, the ultrasound imaging array may include a first imaging array 586a and a second imaging array 586b. As illustrated in FIG. 38A, an introductory configuration (e.g., the configuration of the catheter 576 as it is introduced into a patient) of the catheter 576 includes the first and second imaging arrays 586a, 586b in a back-to-back relationship, with an at least partially collapsed inner tubular body 580 between the imaging arrays 586a, 586b. The inner tubular body 580 may include a lumen 582 therethrough. The outer tubular body 578 and the inner tubular body 580 may be fixed relative to each other at a single point at a distal end 584 of the catheter 576.

To move the imaging arrays 586a, 586b from the positions illustrated in FIG. 38A (e.g., side-looking) to the positions illustrated in FIG. 38B (e.g., forward-looking), a proximal end of the outer tubular body 578 may be pushed distally while maintaining the position of the inner tubular body 580 (and/or a proximal end of the inner tubular body 580 may be drawn proximally while maintaining the position of the outer tubular body 578). Such relative motion may cause portions of the outer tubular body 578 containing the imaging arrays 586a, 586b to be displaced outward, thus pivoting the imaging arrays 586a, 586b to forward-looking positions as illustrated in FIG. 38B. To aid in controlling the motion of the imaging arrays 586a, 586b, the outer tubular body 578 may include first rigid portions 588 (e.g., of sufficient rigidity to perform the functions as described herein) that remain substantially straight as the imaging arrays 586a, 586b are pivoted. The first rigid portions 588 may be formed by adding appropriate stiffening members to the outer tubular body 578. Furthermore, the outer tubular body 578 may include second rigid portions 590 disposed proximate to the imaging arrays 586a, 586b. The second rigid portions 590 may serve to reduce or eliminate bending forces from being transmitted to the imaging arrays 586a, 586b during pivoting and to aid in alignment of the imaging arrays 586a, 586b. As shown in FIG. 38B, once the imaging arrays 586a, 586b are positioned in the forward-looking position, the lumen 582 is available for delivery of a suitable interventional device to a point distal to the catheter distal end 584.

The catheter 576 may also include any appropriate electrical interconnection to the imaging arrays 586a, 586b, including appropriate connection schemes described herein. For example, an electrical interconnection member may be disposed along the outer tubular body 578 and first and second rigid portions 588, 590.

Figure 39A:
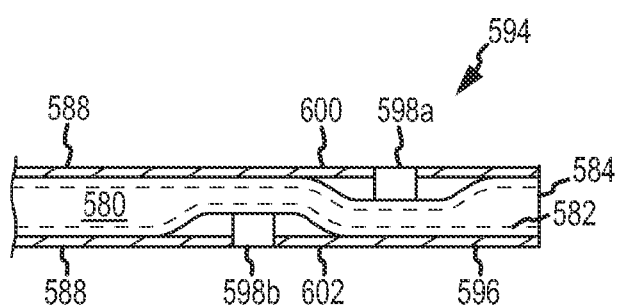
Figure 39B:
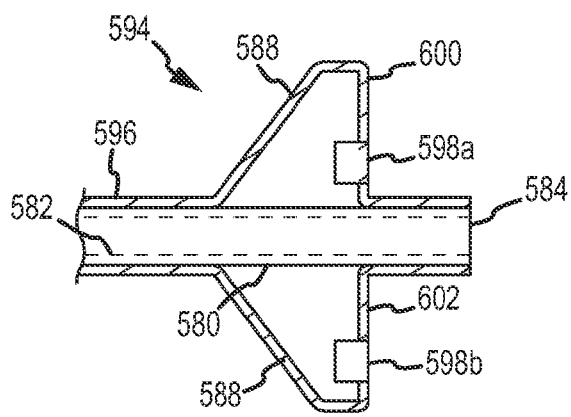

FIGS. 39A and 39B present a catheter 594 that is a variation of the catheter 576 of FIGS. 38A and 38B. As such, similar components are similarly numbered and will not be discussed with reference to FIGS. 39A and 39B. As illustrated in FIG. 39A, an introductory configuration of the catheter 594 includes a first imaging array 598a and a second imaging array 598b arranged in an offset (e.g., they occupy different positions along the length of the catheter 594) back-to-back arrangement, with an at least partially collapsed inner tubular body 580 proximate to the imaging arrays 598a, 598b. The inner tubular body 580 may include a lumen 582 therethrough. An outer tubular body 596 and the inner tubular body 580 may be fixed relative to each other at a distal end 584 of the catheter 594.

The imaging arrays 598a and 598b may be pivoted in a manner similar to as discussed above with reference to FIGS. 38A and 38B. The outer tubular body 596 may include second rigid portions 600, 602 disposed proximate to the imaging arrays 598a, 598b. The second rigid portions 600, 602 may serve to reduce or eliminate bending forces from being transmitted to the imaging arrays 598a, 598b during pivoting and to aid in alignment of the imaging arrays 598a, 598b. As shown in FIG. 38B, the second rigid portions 600, 602 may each position the imaging arrays 598a, 598b at unique distances from a central axis of the catheter 594.

The imaging arrays 586a, 586b, 598a, 598b of FIGS. 38A through 39B are illustrated as proximate to distal ends 584 of the catheters 576, 594. In alternate configurations, the imaging arrays 586a, 586b, 598a, 598b may be disposed at a predetermined distance form the distal ends 584. In this regard, the imaging arrays 586a, 586b, 598a, 598b may be disposed at any appropriate point along the catheters 576, 594.

Figure 40A:
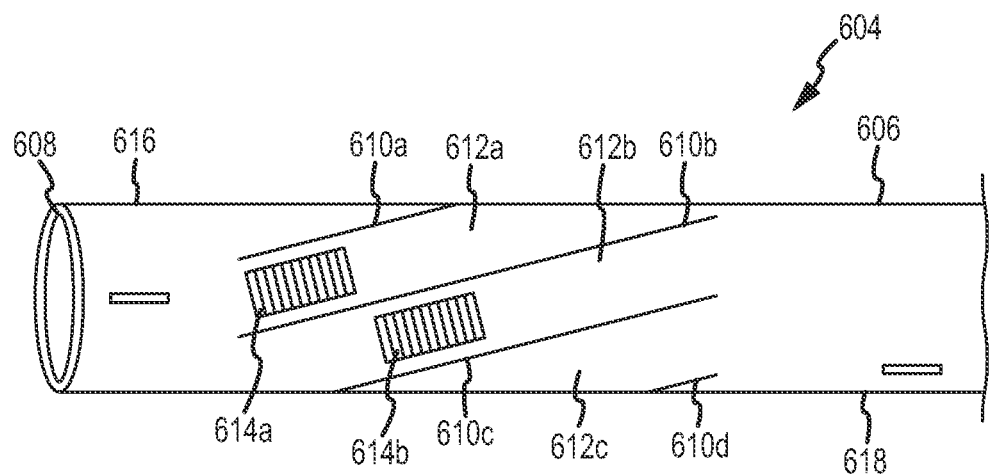
FIGS. 40A and 40B demonstrate a further embodiment of a catheter with ultrasound imaging arrays deployed on a plurality of arms.
Figure 40B:
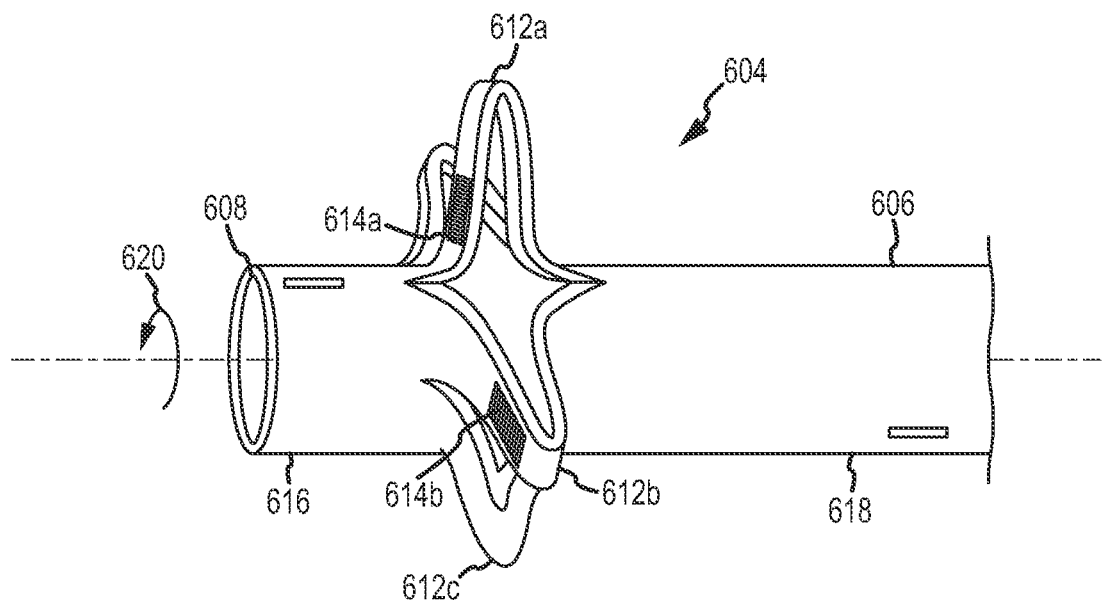

FIGS. 40A and 40B present a catheter 604 that includes a tubular body 606 with a lumen 608 therethrough. The tubular body 606 includes a plurality of spirally disposed slits (slits 610a, 610b, 610c and 610d are visible in FIG. 40A) defining a plurality of arms such as arms 612a, 612b and 612c. Any appropriate number of slits to define any appropriate number of arms may be included in the tubular body 606. At least one of the arms may include an ultrasound imaging array. For example, in the embodiment illustrated in FIGS. 40A and 40B, arms 612a and 612b include ultrasound imaging arrays 614a and 614b, respectively. A relative rotation (e.g., in the direction of directional arrow 620) of a distal portion 616 (distal to the arms 612a-612c) of the tubular body 606 to a proximal portion 618 (proximal to the arms 612a-612c) of the tubular body 606 may cause the arms to deflect outwardly as illustrated in FIG. 40B, moving the ultrasound imaging arrays 614a and 614b to generally forward-looking positions. An interventional device may be advanced through the lumen 608.

The relative rotation between the distal portion 616 and the proximal portion 618 may be achieved in any appropriate manner. For example, the catheter 604 may include an inner tubular body (not shown) similar to the inner tubular body of catheter 576 of FIGS. 38A and 38B. Such an inner tubular body may be secured to the tubular body 606 in the distal portion 616. In such an embodiment, rotation of the inner tubular body relative to the tubular body 616 may cause the distal portion 616 (by virtue of its securement to the inner tubular body) to rotate relative to the proximal portion 618, thereby causing the arms to deflect outwardly as illustrated in FIG. 40B. Moreover, the inner tubular body may include a lumen therethrough for deployment, for example, of an interventional device.

Figure 41A:
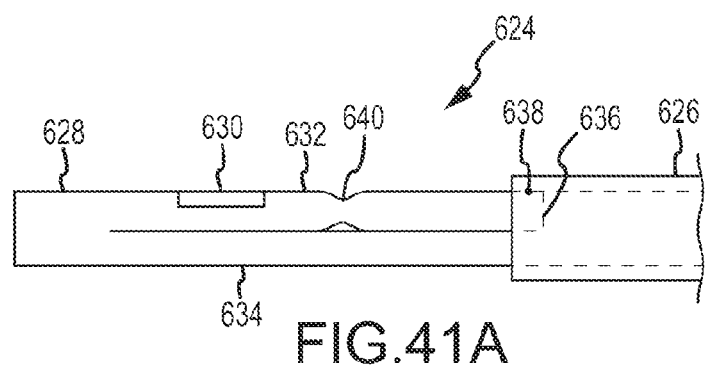
FIGS. 41A through 41C demonstrate a further embodiment of a catheter with an ultrasound imaging array deployed on a deflectable portion of an inner tubular body.
Figure 41B:
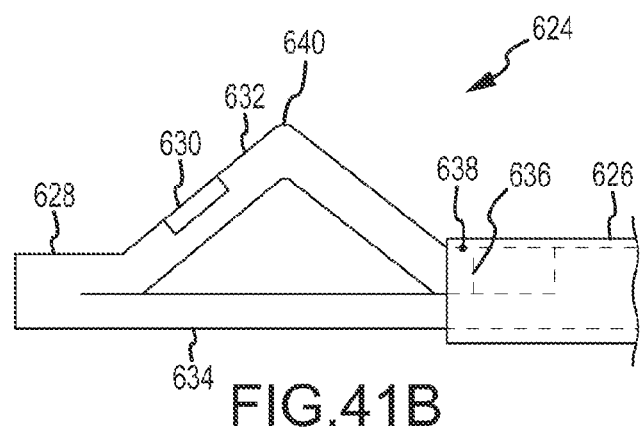

FIGS. 41A and 41B present a catheter 624 that includes an outer tubular body 626 and an inner tubular body 628. The inner tubular body 628 includes a lumen therethrough. An ultrasound imaging array 630 is interconnected to the inner tubular body 628. In the vicinity of the ultrasound imaging array 630, the inner tubular body 628 may be cut along the longitudinal axis of the inner tubular body 628, thus dividing the inner tubular body 628 into a first longitudinal portion 632 and a second longitudinal portion 634. The ultrasound imaging array 630 is disposed on the distal half of the first longitudinal portion 632. Distal ends of the first and second longitudinal portions 632, 634 may remain interconnected to each other and to a distal portion of the inner tubular body 628. A proximal end of the first longitudinal portion 632 may be severed from the remainder of the inner tubular body 628 along a transverse cut 636. The second longitudinal portion 634 remains connected to the inner tubular body 628. The proximal end of the first longitudinal portion 632 may be bonded or otherwise attached to the outer tubular body 626 at a bond 638. The first longitudinal portion 632 may include a hinge 640. The hinge 640 may be a portion of the first longitudinal portion 632 modified such that the first longitudinal portion 632 preferentially buckles and/or bends at the hinge 640 when the outer tubular body 626 is advanced distally relative to the inner tubular body 628 (and/or the inner tubular body 628 is retracted proximally relative to the outer tubular body 626).

To move the ultrasound imaging array 630 from the position illustrated in FIG. 41A (e.g., side-looking) to the position illustrated in FIG. 41B (e.g., at least partially forward-looking), the outer tubular body 626 is advanced distally relative to the inner tubular body 628. Since the proximal end of the first longitudinal portion 632 is bonded to the outer tubular body 626 and the distal end is connected of the inner tubular body 628, advancement of the outer tubular body 626 will cause the first longitudinal portion 632 to buckle at the hinge 640, thus pivoting the ultrasound imaging array 630 such that a field of view of the ultrasound imaging array 630 is at least partially forward-looking, as shown in FIG. 41B. The first longitudinal portion 632 may be returned to the position illustrated in FIG. 41A by proximally retracting the outer tubular body 626 relative to the inner tubular body 628.

Figure 41C:
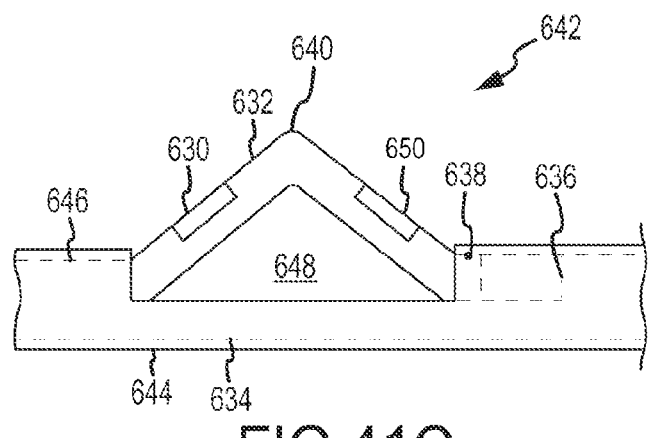

FIG. 41C presents a catheter 642 that is a variation of the catheter 624 of FIGS. 41A and 41B. As such, similar components are similarly numbered and will not be discussed with reference to FIG. 41C. As illustrated in FIG. 41C, an inner tubular body 646 may include first and second longitudinal portions 632, 634. However, as opposed to the embodiment of FIGS. 41A and 41B, where the first and second longitudinal portions 632, 634 are located proximate to the distal end of the catheter 642, the first and second longitudinal portions 632, 634 of the catheter 642 may be disposed at any appropriate point along the catheter 642. An outer tubular body 644 may include a window 648 to accommodate the deployment of the first longitudinal portion 632. The ultrasound imaging array 630 of FIG. 41C may be pivoted in a manner similar to as discussed above with reference to FIGS. 41A and 41B.

Catheter 642 also includes a second ultrasound imaging array 650 that is oriented to image in an at least partially rearward-looking direction. Ultrasound imaging array 650 may be in addition to the ultrasound imaging array 630 or it may be the only imaging array of catheter 642.

FIG. 41C illustrates a catheter with a section (e.g., the first longitudinal portion 632) that has a length and is configured such that when deployed, the ends of the length remain along the body of the catheter while a central section buckles outwardly from the body of the catheter. In this regard an ultrasound imaging array disposed on the central section may be deployed. Several other similarly configured embodiments are disclosed herein. These include, for example, the embodiments of FIGS. 7A through 8D, 38A through 39B, and 40A through 41B. In each of these embodiments, and in other appropriate embodiments disclosed herein, one or more ultrasound imaging arrays may be disposed at any appropriate location on the central section. Thusly, in these embodiments, ultrasound imaging arrays may be disposed such that they move to forward-looking positions, rearward-looking positions, or both when deployed.

The catheters 624, 642 may also include any appropriate electrical interconnection to the ultrasound imaging array 630, including appropriate connection schemes described herein. For example, electrical interconnection members may be disposed along the inner tubular bodies 628, 646.

In addition to deployment of an ultrasound imaging array to obtain images of an area of interest, deployment of ultrasound imaging arrays may also aid in positioning a lumen for introduction of an interventional device or other appropriate device. For example, the deployment of the ultrasound transducer array 37 of FIG. 8C (tri-lobe configuration) may result in each of the three lobes of the catheter moving against, for example, the walls of the blood vessel in which the catheter has been deployed. As a result, the end of the lumen 38 may be generally disposed in the center of the blood vessel. Other embodiments described herein, such as, for example, those associated with FIGS. 38A through 40B may also dispose the lumen generally at the center of a channel (e.g., blood vessel) during ultrasound imaging array deployment (e.g., if the channel is of a size that generally corresponds to the size of the catheter when the ultrasound imaging array is deployed).

Figure 42A:
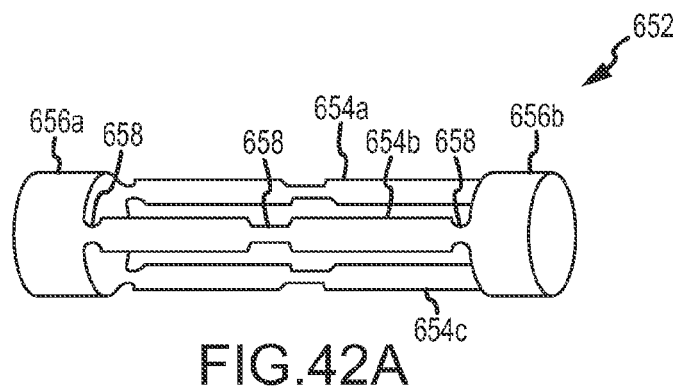
FIGS. 42A through 42C illustrate a spring element that may be disposed within a catheter.
Figure 42B:
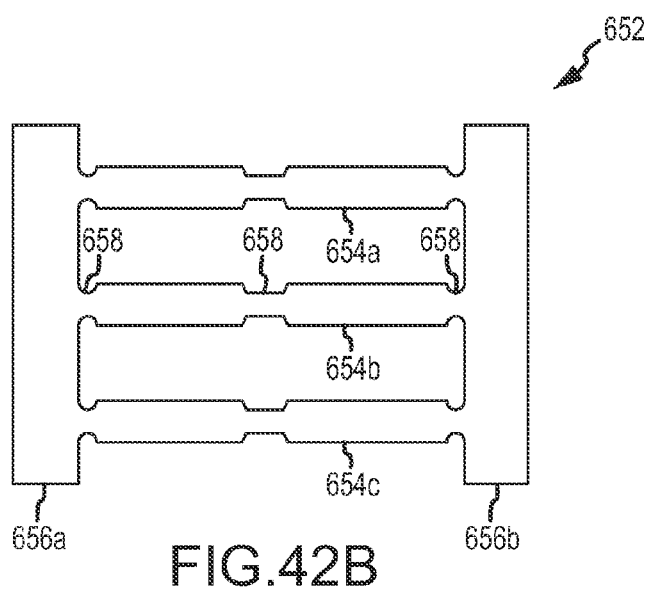
Figure 42C:
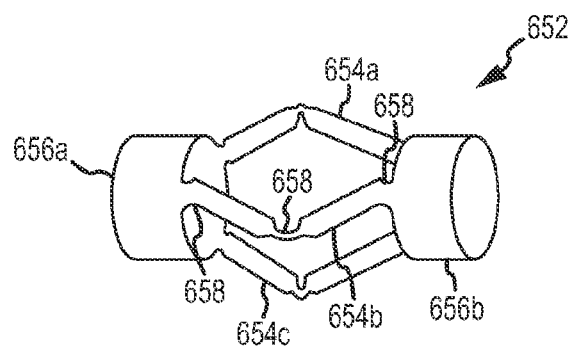

FIGS. 42A through 42C illustrate an exemplary spring element 652 that may be employed to generate a return force to aid in the return of a deployed ultrasound imaging array toward a pre-deployment position. The spring element 652 may include any appropriate number of springs. For instance and as illustrated in FIGS. 42A through 42C, the spring element 652 may include three springs 654a, 654b, 654c disposed between two end section 656a, 656b. The spring element 652 may, for example, be made from a blank, such as illustrated in FIG. 42B. The blank may be rolled to form the cylindrical configuration of FIG. 42A. The ends of the end sections 656a, 656b may be joined to maintain the cylindrical configuration of FIG. 42A. The springs 654a, 654b, 654c may include narrow regions, such as narrow regions 658 disposed along spring 654b, disposed at about the mid-point of the springs 654a, 654b, 654c and at each end of each spring 654a, 654b, 654c. The narrow regions may act as hinges, providing preferential bending points for the springs 654a, 654b, 654c. Accordingly, if a compressive force is applied to the spring element 652 (e.g., to end sections 656a, 656b), each of the springs 654a, 654b, 654c may buckle outwardly as illustrated in FIG. 42C. One or more ultrasound imaging arrays associated with one or more of the springs 654a, 654b, 654c would be consequently pivoted.

The configuration of spring element 652 may, for example, be disposed within the sidewall of the catheter body of the embodiment of FIG. 8C. Each of the springs 654a, 654b, 654c may be disposed within one of the lobes of the three lobe design of FIG. 8C. When integrated into the catheter of FIG. 8C, the spring element 652 may provide a return force biasing the catheter toward a straight, non-deployed position (e.g., for catheter insertion, positioning and removal). In another example, a spring element similar to the spring element 652 (e.g., with the appropriate number of appropriately shaped springs) may be deployed within the tubular body 606 of the catheter 604 of FIGS. 40A and 40B to provide a biasing force toward the straight configuration as illustrated in FIG. 40A.

In still another example, spring elements similar to the spring element 652 (e.g., but with two springs) may be deployed within the outer tubular bodies 578, 596 of the catheters 576, 594 of FIGS. 38A through 39B to provide a biasing force toward the straight configurations as illustrated in FIGS. 38A and 39A. In yet another example, an appropriately modified spring element similar to the spring element 652 (e.g., but with one spring) may be deployed within the inner tubular body 628 of the catheter 624 of FIG. 41A to provide a biasing force toward the straight configuration as illustrated in FIG. 41A.

Figure 43A:
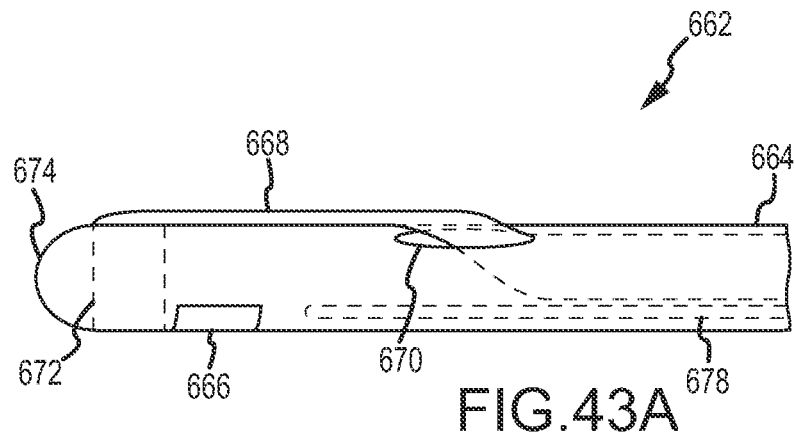
FIGS. 43A through 43C illustrate a catheter with a collapsible lumen that may be used to pivot an ultrasound imaging array.
Figure 43B:
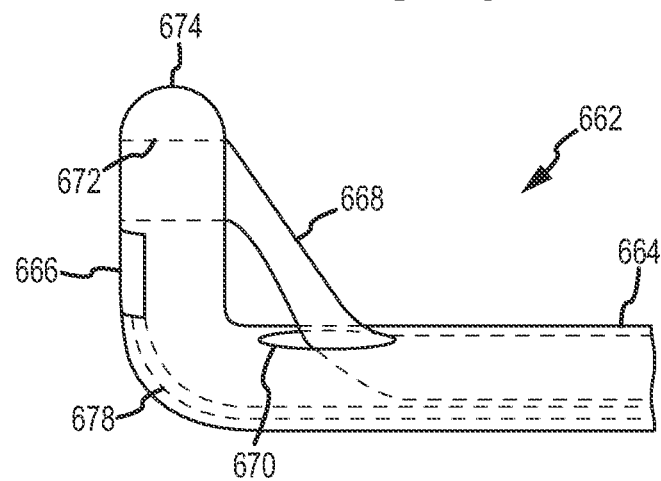
Figure 43C:
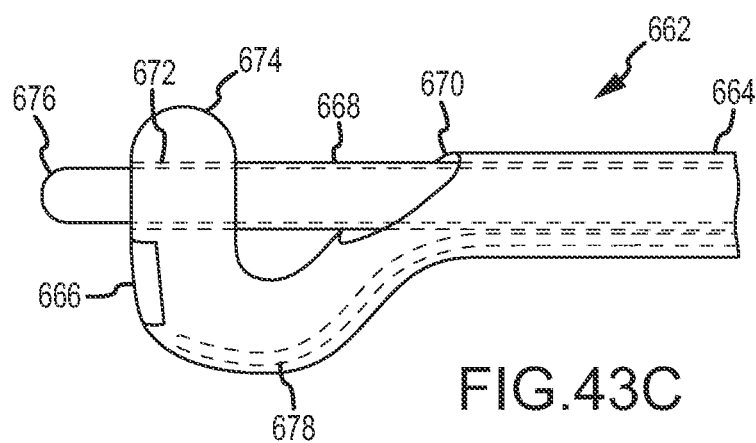

FIGS. 43A through 43C illustrate a catheter 662 that includes an outer tubular body 664. An ultrasound imaging array 666 is interconnected to the outer tubular body 664. The catheter 662 includes a collapsible lumen 668. The collapsible lumen 668 generally runs along the length of the catheter 662 in a central cavity of the outer tubular body 664. However, near the distal end of the catheter 662, the collapsible lumen 668 is routed through a side port 670 of the outer tubular body 664. For a predetermined distance, the collapsible lumen 668 runs along an exterior surface of the outer tubular body 664. Close to a distal end of the catheter 662 (at a point distal to the side port 670), the collapsible lumen 668 is interconnected to an end port 672. The end port 672 is a transverse through-hole proximate to a tip 674 of the catheter 662. The end port 672 may be configured such that an opening of the end port 672 is on the same side of the outer tubular body 664 as the front face of the ultrasound imaging array 666.

During insertion of the catheter 662 into a patient, the catheter 662 may be configured as illustrated in FIG. 43A with the tip 674 generally pointing along the longitudinal axis of the catheter 662. Furthermore, the portion of the collapsible lumen 668 external to the outer tubular body 664 (e.g., the portion of the collapsible lumen between the side port 670 and the end port 672) may be collapsed and generally positioned against the outside wall of the outer tubular body 664.

When it is desired to obtain images of a region distal to the tip 674, the collapsible lumen 668 may be pulled proximally relative to the outer tubular body 664. The result may be for the distal end of the catheter 662 to bend (upward when in the orientation shown in FIG. 43B) such that the ultrasound imaging array 666 is pivoted to a forward-looking position. To achieve such a bending motion, the distal end of the catheter 662 may be designed such that a region between the ultrasound imaging array 666 and the side port 670 is relatively flexible, while a region including the ultrasound imaging array 666 and distal to the ultrasound imaging array is relatively rigid. Accordingly, pulling the collapsible lumen 668 proximally may result in the relatively flexible region bending causing the ultrasound imaging array 666 front face and the opening of the end port 672 to pivot to a forward-looking configuration as illustrated in FIG. 43B.

When it is desired to insert an interventional device 676 into the patient, the interventional device 676 may be advanced distally through the collapsible lumen 668. As the interventional device 676 is advanced through the side port 670, the opening of the side port 670 may be displaced such that it is in line with the central cavity of the outer tubular body 664. As the interventional device 676 is advanced through the section of the collapsible lumen 668 external to the outer tubular body 664, that portion of the collapsible lumen 668 may also be moved such that it is aligned with the central cavity of the outer tubular body 664. As the interventional device 676 is advanced through the end port 672, the end port 672 may also be moved such that it too is aligned with the central cavity of the outer tubular body 664 and the section of the collapsible lumen 668 external to the outer tubular body 664. As the interventional device 676 is advanced, the ultrasound imaging array 666 may be displaced perpendicularly (e.g., downward when in the orientation illustrated in FIG. 43C) relative to the longitudinal axis of the catheter 662. It will be appreciated that the ultrasound imaging array 666 may remain operable to generate images distal to the tip 674 while the interventional device 676 is deployed distal to the tip 674.

Upon retraction of the interventional device 676, the catheter 662 may be returned to an aligned position (e.g., the configuration of FIG. 43A) for subsequent repositioning or removal. In an embodiment, the distal end of the catheter 662 may include a spring element that may return the catheter 662 to an aligned position once the external displacement forces (e.g., retraction force on the collapsible lumen 668 and/or displacement force due to the presence of the interventional device 676) have been removed. In another embodiment, a stylet (e.g., a relatively stiff wire, not shown) may be advanced through a stylet channel 678. The stylet may have sufficient stiffness to return the end of the catheter 662 toward an aligned position (e.g., the position of FIG. 43A).

The catheter 662 may also include any appropriate electrical interconnection to the ultrasound imaging array 666, including appropriate connection schemes described herein. For example, electrical interconnection members may be disposed along the outer tubular body 664.

Figure 44A:
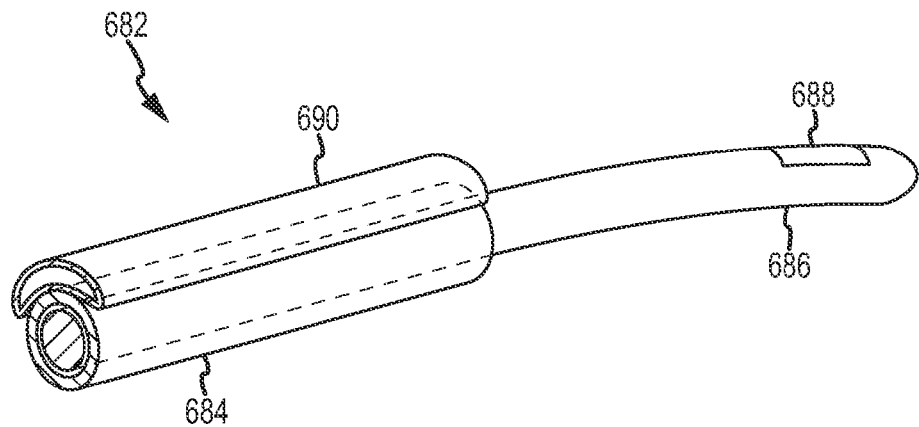
FIGS. 44A and 44B illustrate a catheter with a collapsible lumen.
Figure 44B:
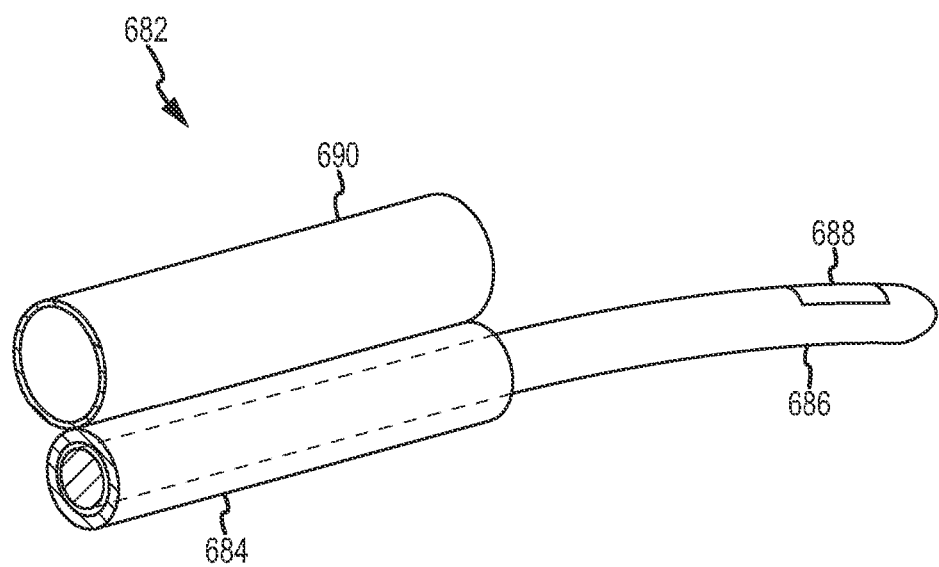

FIGS. 44A and 44B illustrate a catheter 682 that includes a tubular body 684. The tubular body may be sized and configured to deliver a steerable imaging catheter 686 to a selected site within a patient. The steerable imaging catheter 686 may include an ultrasound imaging array 688 disposed at a distal end thereof. Interconnected to an outer surface of the tubular body 684 may be a distensible channel 690. As illustrated in FIG. 44A, the distensible channel 690 may be inserted in a collapsed state, thereby reducing the cross section of the catheter 682 during insertion. Once the catheter 682 is satisfactorily positioned, an interventional device (not shown) may be delivered through the distensible channel 690. The distensible channel 690 may expand as the interventional device is advanced through the distensible channel 690. The distensible channel 690 may be made from any appropriate catheter material, including by way of example, ePTFE, silicone, urethane, PEBAX®, Latex, and/or any combination thereof. The distensible channel 690 may be elastic and may stretch to the diameter of the interventional device as the interventional device is introduced. In another arrangement, the distensible channel 690 may be inelastic and may unfold as the interventional device is introduced. For example, the distensible channel 690 may include a film tube. In another arrangement, the distensible channel 690 may include elastic and inelastic materials.

Figure 45A:
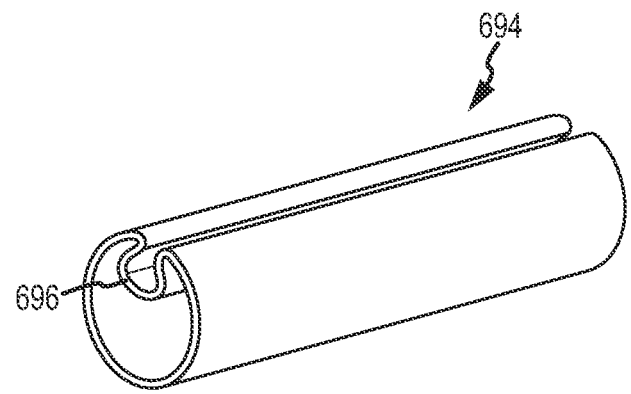
FIGS. 45A and 45B illustrate a catheter with an expandable lumen.
Figure 45B:
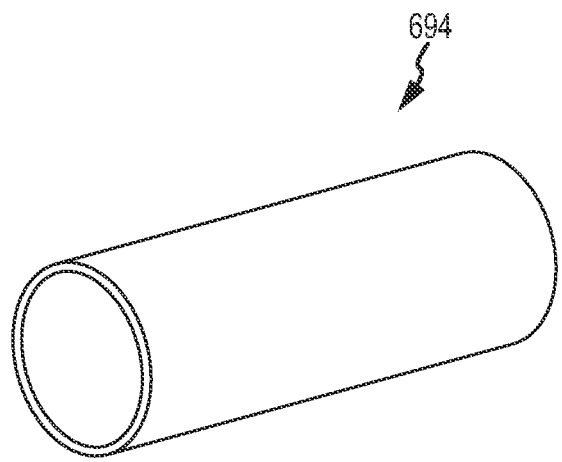

FIGS. 45A and 45B illustrate a catheter body 694. An introductory configuration is illustrated in FIG. 45A. The introductory configuration may include an invaginated portion 696. Once the catheter body 694 is satisfactorily positioned, an interventional device (not shown) may be delivered therethrough. The catheter body 694 may expand as the interventional device is advanced. Expansion of the catheter body 694 may comprise pushing the invaginated portion 696 outward until it forms part of a generally tubular catheter body as illustrated in FIG. 45B. In this regard, the catheter body 694 may be introduced into a patient while in a configuration with a first cross sectional area. Then, at a selected point, an interventional device may be inserted through the catheter body 694 and the catheter body 694 may expand to a second cross sectional area, where the second cross sectional area is larger than the first cross sectional area. The deformation of the catheter body 694 from the introductory configuration (FIG. 45A) to the expanded configuration (FIG. 45B) may be an elastic deformation, where after removal of the interventional device, the catheter body 694 is able to return toward its original profile, or it may be an at least partially plastic deformation.

Figure 46A:
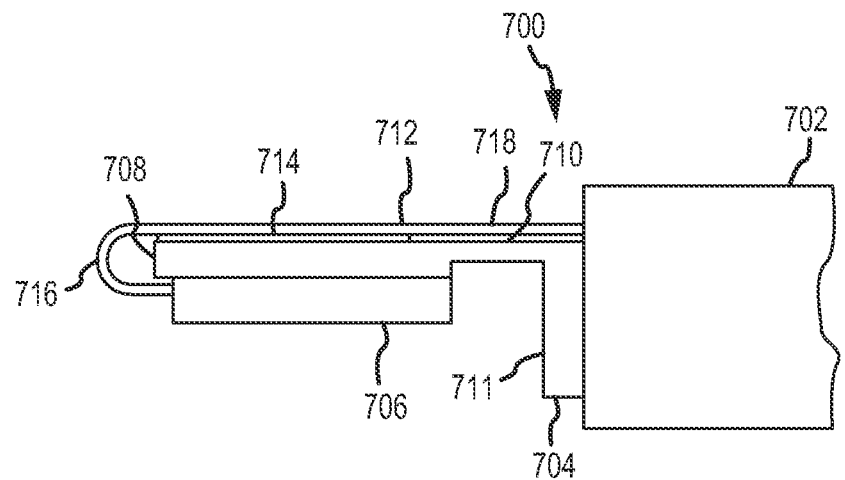
FIGS. 46A and 46B illustrate a catheter that includes an inner tubular body that includes a hinge portion and a tip support portion.
Figure 46B:
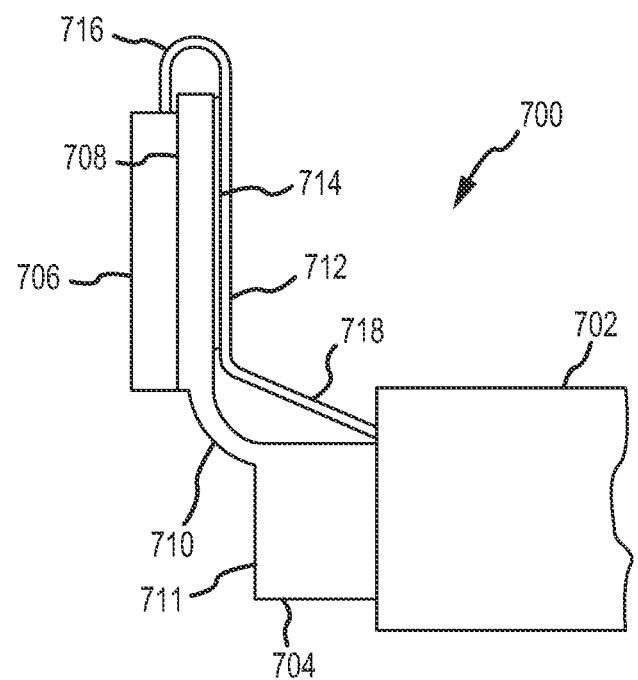

FIGS. 46A and 46B illustrate a catheter 700 that includes an outer tubular body 702 and an inner tubular body 704. The inner tubular body 704 may include a lumen therethrough. The catheter 700 also includes an ultrasound imaging array 706 interconnected to a tip support portion 708 of the inner tubular body 704. The tip support portion 708 of the inner tubular body 704 is interconnected to the distal end of the inner tubular body 704 by a hinge portion 710 of the inner tubular body 704. The tip support portion 708 and the hinge portion 710 of the inner tubular body 704 may be formed by, for example, cutting away a portion of the distal end of the inner tubular body 704, leaving a section (tip support portion 708) to which the ultrasound imaging array 706 may be interconnected and a section (hinge portion 710) that may act a hinge between the tip support portion 708 and a tubular end 711 of the inner tubular body 704. The inner tubular body 704 may be of any appropriate construction. For example, the inner tubular body 704 may be constructed similarly to the inner tubular body 80 of FIG. 5E, with the addition of a braided mesh to reinforce the inner tubular body 704. The braided mesh may serve to provide a return force to return the ultrasound imaging array 706 to an introductory position (as illustrated in FIG. 46A) from a deployed position (as illustrated in FIG. 46B).

The hinge portion 710 may allow the tip support portion 708 to pivot about the hinge portion 710 relative to the inner tubular body 704. An electrical interconnection member 712 may electrically interconnect to the ultrasound imaging array 706. The electrical interconnection member 712 is connected to a distal end of the ultrasound imaging array 706. The electrical interconnection member 712 may be bonded or otherwise fixed to a portion 714 of the tip support portion 708 on an opposite side of the tip support from the ultrasound imaging array 706. The electrical interconnection member 712 may include a loop 716 between the connection to the ultrasound imaging array 706 and the portion 714. The portion 714, by virtue of its fixed position relative to the tip support portion 708 may serve as a strain relief preventing strain associated with pivoting of the ultrasound imaging array 706 from being translated to the loop 716 and array 706 through the electrical interconnection member 712. A tether portion 718 of the electrical interconnection member 712 may be disposed between the bonded portion 714 and the point where the electrical interconnection member 712 enters into the outer tubular body 702. The tether portion 718 may be an unmodified portion of the electrical interconnection member 712 or it may be modified (e.g., structurally reinforced) to accommodate additional forces due to its serving as a tether. The tip support portion 708 and the ultrasound imaging array 706 may be encased or otherwise disposed within a tip (not shown).

During insertion into a patient, the catheter 700 may be arranged as in FIG. 46A with the ultrasound imaging array 706 in axial alignment with the inner tubular body 704 and a field of view of the ultrasound imaging array 706 pointing perpendicular to the longitudinal axis of the catheter 700 (downward as illustrated in FIG. 46A). In this regard, the catheter 700 may be substantially contained within a diameter equal to the outer diameter of the outer tubular body 702. As desired, the ultrasound imaging array 706 may be pivoted relative to the inner tubular body 704 by moving the inner tubular body 704 distally relative to the outer tubular body 702. Such relative motion will cause the ultrasound imaging array 706 to pivot about the hinge portion 710 due to the restraint of motion of the ultrasound imaging array 706 by the tether portion 718. The ultrasound imaging array 706 may be returned to the position illustrated in FIG. 46A by moving the inner tubular body 704 proximally relative to the outer tubular body 702.

Figure 47A:
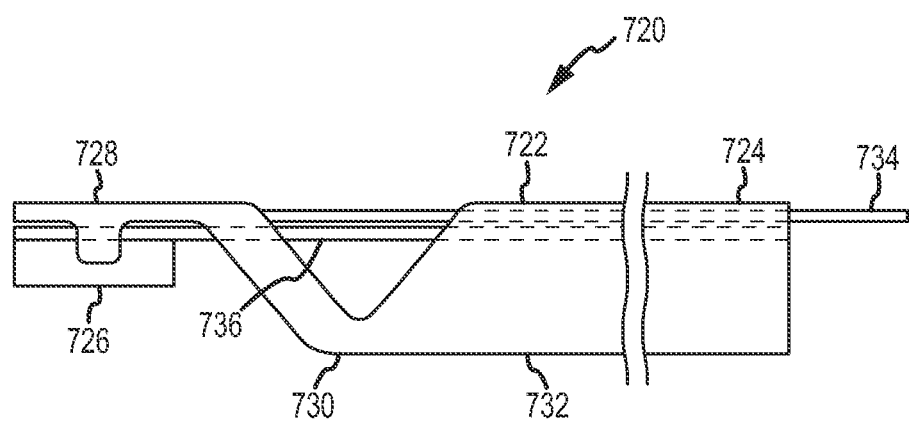
FIGS. 47A and 47B illustrate a catheter that includes tubular portion that includes a hinge.
Figure 47B:
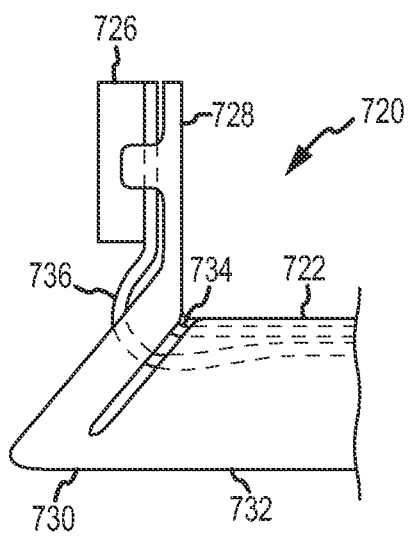

FIGS. 47A and 47B illustrate a catheter 720 that includes a tubular hinge 722 interconnected to a distal end of a tubular body 724. The tubular hinge 722 and tubular body 724 may include a lumen therethrough for the introduction of an interventional device. The catheter 720 also includes an ultrasound imaging array 726 interconnected to a support portion 728 of the tubular hinge 722. A hinge portion 730 of the tubular hinge 722 is disposed between the support portion 728 of the tubular hinge 722 and a tubular portion 732 of the tubular hinge 722. The catheter 720 further includes a wire 734 connected to the support portion 728 and running along the tubular hinge 722 and the tubular body 724. Pulling on a proximal end of the wire 732 may cause the support portion 728 to pivot relative to the tubular portion 732 about the hinge portion 730 as shown in FIG. 47B. Releasing the pulling force on the wire 734 and/or pushing on the proximal end of the wire 734 may result in the support portion 728 returning to the position shown in FIG. 47A. The tubular hinge 722 may include a shape memory material (e.g., Nitinol) and/or a spring material, such that the tubular hinge 722 may return toward the position illustrated in FIG. 47A once the pulling force is released. An electrical interconnection member 736 may electrically interconnect to the ultrasound imaging array 726. The electrical interconnection member 736 may be in the form of a flexboard or other flexible conductive member. The electrical interconnection member 736 may be routed through the tubular hinge 722 as shown in FIGS. 47A and 47B and then interconnect to a spirally wound electrical interconnection member disposed within the tubular body 724 (e.g., similar to the electrical interconnection member 104 of FIG. 5E). The support portion 728 and the ultrasound imaging array 726 may be encased or otherwise disposed within a tip (not shown).

During insertion into a patient, the catheter 720 may be arranged as in FIG. 47A with the ultrasound imaging array 726 in axial alignment with the tubular body 724 and a field of view of the ultrasound imaging array 726 pointing perpendicular to the longitudinal axis of the catheter 720 (downward as illustrated in FIG. 47A). In this regard, the catheter 720 may be substantially contained within a diameter equal to the outer diameter of the tubular body 724. As desired, the ultrasound imaging array 726 may be pivoted relative to the tubular body 724 by moving the wire 734 distally relative to the tubular body 724. Such relative motion will cause the ultrasound imaging array 726 to pivot about the hinge portion 730 due to the restraint of motion of the ultrasound imaging array 726 by the tubular hinge 722.

Figure 48A:
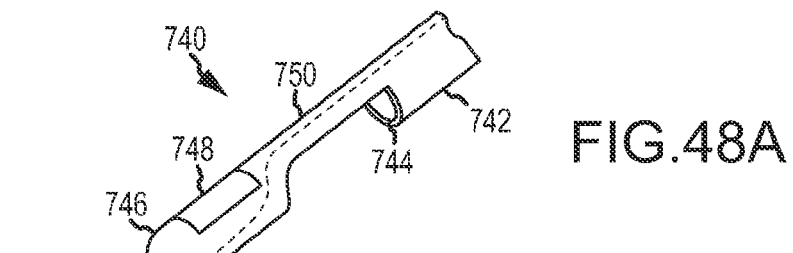
FIGS. 48A through 48D illustrate a catheter that includes a snare.
Figure 48B:
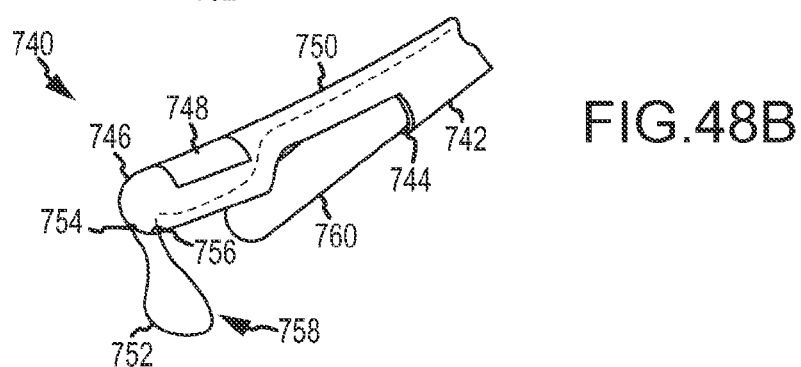

FIGS. 48A through 48D illustrate a catheter 740 that includes a tubular body 742 that includes a lumen 744 therethrough. The catheter 740 also includes a tip portion 746 that in turn includes an ultrasound imaging array 748. The tip portion 746 may be interconnected to the tubular body 742 by an intermediate portion 750. A wire 752 is attached to a distal portion of the tip portion 746 at a wire anchor 754. The wire 752 may be made from any appropriate material or group of materials, including, but not limited to, metals and polymers. The wire 752 is externally (relative to the tip portion 746) routed from the wire anchor 754 to a wire feed hole 756 on the distal portion of the tip portion 746. The wire 752 passes through the wire feed hole 756 and enters the interior of the tip portion 746. Thereafter, the wire 752 runs internally along the tip portion 746, intermediate portion 750, and at least a portion of the tubular body 742. A proximal end of the wire 752 (not shown) may be accessible to an operator of the catheter 740. The catheter 740 may be configured such that in the absence of externally applied forces, the tip portion 746 and intermediate portion 750 are axially aligned with the tubular body 742 as illustrated in FIG. 48A. In this regard, a shape memory material (e.g., Nitinol) or a spring material may be incorporated into the catheter 740 such that the tip portion 746 and intermediate portion 750 may return to the position illustrated in FIG. 48A once any external forces are released.

During insertion into a patient, the catheter 740 may be arranged as in FIG. 48A with the tip portion 746 and intermediate portion 750 in axial alignment with the tubular body 742 and a field of view of the ultrasound imaging array 748 pointing perpendicular to the longitudinal axis of the catheter 740 (generally upward as illustrated in FIG. 48A). In this regard, the tip portion 746 may be substantially contained within a diameter equal to the outer diameter of the tubular body 742.

Figure 48C:
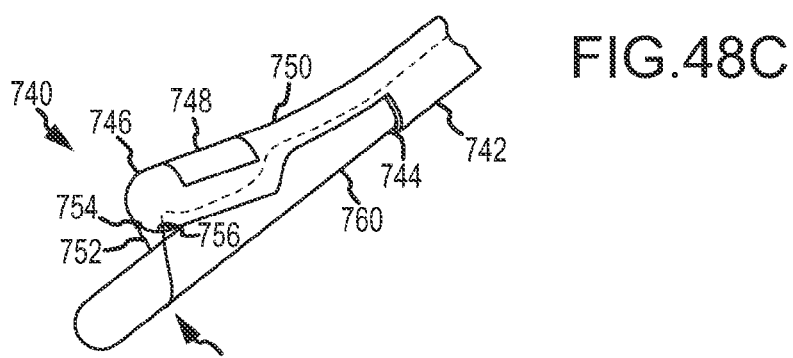
Figure 48D:
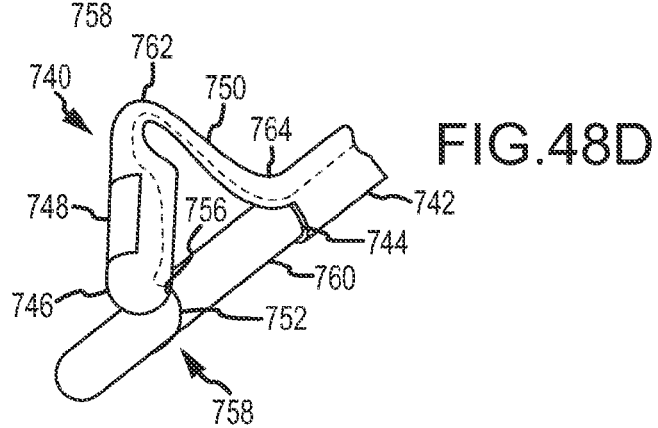

As desired, the tip portion 746 that includes the ultrasound imaging array 748 may be pivoted relative to the tubular body 742 to a forward-looking position where the ultrasound imaging array 748 may be used to generate images of a volume distal to the catheter 740. To pivot the tip portion 746, a first step may be to feed a portion of the wire 752 through the wire feed hole 756 to form a snare 758 (a loop of the wire 752 external to the tip portion 746) illustrated in FIG. 48B. The wire feed hole 756 and corresponding passages within the tip portion 746 may be configured such that, upon such feeding, the wire 752 generally forms the snare 758 in a plane perpendicular to the longitudinal axis of the catheter 740 and encircling a cylindrical distal extension of the lumen 744. Accordingly, when an interventional device 760 is fed distally from the lumen 744, it will pass through the snare 758 as illustrated in FIG. 48C. Once the interventional device 760 is fed through the snare 758, the wire 752 may be drawn into the tip portion 746 through the wire feed hole 756 such that the snare 758 captures the interventional device 760 such that the distal end of the tip portion 746 and the interventional device 760 move in tandem. One captured, the interventional device 760 may be moved proximally relative to the tubular body 742, causing the tip portion 746 to pivot such that the ultrasound imaging array 748 is in an at least partially forward-looking position as illustrated in FIG. 48D. The intermediate portion 750 may be configured such that it bends in a first bend area 762 and a second bend area 764 to facilitate the pivoting of the tip portion 746 as illustrated in FIG. 48D. To return the tip portion 746 toward it positioning of FIG. 48A, the interventional device 760 may, while captured by the snare 758, be advanced distally and/or the snare 758 may loosened, thereby decoupling the distal end of the tip portion 746 and the interventional device 760 (thus allowing the shape memory material and/or spring material to move the tip portion 746).

The catheter 740 may also include any appropriate electrical interconnection to the ultrasound imaging array 748, including appropriate connection schemes described herein. For example, electrical interconnection members may be disposed along the tubular body 742 and the intermediate portion 750.

Figure 49A:
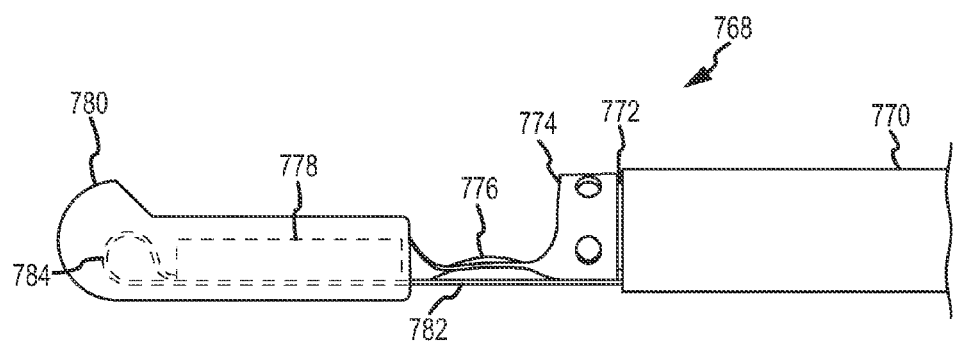
FIGS. 49A and 49B illustrate a catheter that includes an electrical interconnection member that connects to a distal end of an ultrasound imaging array.
Figure 49B:
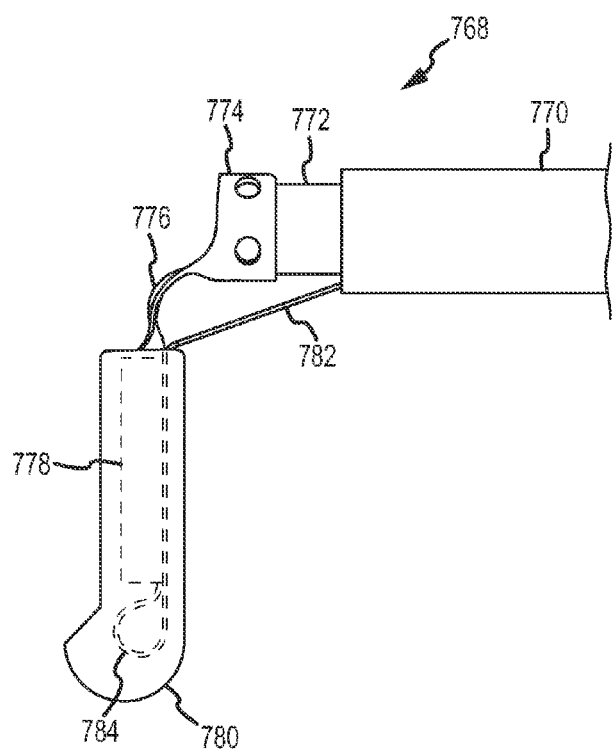

FIGS. 49A and 49B illustrate a catheter 768 that includes an outer tubular body 770 and an inner tubular body 772. The catheter 768 also includes an ultrasound imaging array 778 and a support 774 and with a hinge portion 776. The support 774 and the ultrasound imaging array 778 may be disposed within a tip 780. The catheter 768 is somewhat similar to the catheter 54 of FIGS. 5B through 5D and therefore similar traits will not be discussed. An exemplary difference between the catheter 768 and the catheter 54 is that a flexboard 782 of catheter 768 is disposed along an outside bottom (as viewed in FIG. 49A) surface of the support 774 and includes an end loop 784 where the flexboard 782 is connected to the distal end of the ultrasound imaging array 778. Such a design may reduce forces (e.g., act as a strain relief) translated to the junction between the flexboard 782 and the ultrasound imaging array 778 due to pivoting of the ultrasound imaging array 778. Such a design also obviates the need for the flexboard 782 to be threaded through or around the support 774 to enable interconnection to the ultrasound imaging array 778 at the proximal end of the ultrasound imaging array 778. In turn, this allows for a unitary hinge portion 776 (as opposed to the dual hinge portions 86a, 86b of the catheter 54 of FIG. 5B) such as illustrated in FIGS. 49A and 49B. Moreover, the strain relief of the ultrasound imaging array 778 to flexboard 782 connection provided by the configuration of FIGS. 49A and 49B may be beneficial in enabling the flexboard 782 to also serve the function of a tether (similar to the tether 78 of FIG. 5B). In an alternate embodiment, the catheter 768 of FIGS. 49A and 49B may include a tether similar to tether 78 of FIG. 5B.

Figure 50:
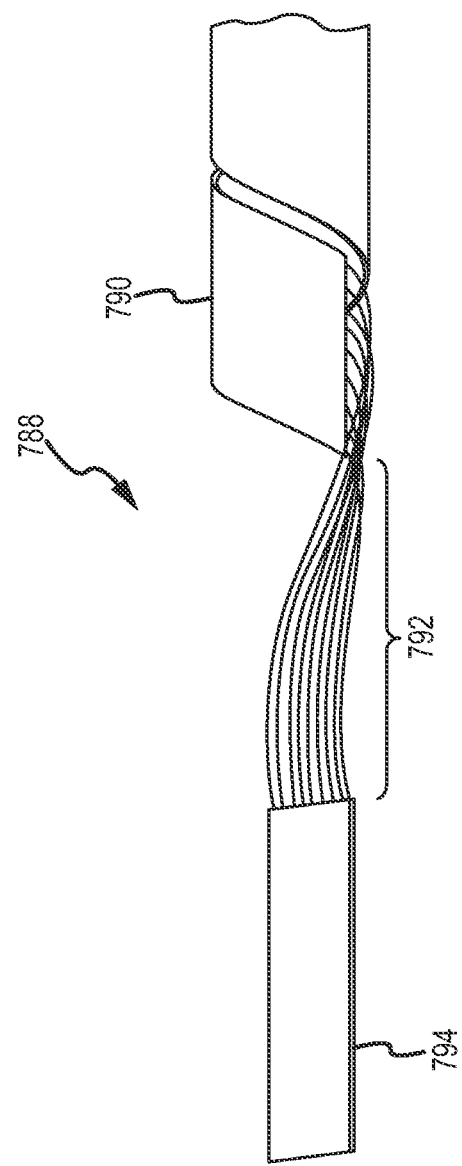
FIG. 50 illustrates a method of electrically interconnecting a spirally wound portion of a conductor to an ultrasound imaging array.

FIG. 50 depicts an embodiment of an electrical interconnection member 788. The electrical interconnection member 788 may, for example, take the place of the assembly illustrated in FIG. 5F in the catheter 50 illustrated in FIGS. 5A through 5E. Moreover, electrical interconnection member 788 or features thereof may be used in any appropriate embodiment disclosed herein. The electrical interconnection member 788 includes a helically disposed portion 790 that may be disposed in a tubular body of a catheter (e.g., similar to the electrical interconnection member 104 of FIG. 5F). The helically disposed portion 790 of the electrical interconnection member 788 may include a plurality of individual conductors bound together in a side-by-side arrangement. The electrical interconnection member 788 may include a non-bonded portion 792 where the individual conductors of the electrical interconnection member 788 are not bonded together. The individual conductors of the non-bonded portion 792 may each be individually insulated to help prevent shorting between the conductors. The non-bonded portion 792 may provide a portion of the electrical interconnection member 788 that is relatively more flexible than the helically disposed portion 790. In this regard, the non-bonded portion 792 may have sufficient flexibility to provide an electrical connection between members that are hinged relative to each other. Therefore, in appropriate embodiments described herein, the non-bonded portion 792 of the electrical interconnection member 788 may replace a flexboard or other flexible electrical interconnections.

The electrical interconnection member 788 may further include an array connection portion 794 configured to electrically connect to an ultrasound imaging array (not shown in FIG. 50). The array connection portion 794 may, for example, include the plurality of individual conductors bound together in the same side-by-side arrangement as in the helically disposed portion. In this regard, the electrical interconnection member 788 may be configured by removing the bonding structure between conductors in the non-bonded portion 792, while leaving the bonding in tact in the helically disposed portion 790 and the array connection portion 794. The conductors of the array connection portion 794 may be selectively exposed such that they may be electrically interconnected to appropriate members of an ultrasound imaging array. In another embodiment, the array connection portion 794 may interconnect to an intermediate member that may be arranged to provide electrical connections from the individual conductors of the array connection portion 794 to the appropriate members of an ultrasound imaging array.

An alternate embodiment of the electrical interconnection member 788 may be configured without the array connection portion 794. Such a configuration may utilize "flying leads" where each conductor of the non-bonded portion 792 remains electrically interconnected to the helically disposed portion 790 on one end and unconnected on the other end. These unconnected flying leads may then, for example, be individually bonded to corresponding conductors on an ultrasound imaging array.

Figure 51A:
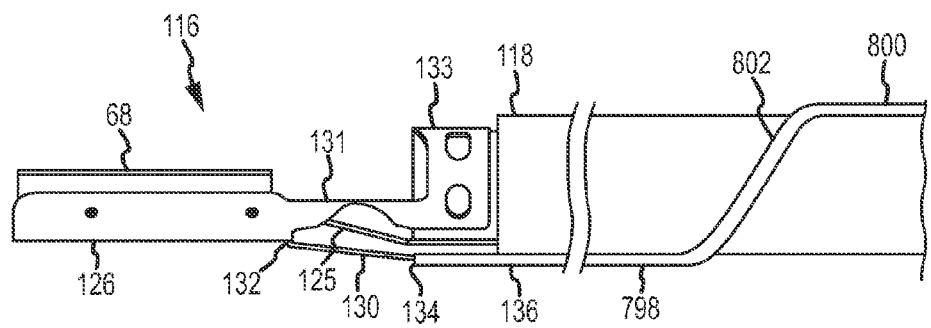
FIGS. 51A and 51B illustrate catheters with pull wires that transition from a first side of a catheter to a second side of the catheter.
Figure 51B:
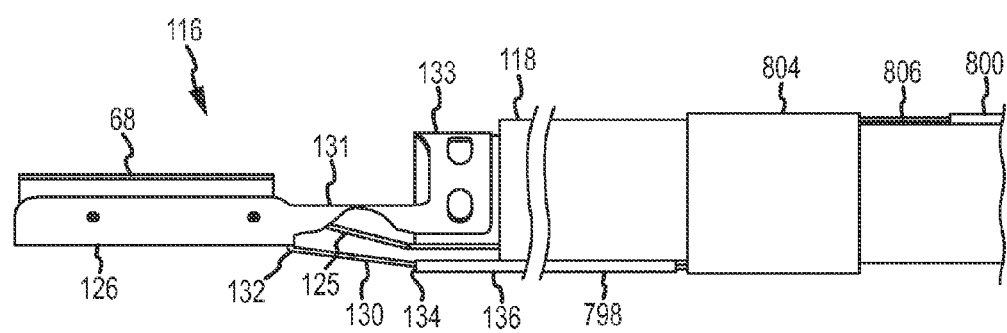

In embodiments described herein wherein a movable elongate member (e.g., pull wire) is employed to cause a deflection of an ultrasound imaging array, the elongate member is generally routed along one side of a catheter body. In a variation of such embodiments, the elongate member may be configured such that a first portion of it is disposed along a first side of the catheter body, and a second portion of the elongate member is disposed along a second side of the catheter body. For example, FIGS. 51A and 51B illustrate the embodiment of FIG. 6B with a first portion 798 of the pull wire housing 136 and pull wire 130 disposed along a first side of the catheter body 118 and a second portion 800 of the pull wire housing and pull wire disposed along a second side of the catheter body 118. Other components of FIG. 6B are as previously described and will not be described further. Such configurations may help to reduce the level of non-symmetrical forces imparted onto the catheter body 118 (e.g., during catheter placement and/or operation) by the pull wire housing 136 and pull wire 130. This may lead to an increased ability to maintain catheter stability during tip deployment.

Figure 52A:
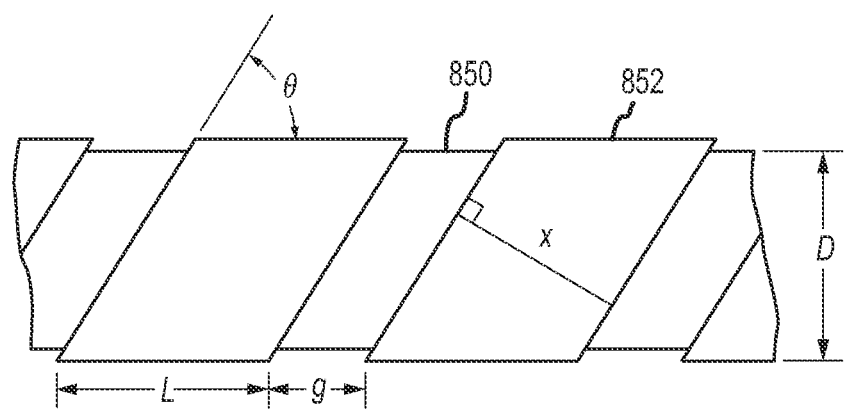
FIGS. 52A and 52B illustrate an electrical interconnection member wrapped about a substrate.

FIG. 51A illustrates an embodiment where the first portion 798 of the pull wire housing 136 and pull wire 130 is connected to the second portion 800 of the pull wire housing 136 and pull wire 130 by a transition section 802. The transition section 802 is a section of the of the pull wire housing 136 and pull wire 130 that is spirally would about the catheter body 118. FIG. 52A illustrates en embodiment where the first portion 798 of the pull wire housing 136 and pull wire 130 is connected to the second portion 800 of the pull wire housing 136 and a second pull wire 806 via a coupling 804. The coupling 804 may be cylindrically disposed about a portion of the length of the catheter body 118 and may be operable to slide along that portion of the length of the catheter body 118 in response to forces imparted on the pull wires 130, 806. The second pull wire 806 may be disposed on the second side of the catheter body 118 and is attached to the coupling 804. The pull wire 130 is also attached to the coupling 804. When an operator pulls the second pull wire 806 proximally, the coupling 804 is displaced proximally, and the pull wire 130, by virtue of its connection to the coupling 804, is also pulled proximally. Both of the illustrated pull wire configurations of FIGS. 51A and 51B may also operate as push wires.

Figure 52B:
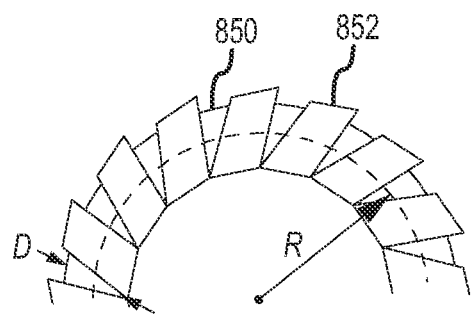

FIGS. 52A and 52B illustrate a portion of a catheter body that includes a substrate 850 and a helically wound electrical interconnection member 852. The substrate 850 and electrical interconnection member 852 may be incorporated into any appropriate embodiment disclosed herein, including embodiments where an inner tubular body contains the electrical interconnection member 852 and embodiments where an outer tubular body contains the electrical interconnection member 852. The substrate 850 is the layer about which the electrical interconnection member 852 is wound. For example, the substrate 850 would be the inner tie layer 102 in the embodiment of FIG. 5E.

Turning to FIG. 52A, the electrical interconnection member 852 may have a width of (x) and the substrate may have a diameter of (D). The electrical interconnection member 852 may be wrapped about the substrate 850 such that there exists a gap (g) between subsequent coils of the electrical interconnection member 852. The electrical interconnection member 852 may be wound at an angle of (θ), thereby resulting in a length (L) of each winding of the electrical interconnection member 852 along the longitudinal axis of the catheter. Accordingly, the length (L) is related to the angle (θ) as follows:

$$L = x/\sin(\theta) \quad\quad\quad \text{Equation 1}$$

Furthermore, the angle (θ) is related to (D), (L) and (g) as follows:

$$\tan(\theta) = (\pi(D))/(z(L+g)) \quad\quad\quad \text{Equation 2}$$

Where (z) is the number of unique electrical interconnection members 852 wound about the substrate 850 (in the catheter of FIGS. 52A and 52B, (z)=1). For a particular electrical interconnection member 852, (x) is known. Also, for a particular substrate 850, (D) will be known. And for a particular catheter, (z) and (g) may be known. Accordingly, Equations 1 and 2 may have two unknown variables, (θ) and (L). Therefore, for given values of (D), (z), (g) and (x), (θ) and (L) may be determined. In an exemplary catheter where the diameter (D) of the substrate was 0.130 inches (3.3 mm), the number (z) of electrical interconnection members 852 was 1, the desired gap (g) was 0.030 inches (0.76 mm), and the electrical interconnection member 852 width (x) was 0.189 inches (4.8 mm), (θ) was found to be 58 degrees and (L) was found to be 0.222 inches (5.64 mm).

Turning to FIG. 52B, for a given catheter, there may be a minimum desired bend radius (R). To ensure that subsequent coils of the electrical interconnection member 852 do not overlap each other when the catheter is bent to the minimum desired bend radius (R), the gap (g) should equal or exceed a minimum gap ($g_m$). The minimum gap ($g_m$) is the gap size where subsequent coils of the electrical interconnection member 852 come into contact with each other when the catheter is bent to the minimum desired bend radius (R) as illustrated in FIG. 52B. The minimum desired bend radius (R) is related to the length (L) and minimum gap ($g_m$) as follows:

$$(L+g_m)/L=R/(R-(D/2)) \qquad \text{Equation 3}$$

Plugging the values for (L) (0.222 inches (5.64 mm)) and (D) (0.130 inches (3.3 mm)) into Equation 3 and using a minimum desired bend radius (R) of 1.0 inch (25.4 mm), yields a minimum gap ($g_m$) of 0.015 inches (0.38 mm). Accordingly, the gap (g) of 0.030 inches (0.76 mm) used above in Equations 1 and 2 exceeds the minimum gap ($g_m$) of 0.015 inches (0.38 mm) for a bend radius (R) of 1.0 inch (25.4 mm) from Equation 3. Therefore the gap (g) of 0.030 (0.76 mm) inches should not result in subsequent coils of the electrical interconnection member 852 coming into contact with each other when the catheter is bent to a bend radius (R) of 1.0 inch (25.4 mm).

Additional modifications and extensions to the embodiments described above will be apparent to those skilled in the art. Such modifications and extensions are intended to be within the scope of the present invention as defined by the claims that follow.

What is claimed is:

1. A catheter comprising:
    an outer tubular body having a wall, a proximal end and a distal end;
    a lumen for delivering an interventional device extending through the outer tubular body from the proximal end of the outer tubular body to an exit port located distal to the proximal end of the outer tubular body;
    a first electrical conductor portion comprising a plurality of electrical conductors arranged side-by-side with electrically non-conductive material therebetween, the first electrical conductor portion being helically disposed along and about at least a portion of the lumen and extending from the proximal end of the outer tubular body to the distal end of the outer tubular body;
    a second electrical conductor portion, electrically interconnected to the first electrical conductor portion at the distal end of the outer tubular body, comprising a plurality of electrical conductors; and
    a deflectable imaging device, located distal to and deflectable relative to the distal end of the outer tubular body, wherein the second electrical conductor portion is connected to and extends distally from the distal end of the outer tubular body, between the first electrical conductor portion and the deflectable imaging device, and is electrically interconnected to the deflectable imaging device, and wherein the second electrical conductor portion is bendable distal to and relative to the distal end of the outer tubular body in response to deflection of the deflectable imaging device.

2. The catheter of claim 1, further comprising a first electrical conductor portion to second electrical conductor portion junction, wherein a distal end of the first electrical conductor portion is angled across a distal end thereof at said junction, and wherein corresponding ones of said plurality of electrical conductors of said first electrical conductor portion and of second electrical conductor portion are electrically interconnected at said junction.

3. The catheter of claim 1, wherein the deflectable imaging device comprises an ultrasound transducer array.

4. The catheter of claim 1, wherein the second electrical conductor portion comprises electrically conductive traces disposed on a flexible substrate.

5. The catheter of claim 4, wherein said flexible substrate is bendable through an arc of at least 90 degrees.

6. The catheter of claim 4, wherein the substrate includes a bending region located distal to the distal end of said outer tubular body.

7. The catheter of claim 1, wherein the helically disposed portion of the first electrical conductor portion is helically disposed in a non-overlapping manner, wherein a width of the first electrical conductor portion is at least greater than a gap between successive coils of the helically disposed first electrical conductor portion.

8. The catheter of claim 7, wherein the gap comprises a first gap portion located distal to a second gap portion, wherein the first gap portion is wider than the second gap portion.

9. The catheter of claim 1, wherein at least a portion of the first electrical conductor portion is helically disposed about a center axis of the outer tubular body.

10. The catheter of claim 1, wherein at least a portion of the first electrical conductor portion is embedded within the outer tubular body.

11. The catheter of claim 10, wherein said outer tubular body comprises:
    a first layer disposed radially inside the first electrical conductor portion, the first layer having a dielectric constant of less than 2.2; and
    a second layer disposed radially outside the first electrical conductor portion, the second layer having a dielectric constant of less than 2.2.

12. The catheter of claim 11, wherein said outer tubular body comprises:
    at least one tie layer interposed between the first electrical conductor portion and at least one of the first layer and the second layer, said at least one tie layer having a melt temperature lower than that of the first and second layers.

13. The catheter of claim 10, wherein said outer tubular body comprises:
    a first layer disposed radially outside the first electrical conductor portion, wherein the first layer has a withstand voltage of at least about 2,500 volts AC; and
    a second layer disposed radially outside the first layer, wherein the second layer has a withstand voltage of at least about 2,500 volts A.

14. The catheter of claim 13, wherein said outer tubular body comprises:
    at least one tie layer interposed between the first electrical conductor portion and at least one of the first layer and the second layer, said at least one tie layer having a melt temperature lower than that of the first and second layers.

15. The catheter of claim 10, wherein said outer tubular body comprises:
    a first layer disposed radially inside the first electrical conductor portion, wherein the first layer has a withstand voltage of at least about 2,500 volts AC; and
    a second layer disposed radially inside the first layer, wherein the second layer has a withstand voltage of at least about 2,500 volts AC.

16. The catheter of claim 15, wherein said outer tubular body comprises:
    at least one tie layer interposed between the first electrical conductor portion and at least one of the first layer and the second layer, said at least one tie layer having a melt temperature lower than that of the first and second layers.

17. The catheter of claim 1, wherein the deflectable imaging device is permanently located distal to the distal end of the outer tubular body.

18. The catheter of claim 17, wherein the distal end of the outer tubular body is incapable of being disposed within a field of view of the deflectable imaging device.

19. The catheter of claim 17, wherein a field of view of the deflectable imaging device is free of the outer tubular body when the deflectable imaging device is positioned for advancement of the catheter within a body.

20. The catheter of claim 1, wherein the deflectable imaging device is interconnected to the distal end of the outer tubular member.

21. The catheter of claim 1, wherein the deflectable imaging device is deflectable away from a longitudinal axis of the outer tubular body.

22. The catheter of claim 1, wherein a center axis of the outer tubular body coincides with a center axis of the lumen.

23. The catheter of claim 1, wherein the first electrical conductor portion is embedded in the outer tubular body from the proximal end to the distal end thereof.

24. The catheter of claim 23, wherein the first electrical conductor portion is defined by a ribbon-shaped member.

25. The catheter of claim 1, wherein the second electrical conductor portion comprises electrically conductive traces disposed on a flexible substrate.

26. The catheter of claim 25, wherein the substrate includes a curved section disposed within the outer tubular body and contacting the first electrical conductor portion.

27. The catheter of claim 26, wherein the curved section is curved to correspond with a curvature of the outer tubular body.

28. The catheter of claim 25, further comprising a first electrical conductor portion to second conductor portion junction, wherein the substrate includes a bending region having a width less than a width of the first electrical conductor portion at said junction.

29. The catheter of claim 28, wherein said bending region is located distal to the distal end of said outer tubular body.

30. A catheter comprising:
    an outer tubular body having a wall, a proximal end and a distal end;
    a lumen for delivering an interventional device extending through the outer tubular body from the proximal end of the outer tubular body to an exit port located distal to the proximal end of the outer tubular body;
    a first electrical conductor portion comprising a plurality of electrical conductors arranged side-by-side with electrically non-conductive material therebetween, the first electrical conductor portion being helically disposed along and about at least a portion of the lumen and extending from the proximal end of the outer tubular body to the distal end of the outer tubular body, wherein the first electrical conductor portion is embedded with the outer tubular body from the proximal end to the distal end thereof;
    a second electrical conductor portion, electrically interconnected to the first electrical conductor portion at the distal end of the outer tubular body, comprising a plurality of electrical conductors; and
    a deflectable imaging device, located distal to and deflectable relative to the distal end of the outer tubular body, wherein the second electrical conductor portion is connected to and extends distally from the distal end of the outer tubular body, between the first electrical conductor portion and the deflectable imaging device, and is electrically interconnected to the deflectable imaging device, and wherein the second electrical conductor portion is bendable distal to and relative to the distal end of the outer tubular body in response to deflection of the deflectable imaging device.

31. The catheter of claim 30, wherein at least a portion of the deflectable imaging device is permanently located distal to the distal end of the outer tubular body.

32. The catheter of claim 31, wherein the deflectable imaging device is interconnected to the distal end of the outer tubular member.

33. The catheter of claim 32, wherein the deflectable imaging device is deflectable away from a center axis of the outer tubular body, and wherein the center axis of the outer tubular body coincides with a center axis of the lumen.

34. The catheter of claim 30, wherein the second electrical conductor portion comprises electrically conductive traces disposed on a flexible substrate, wherein the substrate includes a curved section disposed within the outer tubular body and contacting the first electrical conductor portion, and wherein the substrate includes a bending region located distal to the distal end of said outer tubular body.

35. The catheter of claim 34, wherein the curved section is curved to correspond with a curvature of the outer tubular body.

* * * * *

UNITED STATES PATENT AND TRADEMARK OFFICE
CERTIFICATE OF CORRECTION

| | | |
|---|---|---|
| PATENT NO. | : 8,852,112 B2 | Page 1 of 1 |
| APPLICATION NO. | : 12/347637 | |
| DATED | : October 7, 2014 | |
| INVENTOR(S) | : Paul A. Bielewicz et al. | |

It is certified that error appears in the above-identified patent and that said Letters Patent is hereby corrected as shown below:

In the claims

At Column 62, Claim 13, line 59, change "least about 2,500 volts A." to "least about 2,500 volts AC.".

Signed and Sealed this
Third Day of November, 2015

Michelle K. Lee
*Director of the United States Patent and Trademark Office*